United States Patent
Leuhr et al.

(10) Patent No.: US 6,828,317 B2
(45) Date of Patent: Dec. 7, 2004

(54) ANTIMICROBIAL THIADIAZINONE DERIVATIVES AND THEIR APPLICATION FOR TREATMENT OF BACTERIAL INFECTIONS

(75) Inventors: Gary W. Leuhr, Hayward, CA (US); Mikhail F. Gordeev, Castro Valley, CA (US); Dinesh V. Patel, Fremont, CA (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/357,515

(22) Filed: Feb. 4, 2003

(65) Prior Publication Data

US 2004/0014746 A1 Jan. 22, 2004

Related U.S. Application Data

(60) Provisional application No. 60/354,598, filed on Feb. 5, 2002.
(51) Int. Cl.[7] .................... C07D 417/10; A61K 31/549; A61P 31/04; A61P 31/00
(52) U.S. Cl. ........................................ 514/222.5; 544/8
(58) Field of Search ........................... 544/8; 514/222.5

(56) References Cited

FOREIGN PATENT DOCUMENTS

| WO | WO 93/09103 | 5/1993 |
|----|-------------|--------|
| WO | WO 93/23384 | 11/1993 |
| WO | WO 94/13649 | 6/1994 |

*Primary Examiner*—Mark L. Berch
*Assistant Examiner*—Kahsay Habte
(74) *Attorney, Agent, or Firm*—Lucy X. Yang

(57) ABSTRACT

The present invention provides certain thiadiazinone derivatives of oxazolidinones of the following formula I:

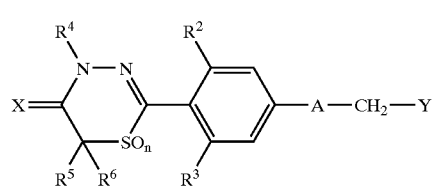

or pharmaceutically acceptable salts thereof that are antibacterial agents, pharmaceutical compositions containing them, methods for their use, and methods for preparing these compounds.

73 Claims, No Drawings

ANTIMICROBIAL THIADIAZINONE DERIVATIVES AND THEIR APPLICATION FOR TREATMENT OF BACTERIAL INFECTIONS

CROSS-REFERENCE TO RELATED APPLICATIONS

This application claims priority under 35 U.S.C. §119 to Provisional Application No. 60/354,598, filed in the United States on Feb. 5, 2002, the entire contents of which are hereby incorporated by reference.

FIELD OF THE INVENTION

The present invention relates to novel thiadiazinone derivatives of oxazolidinones, pharmaceutical compositions thereof, methods for their use, and methods for preparing the thiadiazinone derivatives. These compounds have potent activities against gram-positive and gram-negative bacteria.

BACKGROUND OF THE INVENTION

Due to ever-increasing antibiotic resistance, structurally novel antibacterials with a new mode of action have become increasingly important in the treatment of bacterial infections. Effective antibacterials should exhibit potent activity against a number of human and veterinary pathogens, including gram-positive aerobic bacteria such as multiply-resistant staphylococci and streptococci, anaerobic microorganisms such as bacteroides and clostridia species, and acid-fast microorganisms such as *Mycobacterium tuberculosis* and *Mycobacterium avium*.

Among newer antibacterial agents, oxazolidinone compounds are the most recent synthetic class of antimicrobials active against a number of pathogenic microorganisms. However, oxazolidinones generally do not demonstrate useful levels of activity against aerobic gram-negative microorganisms. Thus, the use of these oxazolidinone antibacterial agents is limited to infectious states caused by gram-positive bacteria.

Accordingly, it is among the objects of the present invention to provide pharmaceutical compounds that have broad antibacterial activity, including against gram-positive bacteria and gram-negative bacteria.

SUMMARY OF THE INVENTION

The present invention provides structurally novel pharmaceutical compounds with an expanded spectrum of antibacterial activity, including activity against gram-positive microorganisms and gram-negative microorganisms.

The present invention relates to a compound of the following formula I:

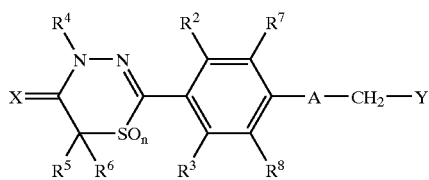

or a pharmaceutically acceptable salt thereof wherein:

A is a structure of the following formula i, ii, iii, or iv

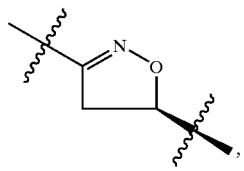

i

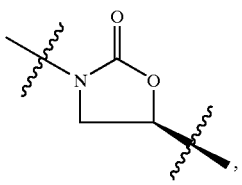

ii

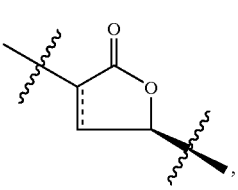

iii

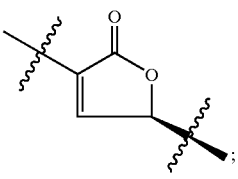

iv

X is O or S;
Y is
  (a) —NHC(=O)$R^1$,
  (b) —NHC(=S)$R^1$,
  (c) —NHC(=NCN)$R^1$,
  (d) —NH-$het^1$,
  (e) —O-$het^1$,
  (f) —S-$het^1$,
  (g) —$het^2$, or
  (h) —OH;
$R^1$ is
  (a) —H
  (b) —$NH_2$,
  (c) —NH$C_{1-4}$alkyl,
  (d) —$C_{1-4}$alkyl,
  (e) —$C_{2-4}$alkenyl,
  (f) —$C_{1-4}$heteroalkyl,
  (g) —$(CH_2)_mC(=O)C_{1-4}$alkyl,
  (h) —$OC_{1-4}$alkyl,
  (i) —$SC_{1-4}$alkyl,
  (j) —$(CH_2)_pC_{3-6}$cycloalkyl,
  (k) —$(CH_2)_rC(=O)$-aryl, or
  (l) —$(CH_2)_sC(=O)$-$het^1$;
$R^2$, $R^3$, $R^7$, and $R^8$ are independently
  (a) —H,
  (b) —Cl,
  (c) —F,
  (d) —$CH_3$,
  (e) —$NH_2$, or
  (f) —OH;
$R^4$ is
  (a) —H,
  (b) —$C_{1-4}$alkyl,
  (c) —$C_{1-4}$heteroalkyl, (d) —(CH$_2$)$_q$C(=O)OC$_{1-4}$alkyl,
(e) —(CH$_2$)$_m$C(=O)C$_{1-4}$alkyl,
(f) -aryl, or
(g) -het$^1$;

R$^5$ and R$^6$ are independently
(a) —H,
(b) —F,
(c) —C$_{1-4}$alkyl,
(d) —C$_{3-6}$cycloalkyl,
(e) —C$_{1-4}$heteroalkyl,
(f) -aryl,
(g) -het$^1$,
(h) —OC$_{1-4}$alkyl,
(i) —O(C=O) C$_{1-4}$alkyl,
(j) —O(C=O)OH,
(k) —(C=O)OC$_{1-4}$alkyl; or
(l) R$^5$ and R$^6$ taken together are C$_{3-6}$cycloalkyl; and m, n, p, q, r and s at each occurrence, is independently 0, 1, or 2.

The dotted line within structure iii indicates an optional double bond at that position.

The alkyl, alkenyl, or cycloalkyl groups at each occurrence above independently are optionally substituted with one, two, or three substituents selected from the group consisting of halo, aryl, het$^1$, and het$^2$. Het$^1$ at each occurrence is independently a C-linked 5 or 6 membered heterocyclic ring having 1 to 4 heteroatoms selected from the group consisting of oxygen, nitrogen, and sulfur within the ring. Het$^2$ at each occurrence is independently a N-linked 5 or 6 membered heterocyclic ring having 1 to 4 nitrogen and optionally having one oxygen or sulfur within the ring.

The compounds of formula I of the present invention exhibit an expanded spectrum of antibacterial activity, including activity against gram-positive microorganisms and gram-negative microorganisms, such as *Haemophilus influenzae* and *Moraxella catarrhalis*.

In another aspect, the present invention relates to a pharmaceutical composition comprising a compound of formula I, or a pharmaceutically acceptable salt thereof, and a pharmaceutically acceptable carrier.

In an additional aspect, the present invention provides a method for treating gram-positive microbial infections in humans or other warm-blooded animals by administering to the subject in need a therapeutically effective amount of a compound of formula I or a pharmaceutically acceptable salt thereof. The compound of formula I may be administered orally, parenterally, transdermally, topically, rectally, or intranasally.

In a further aspect, the present invention provides a method for treating gram-negative microbial infections in humans or other warm-blooded animals by administering to the subject in need a therapeutically effective amount of a compound of formula I or a pharmaceutically acceptable salt thereof. The compound of formula I may be administered orally, parenterally, transdermally, topically, rectally, or intranasally.

In yet another aspect, the present invention provides novel intermediates and processes for preparing compounds of formula I.

DETAILED DESCRIPTION OF THE INVENTION

Unless otherwise stated, the following terms used in the specification and claims have the meanings given below:

The carbon atom content of various hydrocarbon-containing moieties is indicated by a prefix designating the minimum and maximum number of carbon atoms in the moiety, i.e., the prefix C$_{i-j}$ indicates a moiety of the integer "i" to the integer "j" carbon atoms, inclusive. Thus, for example, C$_{1-7}$ alkyl refers to alkyl of one to seven carbon atoms, inclusive.

The terms alkyl, alkenyl, etc. refer to both straight and branched groups, but reference to an individual radical such as "propyl" embraces only the straight chain radical, a branched chain isomer such as "isopropyl" being specifically referred to. The alkyl, alkenyl, etc. group may be optionally substituted with one, two, or three substituents selected from the group consisting of halo, aryl, het$^1$, or het$^2$. Representative examples include, but are not limited to, difluoromethyl, 2-fluoroethyl, trifluoroethyl, —CH=CH-aryl, —CH=CH-het$^1$, —CH$_2$-phenyl, and the like.

The term "cycloalkyl" means a cyclic saturated monovalent hydrocarbon group of three to six carbon atoms, e.g., cyclopropyl, cyclohexyl, and the like. The cycloalkyl group may be optionally substituted with one, two, or three substituents selected from the group consisting of halo, aryl, het$^1$, or het$^2$.

The term "heteroalkyl" means an alkyl or cycloalkyl group, as defined above, having a substituent containing a heteroatom selected from N, O, or S(O)$_n$, where n is an integer from 0 to 2, including, hydroxy (OH), C$_{1-4}$alkoxy, amino, thio (—SH), and the like. Representative substituents include —NR$_a$R$_b$, —OR$_a$, or —S(O)$_n$ R$_c$, wherein R$_a$ is hydrogen, C$_{1-4}$alkyl, C$_{3-6}$cycloalkyl, optionally substituted aryl, optionally substituted heterocyclic, or —COR (where R is C$_{1-4}$alkyl); R$_b$ is hydrogen, C$_{1-4}$alkyl, —SO$_2$R (where R is C$_{1-4}$alkyl or C$_{1-4}$hydroxyalkyl), —SO$_2$NRR' (where R and R' are independently of each other hydrogen or C$_{1-4}$alkyl), —CONR'R" (where R' and R" are independently of each other hydrogen or C$_{1-4}$alkyl); n is an integer from 0 to 2; and R$_c$ is hydrogen, C$_{1-4}$alkyl, C$_{3-6}$cycloalkyl, optionally substituted aryl, or NR$_a$R$_b$ where R$_a$ and R$_b$ are as defined above. Representative examples include, but are not limited to 2-methoxyethyl (—CH$_2$CH$_2$OCH$_3$), 2-hydroxyethyl (—CH$_2$CH$_2$OH), hydroxymethyl (—CH$_2$OH), 2-aminoethyl (—CH$_2$CH$_2$NH$_2$), 2-dimethylaminoethyl (—CH$_2$CH$_2$NHCH$_3$), benzyloxymethyl, thiophen-2-ylthiomethyl, and the like.

The term "halo" refers to fluoro (F), chloro (Cl), bromo (Br), or iodo (I).

Aryl refers to phenyl, biphenyl, or naphthyl, optionally substituted with 1 to 3 substituents independently selected from halo, —C$_{1-4}$alkyl, —OH, —OC$_{1-4}$alkyl, —S(O)$_n$C$_{1-4}$alkyl wherein n is 0, 1, or 2, —C$_{1-4}$alkylNH$_2$, —NHC$_{1-4}$alkyl, —C(=O)H, or —C=N—OR$_d$ wherein R$_d$ is hydrogen or —C$_{1-4}$alkyl.

The term heterocyclic ring refers to an aromatic ring or a saturated or unsaturated ring that is not aromatic of 3 to 10 carbon atoms and 1 to 4 heteroatoms selected from the group consisting of oxygen, nitrogen, and S(O)$_n$ within the ring, where n is defined above. The heterocyclic ring may be optionally substituted with halo, —C$_{1-4}$alkyl, —OH, —OC$_{1-4}$alkyl, —S(O)$_n$C$_{1-4}$alkyl wherein n is 0, 1, or 2, —C$_{1-4}$alkylNH$_2$, —NHC$_{1-4}$alkyl, —C(=O)H, or —C=N—OR$_d$ wherein R$_d$ is hydrogen or C$_{1-4}$alkyl.

Examples of heterocylic rings include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isoxazolinone, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiadiazole tetrazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

Specifically, het$^1$ refers to a C-linked five- (5) or six- (6) membered heterocyclic ring. Representative examples of "het$^1$" include, but are not limited to, pyridine, thiophene, furan, pyrazole, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxaz-olyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,5-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, or 1,2,4-dithiazolone.

Specifically, het$^2$ refers to a N-linked five- (5) or six- (6) membered heterocyclic ring having 1 to 4 nitrogen atoms, and optionally having one oxygen or sulfur atom. Representative examples of "het$^2$" include, but are not limited to pyrrolyl, imidazolyl, pyrazolyl, 1,2,3-triazolyl, 1,2,4-triazolyl, 1,2,3,4-tetrazolyl, and isoxazolidinonyl group.

"Optional" or "optionally" means that the subsequently described event or circumstance may, but need not, occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the aryl group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Leaving group" has the meaning conventionally associated with it in synthetic organic chemistry, i.e., an atom or group capable of being displaced by a nucleophile and includes halogen, $C_{1-4}$alkylsulfonyloxy, ester, or amino such as chloro, bromo, iodo, mesyloxy, tosyloxy, trifluorosulfonyloxy, methoxy, N,O-dimethylhydroxylamino, and the like.

"Pro-drugs" mean any compound which releases an active parent drug according to a compound of the subject invention in vivo when such prodrug is administered to a mammalian subject. Prodrugs of a compound of the subject invention are prepared by modifying functional groups present in a compound of the subject invention in such a way that the modifications may be cleaved in vivo to release the parent compound. Prodrugs include compounds of the subject invention wherein a hydroxy, sulfhydryl or amino group in the compound is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of the subject invention, and the like.

The term "mammal" refers to all mammals including humans, livestock, and companion animals.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Illustrative Embodiments

Within the broadest definition of the present invention, certain compounds of the compounds of formula I may be preferred. Specific and preferred values listed below for radicals, substituents, and ranges, are for illustration only; they do not exclude other defined values or other values within defined ranges for the radicals and substituents.

In some preferred compounds of the present invention —$C_{1-4}$alkyl can be methyl, ethyl, propyl, isopropyl, butyl, iso-butyl, sec-butyl, and isomeric forms thereof.

In some preferred compounds of the present invention —$C_{2-4}$alkenyl can be vinyl, propenyl, allyl, butenyl, and isomeric forms thereof (including cis and trans isomers).

In some preferred compounds of the present invention —$C_{3-6}$cycloalkyl can be cyclopropyl, cyclobutyl, cyclopentyl, cyclohexyl, and isomeric forms thereof.

In some preferred compounds of the present invention —$C_{1-4}$ heteroalkyl can be hydroxymethyl, hydroxyethyl, and 2-methoxyethyl.

In some preferred compounds of the present invention halo can be fluoro (F) or chloro (Cl).

In some preferred compounds of the present invention $R^1$ can be —$C_{1-4}$alkyl, optionally substituted with one, two or three fluoro (F) or chloro (Cl).

In some preferred compounds of the present invention $R^1$ can be —H, —$CH_3$, —$CHF_2$, —$CF_3$, —$CHCl_2$, —$CH_2CF_3$, —$CH_2CH_3$, —$CH_2CHF_2$, or —$CH_2CH_2F$.

In some preferred compounds of the present invention $R^1$ can be —$CH_2OH$, —$CH_2CH_2OH$, or —$NH_2$.

In some preferred compounds of the present invention $R^1$ can be —CH=CH-aryl. Specifically, $R^1$ can be —CH=CH-het$^1$ or —CH=CH-het$^2$.

In some preferred compounds of the present invention $R^1$ can be —$CH_2C(=O)C_{1-4}$alkyl.

In some preferred compounds of the present invention $R^7$ and $R^8$ are both —H.

In some preferred compounds of the present invention $R^2$ and $R^3$ independently can be —H or —F.

In some preferred compounds of the present invention one of $R^2$ and $R^3$ is —H and the other is —F.

In some preferred compounds of the present invention X can be O or S.

In some preferred compounds of the present invention n can be 0.

In some preferred compounds of the present invention $R^4$, $R^5$ and $R^6$ can be —H.

In some preferred compounds of the present invention $R^2$ and $R^3$ independently can be —H or —F; and $R^4$, $R^5$, and $R^6$ can be —H.

In some preferred compounds of the present invention $R^4$ can be —H, —$C_{1-4}$alkyl, or —C(=O)O$C_{1-4}$alkyl.

In some preferred compounds of the present invention $R^5$ and $R^6$ independently can be —H, —$C_{1-4}$alkyl, —$C_{3-6}$cycloalkyl, or aryl.

In some preferred compounds of the present invention one of $R^5$ and $R^6$ is —H and the other is —$C_{1-4}$alkyl, —$C_{3-6}$cycloalkyl, or aryl.

In some preferred compounds of the present invention $R^5$ and $R^6$ taken together are —$C_{3-6}$cycloalkyl.

In some preferred compounds of the present invention -het$^1$ can be 2-pyridyl, 3-pyridyl, 4-pyridyl, 3-isoxazolyl, 4-isoxaz-olyl, 5-isoxaz-olyl, 1,2,3-triazol-1-yl, or 1,2,5-thiadiazol-3-yl group.

In some preferred compounds of the present invention -het$^2$ can be pyrrolyl, imidazolyl, pyrazolyl, 1,2,3-triazolyl, 1,2,4-triazolyl, 1,2,3,4-tetrazolyl, and isoxazolidinonyl group.

Some preferred compounds of the present invention are those wherein the structure i, ii, or iii has an optical configuration as depicted below:

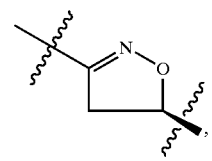
i

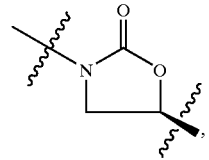
ii

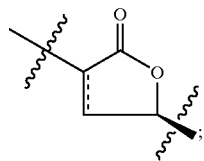
iii

The dotted line within structure iii indicates an optional double bond at that position. It will also be appreciated by those skilled in the art that compounds of the present invention may have additional chiral centers and be isolated in optically active and racemic forms. The present invention encompasses any racemic, optically active, tautomeric, or stereoisomeric form, or mixture thereof, of a compound of the invention.

One preferred group of compounds of the present invention are the compounds of the following formula II:

II

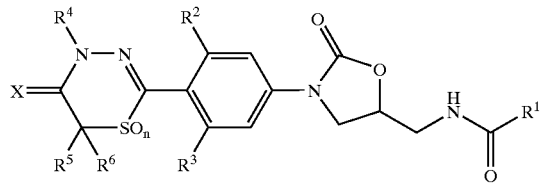

wherein $R^1$–$R^6$ and n are as defined previously for formula I.

Another preferred group of compounds of the present invention are the compounds of the following formula III

III

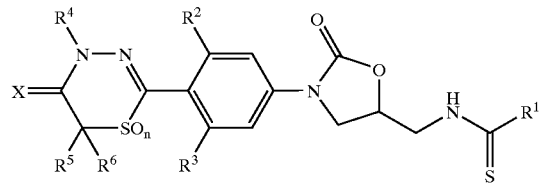

wherein $R^1$–$R^6$ and n are as defined previously for formula I.

An additional preferred group of compounds of the present invention are the compounds of the following formula IV

IV

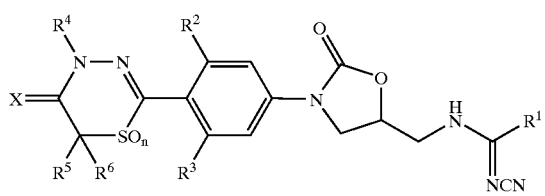

wherein $R^1$–$R^6$ and n are as defined previously for formula I.

A further preferred group of compounds of the present invention are the compounds of the following formula V

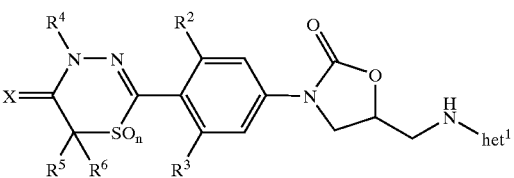

wherein $R^2$–$R^6$, n, and $het^1$ are as defined previously for formula I.

Another preferred group of compounds of the present invention are the compounds of the following formula VI

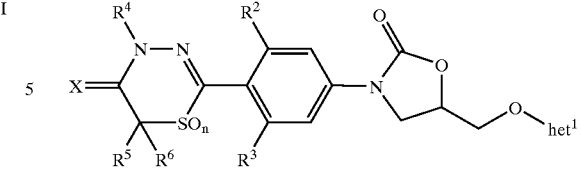

wherein $R^2$–$R^6$, n, and $het^1$ are as defined previously for formula I.

An additional preferred group of compounds of the present invention are the compounds of the following formula VII

VII

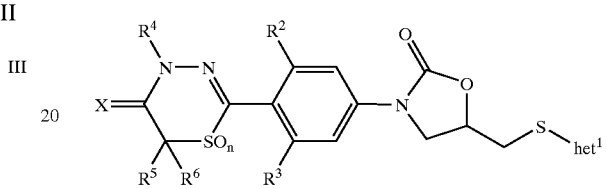

wherein $R^2$–$R^6$, n, and $het^1$ are as defined previously for formula I.

A further preferred group of compounds of the present invention are the compounds of the following formula VIII:

VIII

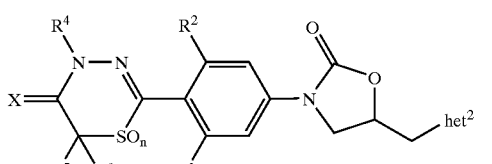

wherein $R^2$–$R^6$, n, and $het^2$ are as defined previously for formula I.

A particularly preferred group of compounds includes the following compounds:

(a) N-{3-[3-fluoro-4-(5-oxo-5,6-dihydro-4H-[1,3,4] thiadiazin-2-yl)-phenyl]-2-oxo-oxazolidin-5(S)-ylmethyl}-acetamide;

(b) N-{3-[3-fluoro-4-(6(S)-methyl-5-oxo-5,6-dihydro-4H-[1,3,4]thiadiazin 2-yl)-phenyl]-2-oxo-oxazolidin-5 (S)-ylmethyl}-acetamide;

(c) N-{3-[3-fluoro-4-(6(R)-methyl-5-oxo-5,6-dihydro-4H-[1,3,4]thiadiazin 2-yl)-phenyl]-2-oxo-oxazolidin-5 (S)-ylmethyl}-acetamide;

(d) N-{3-[3-fluoro-4-(5-oxo-5,6-dihydro-4H-[1,3,4] thiadiazin-2-yl)-phenyl 2-oxo-oxazolidin-5(S)-ylmethyl}-propionamide;

(e) cyclopropanecarboxylic acid {3-[3-fluoro-4-(5-oxo-5, 6-dihydro-4H-[1,3,4]thiadiazin-2-yl)-phenyl]-2-oxo-oxazolidin-5 (S)-ylmethyl}-amide;

(f) {3-[3-fluoro-4-(5-oxo-5,6-dihydro-4H-[1,3,4] thiadiazin-2-yl)-phenyl]-2-oxo-oxazolidin-5(S)-ylmethyl}-urea;

(g) N-{3-[3-fluoro-4-(5-oxo-5,6-dihydro-4H-[1,3,4] thiadiazin-2-yl)-phenyl]-2-oxo-oxazolidin-5(S)-ylmethyl}-carbamic acid methyl ester;

(h) N-{3-[3-fluoro-4-(5-oxo-5,6-dihydro-4H-[1,3,4] thiadiazin-2-yl)-phenyl]-2-oxo-oxazolidin-5(S)-ylmethyl}-thioacetamide;

(i) N-{3-[3-fluoro-4-(5-thioxo-5,6-dihydro-4H-[1,3,4]thiadiazin-2-yl)-phenyl]-2-oxo-oxazolidin-5(S)-ylmethyl}-thioacetamide;

(j) N-{3-[3-fluoro-4-(5-thioxo-5,6-dihydro-4H-[1,3,4]thiadiazin-2-yl)-phenyl]-2-oxo-oxazolidin-5(S)-ylmethyl}-acetamide;

(k) 2-[2-fluoro-4-(5(R)-hydroxymethyl)-2-oxo-oxazolidin-3-yl)-phenyl]-4H-[1,3,4]thiadiazin-5-one;

(l) 2-{2-fluoro-4-[5(S)-(isoxazol-3-ylaminomethyl)-2-oxo-oxazolidin-3-yl phenyl}-4H-[1,3,4]thiadiazin-5-one;

(m) 2-{2-fluoro-4-[5(S)-(isoxazol-3-yloxymethyl)-2-oxo-oxazolidin-3-yl]-phenyl}-4H-[1,3,4]thiadiazin-5-one; and (n) N-{3-[3-fluoro-4-(5-oxo-5,6-dihydro-4H-[1,3,4]thiadiazin-2-yl)-phenyl]-2-oxo-oxazolidin-5-ylmethyl}-3-(4-hydroxyphenyl)-acrylamide.

Additional preferred compounds include the following compounds:

(a) N-{3-[4-(6,6-dimethyl-5-oxo-5,6-dihydro-4H-[1,3,4]thiadiazin-2-yl)-3-fluorophenyl]-2-oxo-oxazolidin-5(S)-ylmethyl}-acetamide;

(b) N-{3-[3-fluoro-4-(6-ethyl-5-oxo-5,6-dihydro-4H-[1,3,4]thiadiazin-2-yl)-phenyl]-2-oxo-oxazolidin-5(S)-ylmethyl}-acetamide;

(c) N-{3-[3-fluoro-4-(9-oxo-5-thia-7,8-diazaspiro[3.5]non-6-en-6-yl)-phenyl]-2-oxo-oxazolidin-5(S)-ylmethyl}-acetamide;

(d) N-{3-[3-fluoro-4-(5-oxo-6-phenyl-5,6-dihydro-4H-[1,3,4]thiadiazin-2-yl)-phenyl]-2-oxo-oxazolidin-5(S)-ylmethyl}-acetamide;

(e) N-{3-[3-fluoro-4-(5-oxo-5,6-dihydro-4H-[1,3,4]thiadiazin-2-yl)-phenyl]-2-oxo-oxazolidin-5 (S)-ylmethyl}-2-hydroxyacetamide;

(f) N-{3-[3-fluoro-4-(5-oxo-5,6-dihydro-4H-[1,3,4]thiadiazin-2-yl)-phenyl]-2-oxo-oxazolidin-5(S)-ylmethyl}-carbamic acid tert-butyl ester;

(g) N-{3-[3-fluoro-4-(5-oxo-5,6-dihydro-4H-[1,3,4]thiadiazin-2-yl)-phenyl]-2-oxo-oxazolidin-5(S)-ylmethyl}-3-oxo-butyramide;

(h) N-{3-[3-fluoro-4-(5-oxo-5,6-dihydro-4H-[1,3,4]thiadiazin-2-yl)-phenyl]-2-oxo-oxazolidin-5(S)-ylmethyl}-3-(4-fluorophenyl)-3-oxo-propionamide;

(i) N-{3-[3-fluoro-4-(5-oxo-5,6-dihydro-4H-[1,3,4]thiadiazin-2-yl)-phenyl]-2-oxo-oxazolidin-5(S)-ylmethyl}-3-[4-(hydroxyimino-methyl)-phenyl]-acrylamide;

(j) N-{3-[3-fluoro-4-(5-oxo-5,6-dihydro-4H-[1,3,4]thiadiazin-2-yl)-phenyl]-2-oxo-oxazolidin-5(S)-ylmethyl}-3-[4-(methoxyimino-methyl)-phenyl]-acrylamide;

(k) N-{3-[4-(6,6-dimethyl-1,1,5-trioxo-1,4,5,6-tetrahydro-1$\lambda^6$-[1,3,4]thia-diazine-2-yl)-3-fluorophenyl]-2-oxo-oxazolidin-5(S)-ylmethyl}acetamide;

(l) N-{3-[3-fluoro-4-(4-methyl-5-oxo-5,6-dihydro-4H-[1,3,4]thiadiazin-2-yl)-phenyl]-2-oxo-oxazolidin-5(S)-ylmethyl}-acetamide; and (m) phosphoric acid mono-{4-[2-({3-[3-fluoro-4-(5-oxo-5,6-dihydro-4H-[1,3,4]thiadiazin-2-yl)-phenyl]-2-oxo-oxazolidin-5-ylmethyl}-carbamoyl)-vinyl]-phenyl}ester.

Further preferred compounds include the following compounds:

(a) N-{3-[3-fluoro-4-(5-oxo-6-propyl-5,6-dihydro-4H-[1,3,4]thiadiazin-2-yl)-phenyl]-2-oxo-oxazolidin-5(S)-ylmethyl}-acetamide;

(b) N-{3-[3-fluoro-4-(6-isopropyl-5-oxo-5,6-dihydro-4H-[1,3,4]thiadiazin-2-yl)-phenyl]-2-oxo-oxazolidin-5(S)-ylmethyl}-acetamide;

(c) N-{3-[3-fluoro-4-(6-fluoro-5-oxo-5,6-dihydro-4H-[1,3,4]thiadiazin-2-yl)-phenyl]-2-oxo-oxazolidin-5(S)-ylmethyl}-acetamide;

(d) N-{3-[3-fluoro-4-(6-hydroxymethyl-5-oxo-5,6-dihydro-4H-[1,3,4]thiadiazin-2-yl)-phenyl]-2-oxo-oxazolidin-5(S)-ylmethyl}-acetamide;

(e) N-{3-[3-fluoro-4-(6-(2-hydroxyethyl)-5-oxo-5,6-dihydro-4H-[1,3,4]thiadiazin-2-yl)-phenyl]-2-oxo-oxazolidin-5(S)-ylmethyl}-acetamide;

(f) 2-{4-[5(S)-(acetylaminomethyl)-2-oxo-oxazolidin-3-yl]-2-fluorophenyl}-5-oxo-5,6-dihydro-4H-[1,3,4]thiadiazine-6-carboxylic acid methyl ester;

(g) N-(3-{3-fluoro-4-(6-(4-hydroxyphenyl)-5-oxo-5,6-dihydro-4H-[1,3,4]thiadiazin-2-yl]-phenyl}-2-oxo-oxazolidin-5(S)-ylmethyl)-acetamide;

(h) N-{3-[3-fluoro-4-(5-thioxo-5,6-dihydro-4H-[1,3,4]thiadiazin-2-yl)-phenyl]-2-oxo-oxazolidin-5(S)-ylmethyl}-carbamic acid tert-butyl ester;

(i) N-{3-[4-(6,6-dimethyl-1,5-dioxo-1,4,5,6-tetrahydro-1$\lambda^4$-[1,3,4]-thiadiazin-2-yl)-3-fluorophenyl]-2-oxo-oxazolidin-5(S)-ylmethyl}-acetamide;

(j) acetic acid 2-{4-[5(S)-(acetylaminomethyl)-2-oxo-oxazolidin-3-yl]-2-fluorophenyl}-5-oxo-5,6-dihydro-4H-[1,3,4]thiadiazin-6-yl ester; and (k) (2-{4-[5(S)-(acetylaminomethyl)-2-oxo-oxazolidin-3-yl]-2-fluorophenyl}-5-oxo-5,6-dihydro-[1,3,4]thiadiazin-4-yl)-acetic acid methyl ester.

General Synthetic Schemes

The compounds of this invention can be prepared in accordance with one or more of the Schemes discussed below. Syntheses of thiadiazinones are precedented in the prior art, although no antimicrobial thiadiazinone compounds have been reported. Thus, thiadiazinone compounds with cardiotonic properties have been prepared from ethyl bromoacetate with thioarylhydrazides in presence of aqueous sodium hydroxide as described by Brown, et al. in U.S. Pat. No. 4,489,074 incorporated herein by reference. It should be noted, however, that the above protocol has limited application due to the use of a strong base (3N aqueous sodium hydroxide). Importantly, it is not applicable for a synthesis of amide and carbamate derivatives (such as oxazolidinone compounds described herein) that can react with the strong aqueous bases. According to the subject invention, a new and convenient stepwise protocol useful for preparation of antimicrobial thiadiazinones has been developed.

Scheme 1 below serves to illustrate one general synthesis of thiadiazinone derivatives bearing an oxazolidinone group.

Scheme 1.
Synthesis of thiadiazine derivatives.

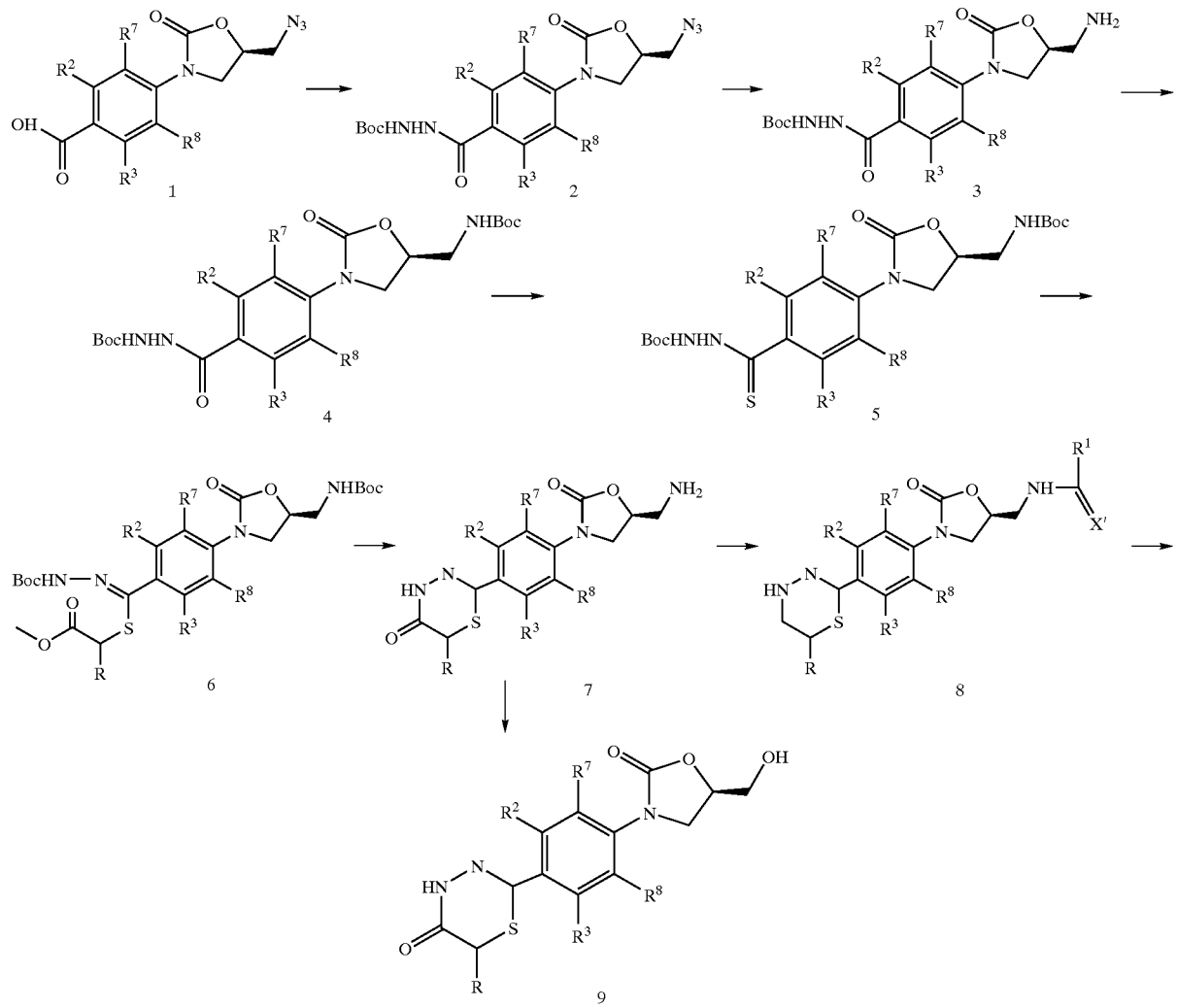

where X'=O, S and R, $R^1$, $R^2$, $R^3$, $R^7$ and $R^8$ are as defined herein.

First, a benzene carboxylic acid reagent, compound 1, (such as oxazolidinone derivative of Scheme 1 prepared as described by Gordeev et al. in U.S. Pat. No. 6,239,152) is coupled with a suitable N-protected hydrazine reagent, such as N-(tert-butoxycarbonyl)hydrazine. This reaction can be performed with any number of known coupling reagents, such as HATU, HOBt, or carbodiimides. The coupling reaction is typically performed in a polar aprotic solvent, such as dimethylformamide, acetonitrile, or mixtures thereof, in presence of an organic base, such as triethylamine or (N,N-diisopropyl)ethylamine (DIEA). The process is typically carried out between about 0° C. to about 50° C. for a period of time sufficient to provide for the Boc-protected hydrazine derivative, compound 2.

Next, the 5-azidomethyl group of compound 2 is reduced into the amine functionality of compound 3. This transformation can be performed by a phosphine reduction using, e.g., triphenylphosphine in a polar organic solvent, such as tetrahydrofuran with added water (the water may be optionally added after the azide is allowed to react first with triphenylphosphine). The reaction is typically performed at temperatures in a range of from about 25° C. to about 70° C. Optionally, the azide can be reduced using a catalytic hydrogenation (e.g., with hydrogen in presence of a Pd catalyst, such as 5–10% Pd on carbon).

The 5-aminomethyl group of compound 3 is then protected (e.g., as a Boc-derivative as shown in Scheme 1) to provide for compound 4. This protection may be conducted in a suitable organic solvent in the presence of an organic base such as pyridine. The amine protection is then followed by a conversion of the hydrazide into thiohydrazide, compound 5, with a Lawesson's reagent. This conversion may be conducted in suitable organic solvent, such as dioxane or tetrahydrofuran, and is typically performed at temperatures in a range of from about 25° C. to about 100° C. Both the amine protection reaction and the conversion reaction using Lawesson's reagent are performed under conditions well precedented in the chemical literature. By way of example, Lawesson's chemistry was reviewed by Cava et al. in Tetrahedron, 1985, vol. 41, pp. 5061–5087.

The next step involves an alkylation of the resulting protected thiohydrazide reagent, compound 5, with a suitable alpha-substituted ester reagent (such as methyl or ethyl ester) to provide for compound 6. The ester bears a good leaving group in a position alpha to the ester functionality, e.g., bromo, iodo, nitrobenzenesulfonyloxy, mesyloxy (OMs), or a like group. The reaction is typically performed in a polar organic solvent such as acetonitrile, tetrahydrofuran, or dimethylformamide in the presence of an organic or inorganic base, such as potassium carbonate, pyridine, or triethylamine. A typical range of temperatures for this transformation is from about 0° C. to about 50° C.

The following step involves deprotection of an acid-sensitive thiohydrazide protective group of compound 6 (exemplified by Boc in Scheme 1) to provide for compound 7. Under reaction conditions, the acid-induced N-deprotection is immediately followed by a high-yielding heterocyclization into the desired thiadiazinone derivative. This transformation of Scheme 1 is conveniently performed in presence of organic or inorganic acids, such as trifluoroacetic acid or hydrogen chloride. The reaction is carried out in organic solvent, such as dichloromethane, dichloroethane, dioxane, or tetrahydrofuran, at temperatures in a range from about 10° C. to about 60° C. When the starting material has an acid-sensitive protected 5-aminomethyl group (as exemplified in Scheme 1), the resulted thiadiazinone product, compound 7, bears the unprotected amine functionality conveniently suitable for subsequent transformations.

Thus, the 5-aminomethyl group of compound 7 can be acylated or thioacylated using reactions well known in the art to provide for compound 8. In this way, acylations may be performed by reactions of the amines with carboxylic acid anhydrides or esters. These transformations are generally performed at 0° C. to 50° C. using polar solvents, such as acetonitrile, dimethylformamide, tetrahydrofuran, and methanol or mixtures thereof with optional apolar solvents, such as dichloromethane. These reactions are preferably conducted in presence of an organic or inorganic base, such as pyridine, triethylamine, or potassium carbonate. Thioacylations are prepared by allowing amine intermediates to react with dithioesters or thionoesters and a tertiary amine base such as triethylamine. In this reaction it is often convenient to employ an excess of the tertiary amine base with an amine salt prepared by Boc deprotection in step 2 without first isolating the free base. Solvents such as tetrahydrofuran, methylene chloride or preferably methanol, and temperatures in the range of about 24° C. to about 50° C. may be used for this reaction. Other thiocarbonyl compounds of the Scheme 1 can be prepared according to procedures as disclosed in PCT International Publication WO 98/54161, herein incorporated by reference in its entirety.

Optionally, the 5-aminomethyl group can be converted into a hydroxyl group using reactions well known in the art to provide for compound 9. For example, this conversion may be achieved via a diazotization of an amine with a nitrous acid source (such as tert-butyl nitrite in presence of acetic acid) followed by a treatment with an aqueous base, such as lithium hydroxide.

If desired, the above thiadiazinone compounds can be N-alkylated as exemplified in below in Scheme 2. This transformation may be achieved starting with compound 8a (where X=O and R'=CH3) for compound 8 and using any number of typical alkylating reagents, such as alkyl halides ($R^4X$) or alkyl triflates in presence of an organic or inorganic base, such as potassium carbonate, triethylamine, or pyridine. The reaction is typically conducted in a polar organic solvent, such as dimethylformamide or acetonitrile, at temperatures from about 0° C. to about 50° C., to provide for compound 10.

Scheme 2.
Synthesis of 4-substituted thiadiazine derivatives.

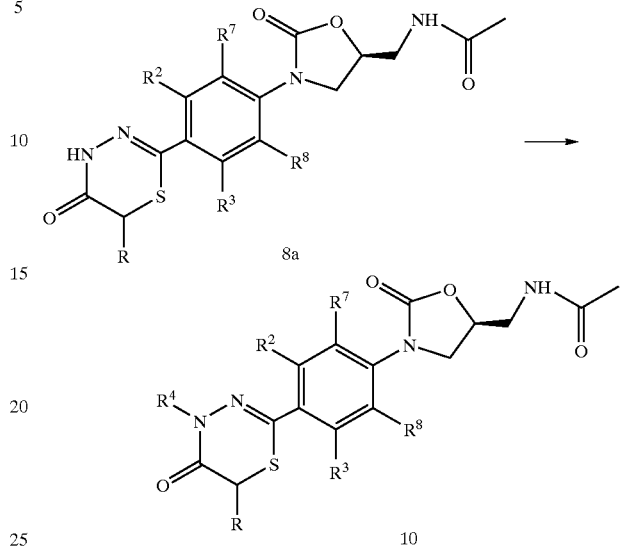

Optionally, thiadiazinone compounds can be further converted into thiadiazinone S-oxide and/or S-dioxide derivatives as exemplified below in Scheme 3. Peracids, alkyl hydroperoxides, and hydrogen peroxide are all suitable oxidizing agents. The reaction is typically performed in organic solvent, such as acetic acid, at temperatures from about 25° C. to about 100° C. If the reaction is carried out in aqueous acetic acid or other acidic reagents, Pummerer rearrangement products are possible.

Scheme 3.
Synthesis of 4-substituted thiadiazine derivatives.

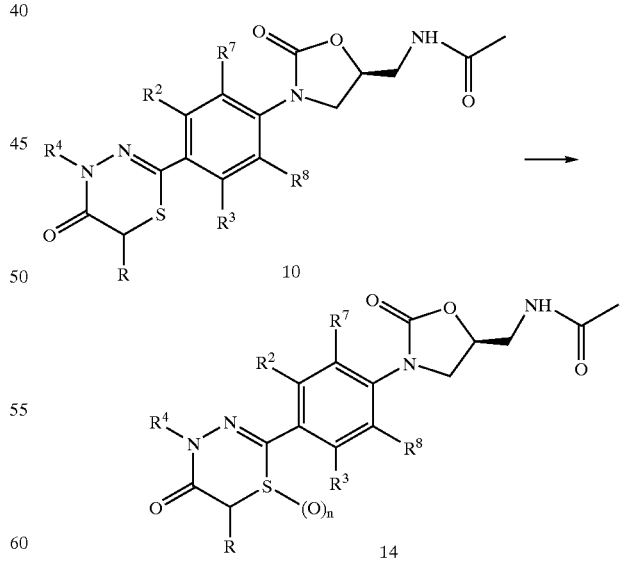

Optionally, thiadiazinone compounds can be converted into antimicrobial thiadiazinethione derivatives as exemplified below in Scheme 4. This reaction is performed under conditions described for a traditional Lawesson's thionation chemistry (see, e.g., Cava et al. in Tetrahedron, 1985, vol.

41, pp. 5061–5087). The reaction is typically performed in organic solvent, such as dioxane or tetrahydrofuran, at temperatures from about 25° C. to about 100° C. whereupon compound 8b (X and X'=O) is converted to compound 11.

Scheme 4.
Synthesis of thiadiazanone derivatives.

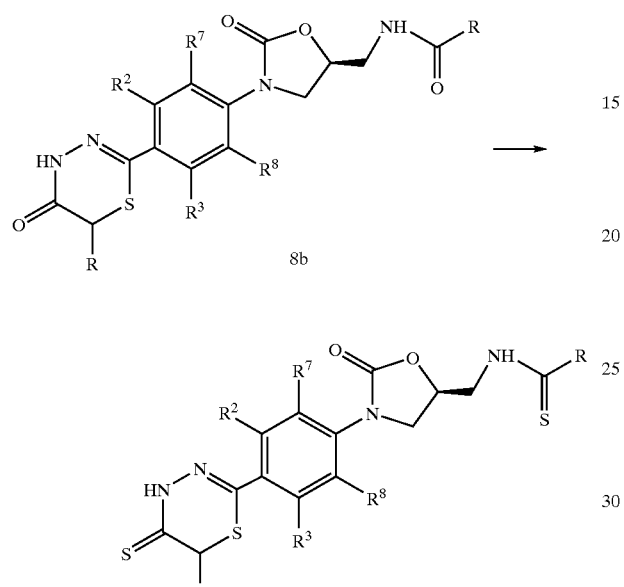

Alcohol thiadiazinone derivatives of Scheme 1, compound 9, can be further converted into heteroaryl amine (or heteroarylether) analogs using chemistry described for non-thiadiazinone compounds by Perova et al. in Zh. Org. Khim., 1994, vol. 30, pp. 1660–1663. It should be further noted that no thiadiazinone or thiadiazinethione compounds have been disclosed in the aforementioned publication. One example of such transformation is provided in Scheme 5 below. In this example the alcohol thiadiazinone derivative is coupled with an appropriate amino-isoxazole or hydroxy-isoxazole, for example, compound 9, 3-(2,2,2-trichloro-ethoxycarbonylamino)isoxazole [prepared according to the procedure found in WO 00/21960] or 3-hydroxyisoxazole. This reaction can be performed with a suitable coupling reagent, such as diisopropyl azodicarboxylate (DIAD). The coupling reaction is typically performed in a polar aprotic solvent, such as dimethylformamide, acetonitrile, tetrahydrofuran, or mixtures thereof, in the presence of an organic base, such as triphenylphosphine. The process is typically carried out at about 0° C. to about 50° C.

When coupling to an amino-isoxazole, the resulting carbamic acid of compound 12 can then be reduced to the heteroaryl amine of compound 13. This reduction may be achieved with any number of typical reducing agents, such as zinc in the presence of an organic or inorganic acid, such as acetic acid or hydrochloric acid.

Scheme 5.
Synthesis of thiadiazanone derivatives with 5(S)-isoazolylaminomethyloxazolidinone group.

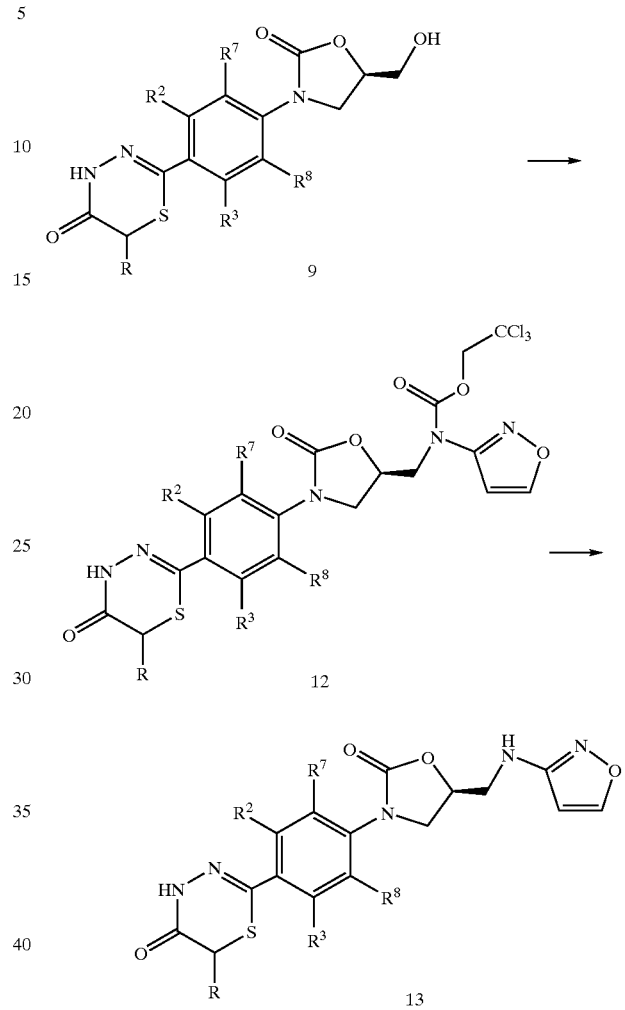

The 6-oxy substituted derivatives, compound 16, can be produced by a Pummerer reaction of the parent thiadiazinone, compound 8b, in an acylating agent, such as acetic anhydride, in the presence of an oxidant, such as hydrogen peroxide as shown in Scheme 6 below. Optionally, an intermediate S-oxide can be isolated and then treated with an acylating agent. This treatment with the acylating agent can occur with or without base and with optional heating at 40° C. to 60° C. for 1 hour.

Scheme 6.
Synthesis of 6-oxythiadiazine derivatives.

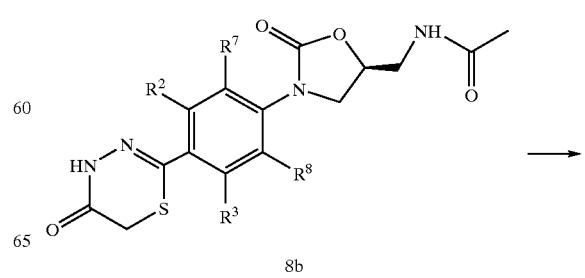

-continued

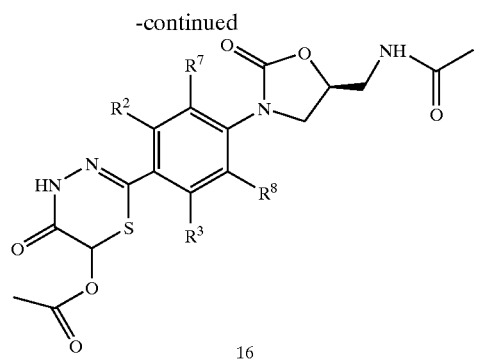

16

Compounds where A is chosen from formulas i, iii, or iv can be prepared using the methods described herein above substituting the appropriate starting materials.

Utility and Testing

The compounds of the subject invention exhibit potent activities against a variety of microorganisms, including gram positive and gram negative microorganisms. Accordingly, the compounds of the subject invention have broad antibacterial activity. Thus, the compounds of the present invention are useful antimicrobial agents and may be effective against a number of human and veterinary pathogens, including gram positive aerobic bacteria such as multiply-resistant staphylococci and streptococci, Gram negative microorganisms such as *H. influenzae* and *M catarrahlis*, as well as anaerobic microorganisms such as bacteroides and clostridia species, and acid-fast microorganisms such as *Mycobacterium tuberculosis* and *Mycobacterium avium*.

The in vitro activity of compounds of the subject invention may be assessed by standard testing procedures such as the determination of minimum inhibitory concentration (MIC) by agar dilution as described in "Approved Standard. Methods for Dilution Antimicrobial Susceptibility Tests for Bacteria that Grow Aerobically," $3^{rd}$ ed., published 1993 by the National Committee for Clinical Laboratory standards, Villanova, Pa., USA.

The in vitro MICs of test compounds may be determined by a standard agar dilution method. A stock drug solution of each analog is prepared in a preferred solvent, usually DMSO:$H_2O$ (1:3). Serial 2-fold dilutions of each sample are made using 1.0 ml aliquots of sterile distilled water. To each 1.0 ml aliquot of drug is added 9 ml of molten Mueller Hinton agar medium. The drug-supplemented agar is mixed, poured into 15×100 mm petri dishes, and allowed to solidify and dry prior to inoculation.

Vials of each of the test microorganisms are maintained frozen in the vapor phase of a liquid nitrogen freezer. Test cultures are grown overnight at 35° C. on the medium appropriate for the microorganism. Colonies are harvested with a sterile swab, and cell suspensions are prepared in Trypticase Soy broth (TSB) to equal the turbidity of a 0.5 McFarland standard. A 1:20 dilution of each suspension is made in TSB. The plates containing the drug supplemented agar are inoculated with a 0.001 ml drop of the cell suspension using a Steers replicator, yielding approximately $10^4$ to $10^5$ cells per spot. The plates are incubated overnight at 35° C.

Following incubation the Minimum Inhibitory Concentration (MIC $\mu$g/ml), the lowest concentration of drug that inhibits visible growth of the microorganism, is read and recorded. The data is shown in Table I.

TABLE I

Antimicrobial activity of selected compounds

| Example # | *S. pneumoniae* UC9912 MIC, $\mu$g/mL | *S. aureus* UC9213 MIC, $\mu$g/mL | *H. influenzae* 30063 MIC, $\mu$g/mL |
|---|---|---|---|
| 1 | <0.06 | 0.5 | 1 |
| 2 | 0.25 | 1 | 4 |
| 3 | 0.25 | 1 | 4 |
| 4 | 0.25 | 2 | 16 |
| 5 | 2 | 4 | 32 |
| 8 | 0.5 | 2 | 32 |
| 9 | 0.5 | 4 | 16 |
| 15 | <0.06 | 1 | 2 |
| 16 | 0.125 | 2 | 2 |
| 17 | 0.125 | 2 | 4 |
| 18 | 0.125 | 2 | 4 |
| 19 | 0.125 | 1 | 4 |
| 20 | 2 | 2 | 64 |
| 21 | 0.5 | 4 | 8 |
| 22 | 1 | 4 | 16 |
| 23 | 0.25 | 1 | 8 |
| 24 | 0.06 | 1 | >64 |
| 25 | <0.06 | 0.125 | 0.5 |
| 26 | <0.06 | 0.25 | 1 |
| 32 | 0.5 | 2 | 16 |
| 34 | 0.25 | 0.125 | 1 |

Administration and Pharmaceutical Formulations

In general, the compounds of the subject invention will be administered in a therapeutically effective amount by any of the accepted modes of administration for agents that serve similar utilities. By way of example, the compounds of the subject invention may be administered orally, parenterally, transdermally, topically, rectally, or intranasally. The actual amount of the compound of the subject invention, i.e., the active ingredient, will depend on a number of factors, such as the severity of the disease, i.e., the infection, to be treated, the age and relative health of the subject, the potency of the compound used, the route and form of administration, and other actors, all of which are within the purview of the attending clinician.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

When employed as pharmaceuticals, the compounds of the subject invention are usually administered in the form of pharmaceutical compositions. These compounds can be administered by a variety of routes including oral, parenteral, transdermal, topical, rectal, and intranasal.

These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of the subject invention above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The quantity of active component, that is the compound according to the subject invention, in the pharmaceutical composition and unit dosage form thereof may be varied or adjusted widely depending upon the particular application, the potency of the particular compound and the desired concentration.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of the subject invention above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically or therapeutically effective amount. It, will be understood, however, that the amount of the compound actually administered will be determined by a physician, in the light of the relevant circumstances, including the condition to be treated, the severity of the bacterial infection being treated, the chosen route of administration, the actual compound administered, the age, weight, and response of the individual patient, the severity of the patient's symptoms, and the like.

In therapeutic use for treating, or combating, bacterial infections in warm-blooded animals, the compounds or pharmaceutical compositions thereof will be administered orally, topically, transdermally, and/or parenterally at a dosage to obtain and maintain a concentration, that is, an amount, or blood-level of active component in the animal undergoing treatment which will be antibacterially effective. Generally, such antibacterially or therapeutically effective amount of dosage of active component (i.e., an effective dosage) will be in the range of about 0.1 to about 100, more preferably about 1.0 to about 50 mg/kg of body weight/day.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure-breathing machine. Solution, suspension, or powder compositions may be administered, preferably orally or nasally, from devices that deliver the formulation in an appropriate manner.

The following formulation examples illustrate representative pharmaceutical compositions of the present invention.

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9

A subcutaneous formulation may be prepared as follows:

| Ingredient | Quantity |
| --- | --- |
| Active Ingredient | 5.0 mg |
| Corn Oil | 1.0 mL |

Formulation Example 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions that can transiently open the blood-brain barrier.

Other suitable formulations for use in the present invention can be found in *Remington's Pharmaceutical Sciences*, Mace Publishing Company, Philadelphia, Pa., 17th ed. (1985).

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 and 8. It will be understood that use of certain of the foregoing excipients, carriers, or stabilizers will result in the formation of pharmaceutical salts.

The following synthetic and biological examples are offered to illustrate this invention and are not to be construed in any way as limiting the scope of this invention.

EXAMPLES

In the discussion above and in the examples below, the following abbreviations have the following meanings. If an abbreviation is not defined, it has its generally accepted meaning.

| | |
| --- | --- |
| Boc = | tert-butoxycarbonyl |
| bs = | broad singlet |
| dd = | doublet of doublets |
| DCM = | dichloromethane |
| DMF = | dimethylformamide |
| DMSO = | dimethyl sulfoxide |
| g = | grams |
| $^1$HNMR = | proton nuclear magnetic resonance |
| h = | hours |
| HPLC = | high pressure liquid chromatography |
| Hz = | hertz |
| m = | multiplet |
| M = | molar |
| mg = | milligram |
| ml = | milliliter |
| mm = | millimeter |
| mmol = | millimol |
| mp = | melting point |
| MS = | mass spectrometry |
| MHz = | megahertz |
| N = | normal |
| s = | singlet |

| | |
|---|---|
| t = | triplet |
| TFA = | trifluoroacetic acid |
| THF = | tetrahydrofuran |
| PTLC = | preparative thin layer chromatography |

All of the starting materials used in the synthesis of the compounds of the present invention are known compounds some of which are commercially available from at least one or more of the following companies: Aldrich, Fluka, Lancaster, Sigma, Chemservice, Bachem, Maybridge, NovaBiochem, Alfa and TCI. Additionally, the term "Aldrich" indicates that the compound or reagent used in the following procedures is commercially available from Aldrich Chemical Company, Inc., 1001 West Saint Paul Avenue, Milwaukee, Wis. 53233 USA; the term "Fluka" indicates that the compound or reagent is commercially available from Fluka Chemical Corp., 980 South 2nd Street, Ronkonkoma N.Y. 11779 USA; the term "Lancaster" indicates that the compound or reagent is commercially available from Lancaster Synthesis, Inc., P.O. Box 100 Windham, N.H. 03087 USA; the term "Sigma" indicates that the compound or reagent is commercially available from Sigma, P.O. Box 14508, St. Louis Mo. 63178 USA; the term "Chemservice" indicates that the compound or reagent is commercially available from Chemservice Inc., Westchester, Pa., USA; the term "Bachem" indicates that the compound or reagent is commercially available from Bachem Bioscience Inc., 3700 Horizon Drive, Renaissance at Gulph Mills, King of Prussia, Pa. 19406 USA; the term "Maybridge" indicates that the compound or reagent is commercially available from Maybridge Chemical Co. Trevillett, Tintagel, Cornwall PL34 OHW United Kingdom; and the term "TCI" indicates that the compound or reagent is commercially available from TCI America, 9211 North Harborgate St., Portland, Oreg., 97203, OR., USA; the term "Alfa" indicates that the compound or reagent is commercially available from Johnson Matthey Catalog Company, Inc. 30 Bond Street, Ward Hill, Mass. 01835-0747; and the term "Nova Biochem" indicates that the compound or reagent is commercially available from NovaBiochem USA, 10933 North Torrey Pines Road, P.O. Box 12087, La Jolla Calif. 92039-2087.

In the examples below, all temperatures are in degrees Celsius (unless otherwise indicated) and the following general procedures are used to prepared the compounds as indicated.

Example 1
N-{3-[3-Fluoro-4-(5-oxo-5,6-dihydro-4H-[1,3,4]thiadiazin-2-yl)-phenyl]-2-oxo-oxazolidin-5(S)-ylmethyl}-acetamide

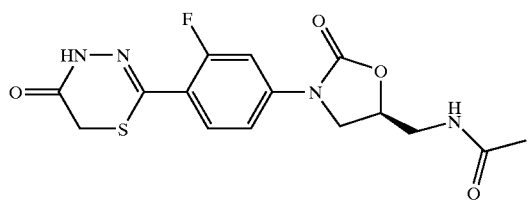

2-[4-(5(S)-Aminomethyl-2-oxo-oxazolidin-3-yl)-2-fluorophenyl]-4H-[1,3,4]thiadiazin-5-one (0.100 g, 0.308 mmol) is dissolved in pyridine (2 ml) and acetic anhydride (0.032 ml, 0.339 mmol) is added. The reaction is stirred at room temperature for 4 hours and then evaporated to dryness. The residue is purified by PTLC (10% MeOH/DCM) to give pure product as a white solid (0.086 g, 76%); $^1$HNMR (300 MHz, DMSO-d$_6$) δ 1.82 (s, 3H), 3.41 (t, J=5.5, 2H), 3.59 (s, 2H), 3.76 (dd, J=6.6, 9.1, 2H), 4.14 (t, J=9.1 Hz, 1H), 4.71–4.79 (m, 1H), 7.42 (dd, J=2.2, 8.5 Hz, 1H), 7.58 (dd, J=2.2, 14, 1H), 7.69 (t, J=8.5, 1H), 8.25 (t, J=5.8 Hz, 1H), 11.6 (s, 1H); R$_f$ (10% MeOH/DCM)=0.52; mp 206–9; MS (m/z): [M+H]$^+$=367.

The intermediates for this compound are prepared as follows:

I. 2-[4-(5(S)-Aminomethyl-2-oxo-oxazolidin-3-yl)-2-fluorophenyl]-4H-[1,3,4]thiadiazin-5-one

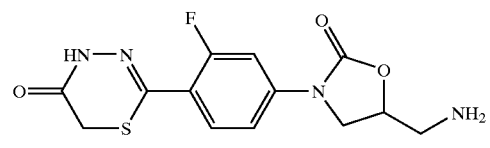

20% Trifluoroacetic acid/dichloromethane (2 ml) is added to [{4-[5(S)-(tert-butoxycarbonylaminomethyl)-2-oxo-oxazolidin-3-yl]-2-fluorophenyl}-(tert-butoxycarbonylhydrazono)-methylsulfanyl]-acetic acid methyl ester (0.25 g, 0.449 mmol) and the mixture is stirred at room temperature for 30 minutes. The reaction is evaporated to dryness and the TFA salt is neutralized with saturated aqueous sodium bicarbonate to give a white precipitate which is washed well with water and dried under vacuum (0.14 g, 99%); $^1$HNMR (300 MHz, MeOH-d$_4$) δ 3.33–3.43 (m, 2H), 3.53 (s, 2H), 3.88 (dd, J=6.6, 9.3 Hz, 1H), 4.30 (t, J=9.1 Hz, 1H), 4.90–5.03 (m, 1H), 7.39 (dd, J=2,2, 8.8 Hz, 1H), 7.63 (dd, J=2.2, 14 Hz, 1H), 7.73 (t, J=8.2 Hz, 1H); R$_f$(10% MeOH/DCM)=0.077; MS (m/z): [M+H]$^+$=325.

II. [{4-[5(S)-(tert-Butoxycarbonylaminomethyl)-2-oxo-oxazolidin-3-yl]-2-fluorophenyl}-(tert-butoxycarbonylhydrazono)-methylsulfanyl]-acetic acid methyl ester

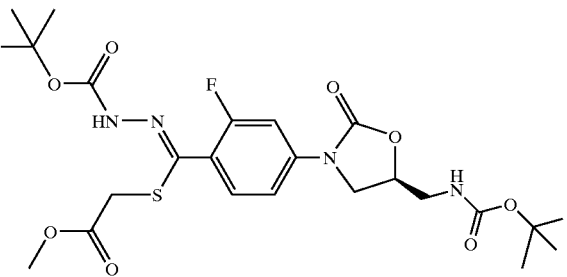

Methyl bromoacetate (0.064 ml, 0.681 mmol) is added to N'-{4-[5(S)-(tert-butoxycarbonylaminomethyl)-2-oxo-oxazolidin-3-yl]-2-fluorothiobenzoyl}-hydrazinecarboxylic acid tert-butyl ester (0.300 g, 0.619 mmol) and triethylamine (0.1 ml, 0.717 mmol) in DMF (3 ml) and the mixture is stirred at 65° C. for 10 h. The reaction mixture is evaporated and the residue is dissolved in ethyl acetate. The solution is washed with water and brine, dried (MgSO$_4$), and evaporated to give crude product which is purified by flash column chromatography (30% EtOAc/Hexane) to give an oil (0.29 g, 84%); $^1$HNMR (300 MHz, DMSO-d$_6$) δ 1.34 (s, 9H), 1.45 (s, 9H), 3.29 (t, J=5.5 Hz, 2H), 3.48 (s, 3H), 3.50 (s, 2H), 3.82 (dd, J=6.3, 9.3 Hz, 1H), 4.14 (t, J=9.1 Hz, 1H), 4.69–4.77 (m, 1H), 7.25 (t, J=5.8 Hz, 1H), 7.37–7.40 (m, 2H), 7.55 (dd, J=1.1, 14 Hz, 1H), 9.77 (s, 1H); mp 153–5; R$_f$ (10% MeOH/DCM)=0.23 MS (m/z): [M+H]$^+$=557.

III. N'-{4-[5(S)-(tert-Butoxycarbonylaminomethyl)-2-oxo-oxazolidin-3-yl]-2-fluorothiobenzoyl}-hydrazinecarboxylic acid tert-butyl ester

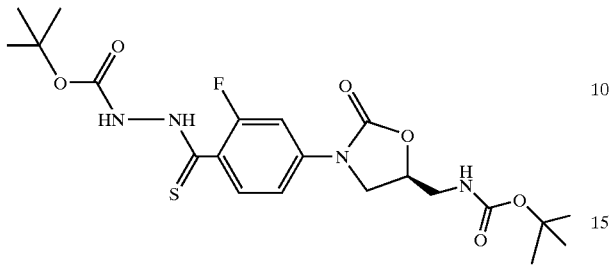

N'-{4-[5(S)-(tert-Butoxycarbonylaminomethyl)-2-oxo-oxazolidin-3-yl]-2-fluorobenzoyl}-hydrazinecarboxylic acid tert-butyl ester (1.73 g, 0.0037 mol) and Lawesson's reagent (1.50 g, 0.0037 mol) are suspended in dioxane and heated at 85° C. overnight. The reaction mixture is evaporated to dryness and the residue is purified by flash column chromatography (gradient from DCM to 5% acetone/DCM) to give product as a yellow solid (1.17 g, 65%); $^1$HNMR (300 MHz, DMSO-d$_6$) δ 1.35 (s, 9H), 1.42 (s, 9H), 3.28 (t, J=5 Hz, 2H), 3.80 (dd, J=6.1, 9.1 Hz, 1H), 4.13 (t, J=8.8 Hz, 1H), 4.68–4.76 (m, 1H), 7.24 (t, J=5.8 Hz, 1H), 7.32–7.36 (m, 1H), 7.47–7.59 (m, 2H), 11.8 (s, 1H); R$_f$(10% MeOH/DCM)=0.77.

IV. N'-{4-[5(S)-(tert-Butoxycarbonylaminomethyl)-2-oxo-oxazolidin-3-yl]-2-fluorobenzoyl}-hydrazinecarboxylic acid tert-butyl ester

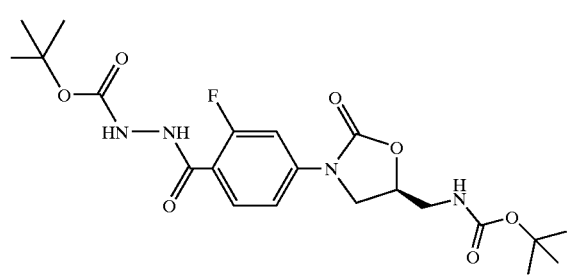

Di-tert-butyl dicarbonate (2.03 ml, 0.00884 mol) is added dropwise to a mixture of N'-[4-(5(S)-aminomethyl-2-oxo-oxazolidin-3-yl]-2-fluorobenzoyl}-hydrazinecarboxylic acid tert-butyl ester (3.09 g, 0.00839 mol) and pyridine (1.02 ml, 0.0126 mol) in DCM (50 ml) at 0° C. The reaction mixture is stirred at 0° C. for 1 hour, allowed to warm to room temperature and then stirred another 1 hour. The reaction mixture is washed with 2N HCl and brine, dried (MgSO$_4$) and evaporated. The residue is purified by flash column chromatography (50% EtOAc/DCM) to give product as a white solid (2.95 g, 75%); $^1$HNMR (300 MHz, DMSO-d$_6$) δ 1.34 (s, 9H), 1.42 (s, 9H), 3.28 (t, J=5 Hz, 2H), 3.82 (dd, J=6.0, 9.1 Hz, 1H), 4.14 (t, J=8.8 Hz, 1H), 4.69–4.77 (m, 1H), 7.24 (t, J=5.8 Hz, 1H), 7.39 (dd, J=2, 8.8 Hz), 7.54 (dd, J=2.2, 13.5 Hz, 1H), 7.66 (t, J=8.2 Hz, 1H), 8.95 (s, 1H); R$_f$(10% MeOH/DCM)=0.63.

V. N'-[4-(5(S)-Aminomethyl-2-oxo-oxazolidin-3-yl]-2-fluorobenzoyl]-hydrazinecarboxylic acid tert-butyl ester

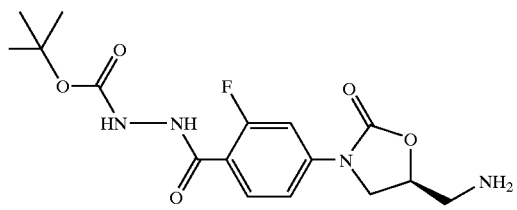

Triphenylphosphine (2.58 g, 0.00981 mol) is added portion-wise to a solution of N'-[4-(5(R)-azidomethyl-2-oxo-oxazolidin-3-yl)-2-fluorobenzoyl]-hydrazinecarboxylic acid tert-butyl ester (3.52 g, 0.00892 mol) in THF (30 ml) and then stirred at room temperature for 2 h at room temperature. Water (2.57 ml, 0.143 mol) is added and the mixture heated at 40° C. overnight. The reaction mixture is evaporated and the residue is purified by flash column chromatography (gradient DCM to 2% MeOH/DCM) to give product as an oil (3.09 g, 94%); $^1$HNMR (300 MHz, DMSO-d$_6$) δ 1.42 (s, 9H), 2.79–2.92 (m, 2H), 3.89 (dd, J=6.6, 9.1 Hz, 1H), 4.10 (t, J=8.8 Hz, 1H), 4.63–4.71 (m, 1H), 7.42 (dd, J=1.9, 8.5 Hz, 1H), 7.56 (dd, J=2.2, 13.2, 1H), 7.66 (t, J=8.2, 1H); R$_f$(10% MeOH/DCM)=0.15.

VI. N'-[4-(5(R)-Azidomethyl-2-oxo-oxazolidin-3-yl)-2-fluorobenzoyl]-hydrazinecarboxylic acid tert-butyl ester

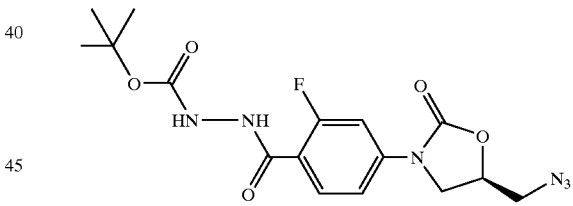

Diisopropylethylamine (4.67 ml, 0.0268 mol) is added to a mixture of 4-(5(R)-Azidomethyl-2-oxo-oxazolidin-3-yl)-2-fluorobenzoic acid (2.50 g, 0.00892 mol) [prepared according to the procedure described in U.S. Pat. No. 6,239,152] and O-(7-azabenzotriazol-1-yl)-N,N,N',N'-tetramethyluronium hexafluorophosphate (3.73 g, 0.00981 mol) in DMF (30 ml) and stirred for 20 minutes at room temperature. tert-Butyl carbazate (1.30 g, 0.00981 mol) is then added and the mixture stirred at room temperature overnight. The reaction mixture is evaporated under vacuum and the residue diluted with water. The resulting precipitate is filtered and dried under vacuum to give product as a white solid (3.52 g, 99%); $^1$HNMR (300 MHz, DMSO-d$_6$) δ 1.42 (s, 9H), 3.72–3.76 (m, 2H), 3.81 (dd, J=6.0, 9.3 Hz, 1H), 4.17 (t, J=9.1 Hz, 1H), 4.88–4.96 (m, 1H), 7.43 (dd, J=2.2, 8.8 Hz, 1H), 7.57 (dd, J=2.2, 13.2, 1H), 7.66 (t, J=8.2 Hz, 1H), 8.96 (s, 1H), 9.92 (s, 1H); R$_f$(EtOAc)=0.54; mp 173–5.

Example 2

N-{3-[3-Fluoro-4-(6(S)-methyl-5-oxo-5,6-dihydro-4H-[1,3,4]thiadiazin-2-yl)-phenyl]-2-oxo-oxazolidin-5(S)-ylmethyl}-acetamide

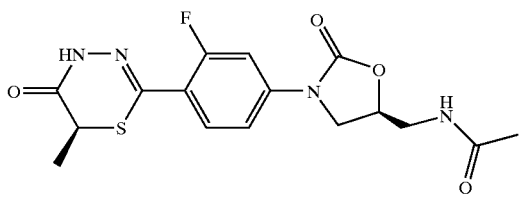

2-[4-(5-Aminomethyl-2-oxo-oxazolidin-3-yl)-2-fluorophenyl]-6-methyl-4H-[1,3,4]thiadiazin-5-one, trifluoroacetate salt is dissolved in pyridine (2 ml) and acetic anhydride (0.0163 ml, 0.173 mmol) is added. The reaction is stirred at room temperature for 4 hours and then evaporated to dryness. The residue is purified by PTLC (10% MeOH/DCM) to give pure product as a white solid (0.046 g, 76%); $^1$HNMR (300 MHz, DMSO-d$_6$) δ 1.34 (d, J=7.1 Hz, 3H), 1.82 (s, 3H), 3.41 (t, J=5.5, 2H), 3.71–3.82 (m, 2H), 4.14 (t, J=9.3 Hz, 1H), 4.71–4.79 (m, 1H), 7.41 (dd, J=1.9, 8.8 Hz, 1H), 7.58 (dd, J=1.7, 14, 1H), 7.68 (t, J=8.5, 1H), 8.25 (t, J=5.5 Hz, 1H), 11.7 (s, 1H); mp 200–2; MS (m/z): [M+H]$^+$=381.

The intermediates for this compound are prepared as follows:

I. 2-[4-(5(S)-Aminomethyl-2-oxo-oxazolidin-3-yl)-2-fluorophenyl]-6-methyl-4H-[1,3,4]thiadiazin-5-one, trifluoroacetate salt

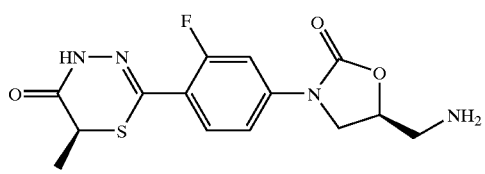

20% Trifluoroacetic acid/dichloromethane (2 ml) is added to 2-[{4-[5(S)-(tert-butoxycarbonylaminomethyl-2-oxo-oxazolidin-3-yl]-2-fluorophenyl}-(tert-butoxycarbonylhydrazono)-methylsulfanyl]-propionic acid methyl ester and the mixture is stirred at room temperature for 30 minutes. The reaction is evaporated to dryness and the TFA salt used directly in the next step; $^1$HNMR (300 MHz, MeOH-d$_4$) δ 1.46 (d, J=7.1 3H), 3.33–3.43 (m, 2H), 3.67 (q, J=7.1 Hz, 1H), 3.88 (dd, J=6.6, 9.6 Hz, 1H), 4.30 (t, J=9.3 Hz, 1H), 4.90–5.01 (m, 1H), 7.39 (dd, J=2,2, 8.8 Hz, 1H), 7.63 (dd, J=2.2, 13.5 Hz, 1H), 7.70 (t, J=8.5 Hz, 1H); MS (m/z): [M+H]$^+$=453.

II. 2-[{4-[5(S)-(tert-Butoxycarbonylaminomethyl)-2-oxo-oxazolidin-3-yl]-2-fluorophenyl}-(tert-butoxycarbonylhydrazono)-methylsulfanyl]-propionic acid methyl ester

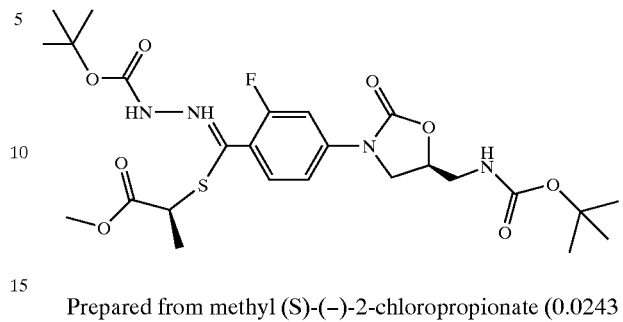

Prepared from methyl (S)-(–)-2-chloropropionate (0.0243 ml, 0.227 mmol) and N'-{4-[5(S)-(tert-butoxycarbonylaminomethyl)-2-oxo-oxazolidin-3-yl]-2-fluorothiobenzoyl}-hydrazinecarboxylic acid tert-butyl ester (0.100 g, 0.206 mmol) according to the procedure of Example 1, Intermediate II (0.090 g, 77%); $^1$HNMR (300 MHz, DMSO-d$_6$) δ 1.31 (d, J=7.1 Hz, 3H), 1.34 (s, 9H), 1.45 (s, 9H), 3.29 (t, J=5.2 Hz, 2H), overlapping 3.51 (q, J=7.1 Hz, 1H) and 3.51 (s, 3H), 3.83 (dd, J=6.0, 9.1 Hz, 1H), 4.14 (t, J=9.1 Hz, 1H), 4.71–4.75 (m, 1H), 7.25 (t, J=5.8 Hz, 1H), 7.39 (dd, J=1.9, 8.8 Hz, 1H), 7.48 (t, J=8.5 Hz, 1H), 7.56 (dd, J=1.9, 13, 1H), 9.74 (s, 1H); MS (m/z): [M+H]$^+$=571.

Example 3

N-{3-[3-Fluoro-4-(6(R)-methyl-5-oxo-5,6-dihydro-4H-[1,3,4]thiadiazin-2-yl)-phenyl]-2-oxo-oxazolidin-5(S)-ylmethyl}-acetamide

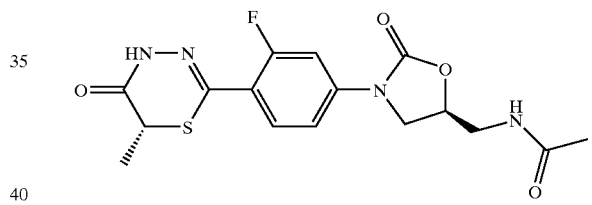

Prepared from 2-[4-(5-aminomethyl-2-oxo-oxazolidin-3-yl)-2-fluorophenyl]-6-methyl-4H-[1,3,4]thiadiazin-5-one, trifluoroacetate salt according to the method of Example 2 (0.086 g, 93%); $^1$HNMR (300 MHz, DMSO-d$_6$) δ 1.34 (d, J=7.1 Hz, 3H), 1.82 (s, 3H), 3.42 (t, J=5.2 Hz, 2H), 3.73–3.82 (m, 2H), 4.14 (t, J=9.1 Hz, 1H), 4.71–4.78 (m, 1H), 7.39 (dd, J=1.9, 8.8 Hz, 1H), 7.58 (dd, J=1.9, 14, 1H), 7.68 (t, J=8.5, 1H), 8.25 (t, J=5.8 Hz, 1H), 11.7 (s, 1H) mp 205–6; MS (m/z): [M+H]$^+$=381.

The intermediates for this compound are prepared as follows:

I. 2-[4-(5(S)-Aminomethyl-2-oxo-oxazolidin-3-yl)-2-fluorophenyl]-6-methyl-4H-[1,3,4]thiadiazin-5-one, trifluoroacetate salt

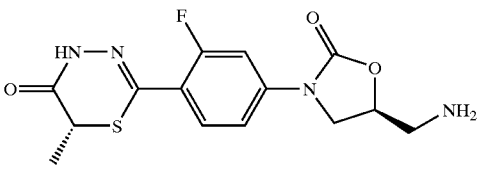

Prepared from 2-[{4-[5(S)-(tert-butoxycarbonylaminomethyl)-2-oxo-oxazolidin-3-yl]-2-fluorophenyl}-(tert-butoxycarbonylhydrazono)-methylsulfanyl]-propionic acid methyl ester according to the method of Example 2, Intermediate I; ¹HNMR (300 MHz, MeOH-d₄) δ 1.46 (d, J=7.1 3H), 3.33–3.43 (m, 2H), 3.67 (q, J=7.1 Hz, 1H), 3.88 (dd, J=6.6, 9.6 Hz, 1H), 4.30 (t, J=9.3 Hz, 1H), 4.90–5.01 (m, 1H), 7.39 (dd, J=2,2, 8.8 Hz, 1H), 7.63 (dd, J=2.2, 13.5 Hz, 1H), 7.71 (t, J=8.5 Hz, 1H); MS (m/z): [M+H]⁺=453.

II. 2-[{4-[5(S)-(tert-Butoxycarbonylaminomethyl)-2-oxo-oxazolidin-3-yl]-2-fluorophenyl}-(tert-butoxycarbonylhydrazono)-methylsulfanyl]-propionic acid methyl ester

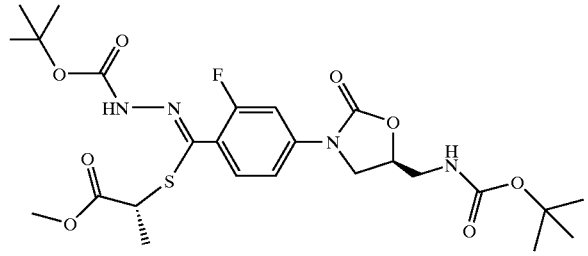

Prepared from methyl (R)-(+)-2-chloropropionate (0.0241 ml, 0.227 mmol) and N'-{4-[5(S)-(tert-butoxycarbonylaminomethyl)-2-oxo-oxazolidin-3-yl]-2-fluorothiobenzoyl}-hydrazinecarboxylic acid tert-butyl ester (0.100 g, 0.206 mmol) according to the procedure of Example 1, Intermediate II (0.092 g, 78%); ¹HNMR (300 MHz, DMSO-d₆) δ 1.31 (d, J=7.1 Hz, 3H), 1.34 (s, 9H), 1.45 (s, 9H), 3.29 (t, J=5.2 Hz, 2H), overlapping 3.51 (q, J=7.1 Hz, 1H) and 3.51 (s, 3H), 3.83 (dd, J=6.0, 9.1 Hz, 1H), 4.14 (t, J=9.1 Hz, 1H), 4.69–4.77 (m, 1H), 7.25 (t, J=5.8 Hz, 1H), 7.39 (dd, J=1.9, 8.8 Hz, 1H), 7.48 (t, J=8.5 Hz, 1H), 7.56 (dd, J=1.9, 13, 1H), 9.74 (s, 1H); MS (m/z): [M+H]⁺=571.

Example 4

N-{3-[4-(6,6-Dimethyl-5-oxo-5,6-dihydro-4H-[1,3,4]thiadiazin-2-yl)-3-fluorophenyl]-2-oxo-oxazolidin-5(S)-ylmethyl}-acetamide

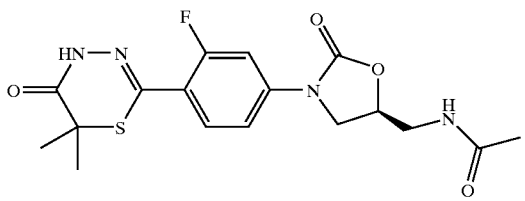

Prepared from 2-[4-(5(S)-aminomethyl-2-oxo-oxazolidin-3-yl)-2-fluorophenyl]-6,6-dimethyl-4H-[1,3,4]thiadiazin-5-one, trifluoroacetate salt according to the method of Example 2 (0.053 g, 86%); ¹HNMR (300 MHz, DMSO-d₆) δ 1.40 (s, 6H), 1.82 (s, 3H), 3.42 (t, J=5.5 Hz, 2H), 3.76 (dd, J=6.6, 9.3 Hz, 1H), 4.14 (t, J=9.1 Hz, 1H), 4.71–4.78 (m, 1H), 7.41 (dd, J=2.2, 8.8 Hz, 1H), 7.58 (dd, J=1.9, 14, 1H), 7.66 (t, J=8.8 Hz, 1H), 8.25 (t, J=5.8 Hz, 1H), 11.7 (s, 1H); mp 179–81; MS (m/z): [M+H]⁺=395.

The intermediates for this compound are prepared as follows:
I. 2-[4-(5(S)-Aminomethyl-2-oxo-oxazolidin-3-yl)-2-fluorophenyl]-6,6-dimethyl-4H-[1,3,4]thiadiazin-5-one, trifluoroacetate salt

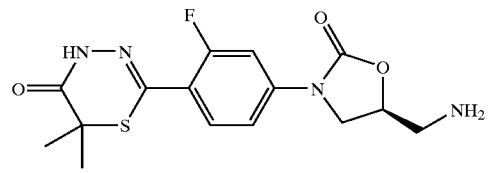

Prepared from 2-[{4-[5(S)-(tert-butoxycarbonylaminomethyl)-2-oxo-oxazolidin-3-yl]-2-fluorophenyl}-(tert-butoxycarbonylhydrazono)-methylsulfanyl]-2-methylpropionic acid ethyl ester according to the method of Example 2, Intermediate I; ¹HNMR (300 MHz, MeOH-d₄) δ 1.48 (s, 6H), 3.33–3.43 (m, 2H), 3.88 (dd, J=6.6, 9.6 Hz, 1H), 4.30 (t, J=9.3 Hz, 1H), 4.90–5.03 (m, 1H), 7.39 (dd, J=2,2, 8.8 Hz, 1H), 7.62 (dd, J=2.2, 14 Hz, 1H), 7.69 (t, J=8.5 Hz, 1H); (MS (m/z): [M+H]⁺=467.

II. 2-[{4-[5(S)-(tert-Butoxycarbonylaminomethyl)-2-oxo-oxazolidin-3-yl]-2-fluorophenyl}-(tert-butoxycarbonylhydrazono)methylsulfanyl]-2-methylpropionic acid ethyl ester

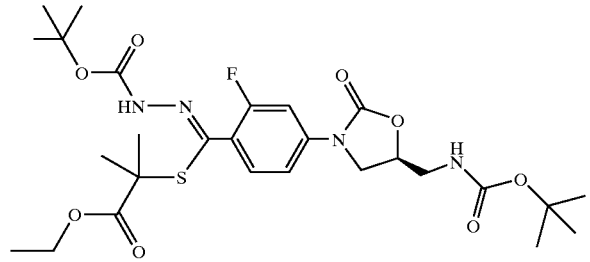

Prepared from ethyl 2-bromoisobutyrate (0.0333 ml, 0.227 mmol) and N'-{4-[5(S)-(tert-butoxycarbonylaminomethyl)-2-oxo-oxazolidin-3-yl]-2-fluorothiobenzoyl}-hydrazinecarboxylic acid tert-butyl ester (0.100 g, 0.206 mmol) according to the procedure of Example 1, Intermediate II (0.094 g, 76%); ¹HNMR (300 MHz, DMSO-d₆) δ 1.10 (t, J=7.1 Hz, 3H), 1.35 (s, 9H), 1.38 (s, 6H), 1.46 (s, 9H), 3.29 (t, J=5.5 Hz, 2H), overlapping 3.78 (q, J=7.1 Hz, 2H) and 3.81 (dd, J=6.6, 9.3 Hz, 1H), 4.13 (t, J=9.1 Hz, 1H), 4.70–4.75 (m, 1H), 7.24 (t, J=5.8 Hz, 1H), 7.34 (dd, J=1.6, 8.5 Hz, 1H), overlapping 7.50 (t, J=8.8 Hz, 1H) and 7.50 (dd, J=2.2, 13 Hz, 1H), 9.65 (s, 1H); MS (m/z): [M+H]⁺=599.

Example 5

N-{3-[3-Fluoro-4-(6-ethyl-5-oxo-5,6-dihydro-4H-[1,3,4]thiadiazin-2-yl)-phenyl]-2-oxo-oxazolidin-5(S)-ylmethyl}-acetamide

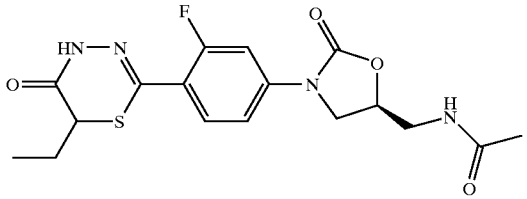

Prepared from 2-[4-(5(S)-aminomethyl-2-oxo-oxazolidin-3-yl)-2-fluorophenyl]-6-ethyl-4H-[1,3,4]thiadiazin-5-one, trifluoroacetate salt according to the method of Example 2 (0.055 g, 80%); ¹H NMR (300 MHz, DMSO-d₆) δ 0.99 (t, J=7.8 Hz, 3H), 1.55–1.60 (m, 1H), 1.76–1.81 (m, 1H), 1.83 (s, 3H), 3.42 (t, J=5.4 Hz, 2H), 3.63 (dd, J=6.3, 7.8 Hz, 1H), 3.74–3.79 (m, 1H), 4.15 (t, J=9.1 Hz, 1H), 4.74–4.77 (m, 1H), 7.42 (dd, J=1.8, 8.7 Hz, 1H), 7.59 (dd, J=2.4, 13.8 Hz, 1H), 7.66 (t, J=8.7 Hz, 1H), 8.25 (t, J=5.7 Hz, 1H); mp 177–9; MS (m/z): [M+H]⁺=395.

The intermediates for this compound are prepared as follows:

I. 2-[4-(5(S)-Aminomethyl-2-oxo-oxazolidin-3-yl)-2-fluorophenyl]-6-ethyl-4H-[1,3,4]thiadiazin-5-one, trifluoroacetate salt

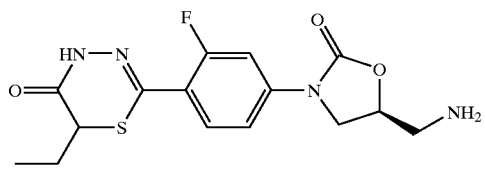

Prepared from 2-[{4-[5(S)-(tert-butoxycarbonylaminomethyl)-2-oxo-oxazolidin-3-yl]-2-fluorophenyl}-(tert-butoxycarbonylhydrazono)-methylsulfanyl]-butyric acid methyl ester according to the method of Example 2, Intermediate I; MS (m/z): [M+H]⁺=467.

II. 2-[{4-[5(S)-(tert-Butoxycarbonylaminomethyl)-2-oxo-oxazolidin-3-yl]-2-fluorophenyl}-(tert-butoxycarbonylhydrazono)-methylsulfanyl]-butyric acid methyl ester

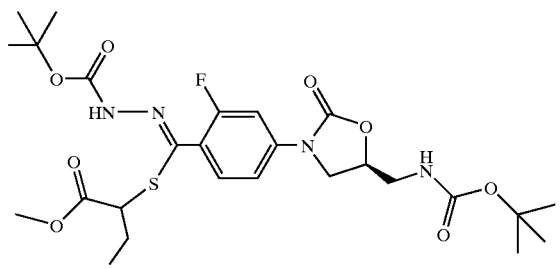

Prepared from methyl 2-bromobutyrate (0.0261 ml, 0.227 mmol) and N'-{4-[5(S)-(tert-butoxycarbonylaminomethyl)-2-oxo-oxazolidin-3-yl]-2-fluorobenzoyl}-hydrazinecarboxylic acid tert-butyl ester (0.100 g, 0.206 mmol) according to the procedure of Example 1, Intermediate II (0.102 g, 85%); MS (m/z): [M+H]⁺=585.

Example 6

N-{3-[3-Fluoro-4-(5-oxo-6-propyl-5,6-dihydro-4H-[1,3,4]thiadiazin-2-yl)-phenyl]-2-oxo-oxazolidin-5(S)-ylmethyl}-acetamide

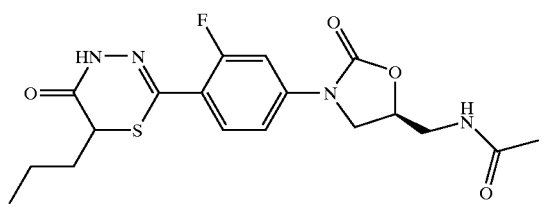

Prepared from 2-[4-(5(S)-aminomethyl-2-oxo-oxazolidin-3-yl)-2-fluorophenyl]-6-propyl-4H-[1,3,4]thiadiazin-5-one, trifluoroacetate salt according to the method of Example 2 (0.050 g, 68%); ¹H NMR (300 MHz, DMSO-d₆) δ 0.89 (t, J=7.2 Hz, 3H), 1.40–1.53 (m, 2H), 1.69–1.72 (m, 2H), 1.83 (s, 3H), 3.43 (t, J=5.4 Hz, 2H), 3.69 (dd, J=6.3, 7.8 Hz, 1H), 3.77 (dd, J=6.6, 9.3 Hz, 1H), 4.15 (t, J=9.3 Hz, 1H), 4.76–4.77 (m, 1H), 7.42 (dd, J=1.8, 8.4 Hz, 1H), 7.59 (dd, J=2.4, 13.8 Hz, 1H), 7.66 (t, J=8.7 Hz, 1H), 8.28 (t, J=5.7 Hz, 1H); foam; MS (m/z): [M+H]⁺=409.

The intermediates for this compound are prepared as follows:

I. 2-[4-(5(S)-Aminomethyl-2-oxo-oxazolidin-3-yl)-2-fluorophenyl]-6-propyl-4H-[1,3,4]thiadiazin-5-one, trifluoroacetate salt

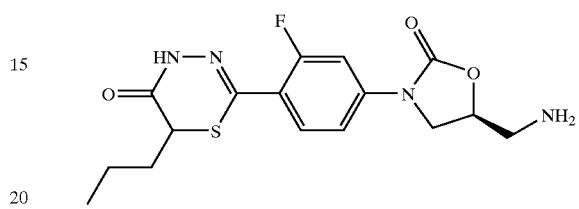

Prepared from 2-[{4-[5(S)-(tert-butoxycarbonylaminomethyl)-2-oxo-oxazolidin-3-yl]-2-fluorophenyl}-(tert-butoxycarbonylhydrazono)-methylsulfanyl]-pentanoic acid ethyl ester according to the method of Example 2, Intermediate I; MS (m/z): [M+H]⁺=481.

II. 2-[{4-[5(S)-(tert-Butoxycarbonylaminomethyl)-2-oxo-oxazolidin-3-yl]-2-fluorophenyl}-(tert-butoxycarbonylhydrazono)-methylsulfanyl]-pentanoic acid ethyl ester

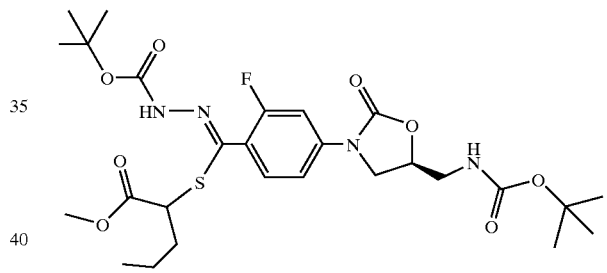

Prepared from ethyl 2-bromovalerate (0.0359 ml, 0.227 mmol) and N'-{4-[5(S)-(tert-butoxycarbonylaminomethyl)-2-oxo-oxazolidin-3-yl]-2-fluorothiobenzoyl}-hydrazinecarboxylic acid tert-butyl ester (0.100 g, 0.206 mmol) according to the procedure of Example 1, Intermediate II (0.111 g, 88%); MS (m/z): [M+H]⁺=613.

Example 7

N-{3-[3-Fluoro-4-(6-isopropyl-5-oxo-5,6-dihydro-4H-[1,3,4]thiadiazin-2-yl)-phenyl]-2-oxo-oxazolidin-5(S)-ylmethyl}-acetamide

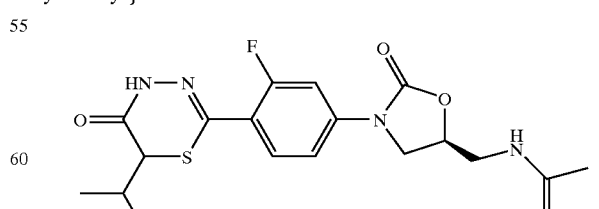

Prepared from 2-[4-(5(S)-aminomethyl-2-oxo-oxazolidin-3-yl)-2-fluorophenyl]-6-isopropyl-4H-[1,3,4]thiadiazin-5-one, trifluoroacetate salt according to the method of Example 2 (0.045 g, 70%); $^1$H NMR (300 MHz, DMSO-d$_6$) δ 0.97–1.01 (m, 6H), 1.83 (s, 3H), 1.92–1.97 (m, 1H), 3.42 (t, J=5.4 Hz, 2H), 3.52 (d, J=7.2 Hz, 1H), 3.77 (dd, J=6.6, 9.3 Hz, 1H), 4.15 (t, J=9.0 Hz, 1H), 4.74–4.77 (m, 1H), 7.42 (dd, J=1.8, 8.7 Hz, 1H), 7.59 (dd, J=2.1, 13.8 Hz, 1H), 7.66 (t, J=8.7 Hz, 1H), 8.27 (t, J=5.7 Hz, 1H); mp 201–3; MS (m/z): [M+H]$^+$=409.

The intermediates for this compound are prepared as follows:

I. 2-[4-(5(S)-Aminomethyl-2-oxo-oxazolidin-3-yl)-2-fluorophenyl]-6-isopropyl-4H[1,3,4]thiadiazin-5-one, trifluoroacetate salt

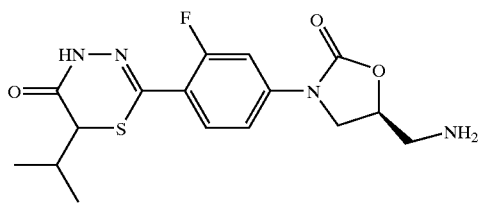

Prepared from 2-[{4-[5(S)-(tert-butoxycarbonylaminomethyl)-2-oxo-oxazolidin-3-yl]-2-fluorophenyl}-(tert-butoxycarbonylhydrazono)-methylsulfanyl]-3-methylbutyric acid ethyl ester according to the method of Example 2, Intermediate I; MS (m/z): [M+H]$^+$=481.

II. 2-[{4-[5(S)-(tert-Butoxycarbonylaminomethyl)-2-oxo-oxazolidin-3-yl]-2-fluorophenyl}-(tert-butoxycarbonylhydrazono)-methylsulfanyl]-3-methylbutyric acid ethyl ester

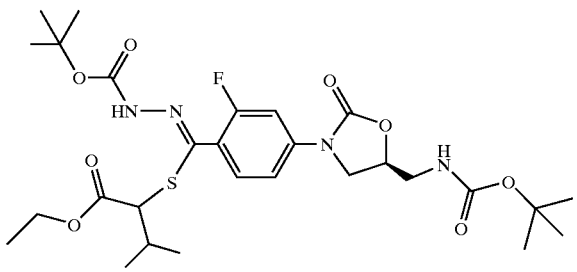

Prepared from ethyl 2-bromoisovalerate (0.039 ml, 0.227 mmol) and N'-{4-[5(S)-(tert-butoxycarbonylaminomethyl)-2-oxo-oxazolidin-3-yl]-2-fluorothiobenzoyl}-hydrazinecarboxylic acid tert-butyl ester (0.100 g, 0.206 mmol) according to the procedure of Example 1, Intermediate II (0.097 g, 77%); MS (m/z): [M+H]$^+$=613.

Example 8

N-{3-[3-Fluoro-4-(9-oxo-5-thia-7,8-diazaspiro[3.5]non-6-en-6-yl)-phenyl]-2-oxo-oxazolidin-5(S)-ylmethyl}-acetamide

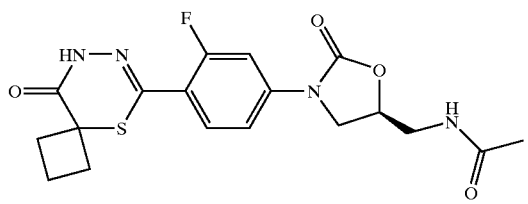

Prepared from 6-[4-(5(S)-aminomethyl-2-oxo-oxazolidin-3-yl)-2-fluorophenyl]-5-thia-7,8-diazaspiro[3.5]non-6-en-9-one, trifluoroacetate salt according to the method of Example 2 (0.100 g, 50%); $^1$H NMR (300 MHz, DMSO-d$_6$) δ 1.82 (s, 3H), 1.93–1.98 (m, 1H), 2.07–2.15 (m, 3H), 2.63–2.70 (m, 2H), 3.42 (t, J=5.4 Hz, 2H), 3.76 (dd, J=6.6, 9.3 Hz, 1H), 4.14 (t, J=9.3 Hz, 1H), 4.73–4.78 (m, 1H), 7.41 (dd, J=2.1, 8.7 Hz, 1H), 7.58 (dd, J=2.1, 13.5 Hz, 1H), 7.67 (t, J=9.0 Hz, 1H), 8.24 (t, J=5.7 Hz, 1H); mp 214–5; MS (m/z): [M+H]$^+$=407.

The intermediates for this compound are prepared as follows:

I. 6-[4-(5(S)-Aminomethyl-2-oxo-oxazolidin-3-yl)-2-fluorophenyl]-5-thia-7,8-diazaspiro[3.5]non-6-en-9-one, trifluoroacetate salt

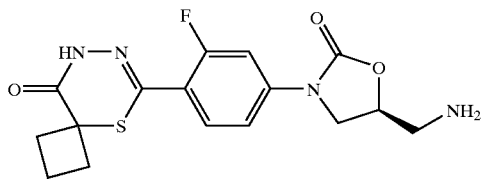

Prepared from 1-[{4-[5(S)-(tert-butoxycarbonylaminomethyl)-2-oxo-oxazolidin-3-yl]-2-fluorophenyl}-(tert-butoxycarbonylhydrazono)-methylsulfanyl]-cyclobutanecarboxylic acid ethyl ester according to the method of Example 2, Intermediate I; MS (m/z): [M+H]$^+$= 479.

II. 1-[{4-[5(S)-(tert-Butoxycarbonylaminomethyl)-2-oxo-oxazolidin-3-yl]-2-fluorophenyl}-(tert-butoxycarbonylhydrazono)-methylsulfanyl]-cyclobutanecarboxylic acid ethyl ester

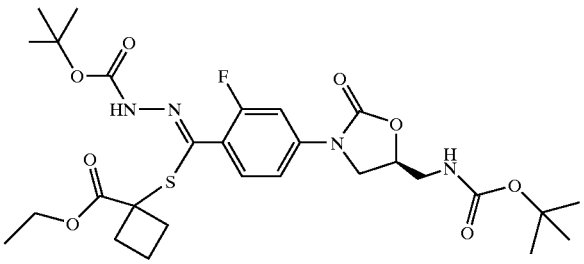

Prepared from ethyl 1-bromocyclobutanecarboxylate (0.110 ml, 0.681 mmol) and N'-{4-[5(S)-(tert-butoxycarbonylaminomethyl)-2-oxo-oxazolidin-3-yl]-2-fluorothiobenzoyl}-hydrazinecarboxylic acid tert-butyl ester (0.300 g, 0.619 mmol) according to the procedure of Example 1, Intermediate II (0.30 g, 80%); MS (m/z): [M+H]$^+$=611.

Example 9

N-{3-[3-Fluoro-4-(5-oxo-6-phenyl-5,6-dihydro-4H-[1,3,4]thiadiazin-2-yl)-phenyl]-2-oxo-oxazolidin-5(S)-ylmethyl}-acetamide

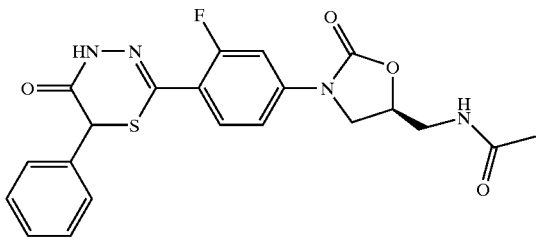

Prepared from 2-[4-(5(S)-aminomethyl-2-oxo-oxazolidin-3-yl)-2-fluorophenyl]-6-phenyl-4H-[1,3,4]thiadiazin-5-one, trifluoroacetate salt according to the method of Example 2 (0.053 g, 90%); ¹HNMR (300 MHz, DMSO-d₆) δ 1.81 (s, 3H), 3.40 (t, J=5.5 Hz, 2H), 3.47 (dd, J=6.6, 9.3 Hz, 1H), 4.12 (t, J=9.1 Hz, 1H), 4.70–4.78 (m, 1H), 5.15 (s, 1H), 7.30–7.41 (m, 6H), overlapping 7.57 (dd, J=1.9, 14 Hz, 1H) and 7.59 (t, J=8.8 Hz, 1H), 12.0 (s, 1H); mp 122–3; MS (m/z): [M+H]⁺=443.

The intermediates for this compound are prepared as follows

I. 2-[4-(5(S)-Aminomethyl-2-oxo-oxazolidin-3-yl)-2-fluorophenyl]-6-phenyl-4H-[1,3,4]thiadiazin-5-one, trifluoroacetate salt

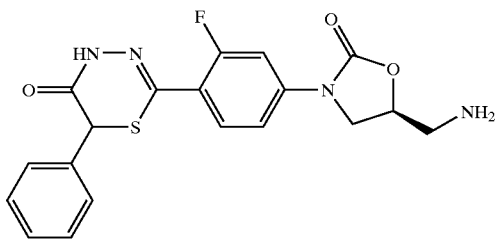

Prepared from [{4-[5(S)-(tert-butoxycarbonylaminomethyl)-2-oxo-oxazolidin-3-yl]-2-fluorophenyl}-(tert-butoxycarbonylhydrazono)-methylsulfanyl]-phenylacetic acid methyl ester according to the method of Example 2, Intermediate I; ¹HNMR (300 MHz, MeOH-d₄) δ 3.33–3.40 (m, 2H), 3.85 (dd, J=6.6, 9.6 Hz, 1H), 4.27 (t, J=9.3 Hz, 1H), 4.92 (s, 1H), 4.92–5.03 (m, 1H), 7.30–7.39 (m, 6H), 7.56–7.64 (m, 2H); MS (m/z): [M+H]⁺=515.

II. [{4-[5(S)-(tert-Butoxycarbonylaminomethyl)-2-oxo-oxazolidin-3-yl]-2-fluorophenyl}-(tert-butoxycarbonylhydrazono)-methylsulfanyl]-phenylacetic acid methyl ester

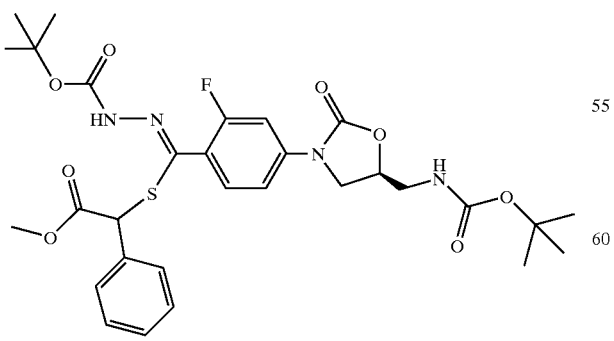

Prepared from methyl α-bromophenylacetate (0.0357 ml, 0.227 mmol) and N'-{4-[5(S)-(tert-butoxycarbonylaminomethyl)-2-oxo-oxazolidin-3-yl]-2-fluorothiobenzoyl}-hydrazinecarboxylic acid tert-butyl ester (0.100 g, 0.206 mmol) according to the procedure of Example 1, Intermediate II (0.085 g, 65%); ¹HNMR (300 MHz, DMSO-d₆) δ 1.35 (s, 9H), 1.44 (s, 9H), 3.30 (t, J=5.2 Hz, 2H), 3.49 (s, 3H), 3.83 (dd, J=6.6, 9.3 Hz, 1H), 4.15 (t, J=9.1 Hz, 1H), overlapping 4.70–4.77 (m, 1H) and 4.73 (s, 1H), 7.22–7.38 (m, 8H), 9.83 (s, 1H); MS (m/z): [M+H]⁺=633.

Example 10

N-{3-[3-Fluoro-4-(6-fluoro-5-oxo-5,6-dihydro-4H-[1,3,4]thiadiazin-2-yl)-phenyl]-2-oxo-oxazolidin-5(S)-ylmethyl}-acetamide

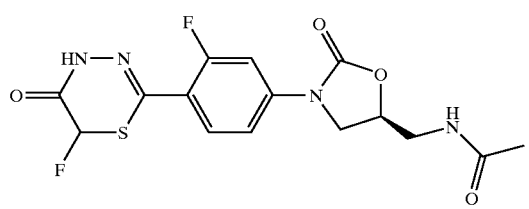

Prepared from 2-[4-(5(S)-aminomethyl-2-oxo-oxazolidin-3-yl)-2-fluorophenyl]-6-fluoro-4H-[1,3,4]thiadiazin-5-one, trifluoroacetate salt according to the method of Example 2 (0.019 g, 30%); ¹HNMR (300 MHz, DMSO-d₆) δ 1.82 (s, 3H), 3.42 (t, J=5.5, 2H), 3.75 (dd, J=6.3, 9.1, 2H), 4.14 (t, J=9.1 Hz, 1H), 4.70–4.83 (m, 1H), 6.61 (d, J=49 Hz, 1H), 7.45 (dd, J=2.2, 8.5 Hz, 1H), 7.60 (dd, J=2.2, 14, 1H), 7.69 (t, J=8.5 Hz, 1H), 8.25 (t, J=5.8 Hz, 1H); mp 218–20; MS (m/z): [M+H]⁺=385.

The intermediates for this compound are prepared as follows:

I. 2-[4-(5(S)-Aminomethyl-2-oxo-oxazolidin-3-yl)-2-fluorophenyl]-6-fluoro-4H-[1,3,4]thiadiazin-5-one, trifluoroacetate salt

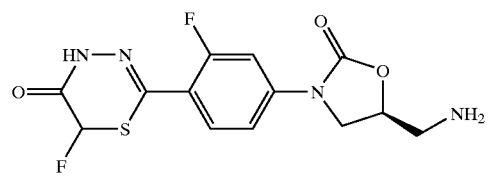

Prepared from [{4-[5(S)-(tert-butoxycarbonylaminomethyl)-2-oxo-oxazolidin-3-yl]-2-fluorophenyl}-(tert-butoxycarbonylhydrazono)-methylsulfanyl]-fluoroacetic acid ethyl ester according to the method of Example 2, Intermediate I; MS (m/z): [M+H]⁺=457.

II. [{4-[5(S)-(tert-Butoxycarbonylaminomethyl)-2-oxo-oxazolidin-3-yl]-2-fluorophenyl}-(tert-butoxycarbonylhydrazono)-methylsulfanyl]-fluoroacetic acid ethyl ester

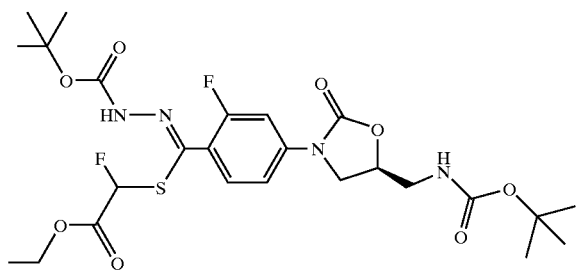

Prepared from ethyl bromofluoroacetate (0.0268 ml, 0.227 mmol) and N'-{4-[5(S)-(tert-Butoxycarbonylaminomethyl)-2-oxo-oxazolidin-3-yl]-2-fluorothiobenzoyl}-hydrazinecarboxylic acid tert-butyl ester (0.100 g, 0.206 mmol) according to the procedure of Example 1, Intermediate II (0.095 g, 78%); MS (m/z): [M+H]$^+$=589.

Example 11
N-{3-[3-Fluoro-4-(6-hydroxymethyl-5-oxo-5,6-dihydro-4H-[1,3,4]thiadiazin-2-yl)-phenyl]-2-oxo-oxazolidin-5(S)-ylmethyl}-acetamide

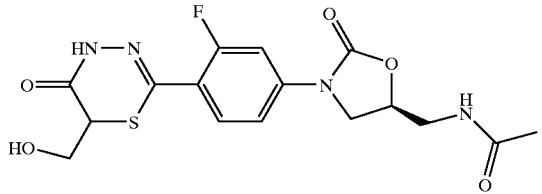

Prepared from 2-[4-(5(S)-aminomethyl-2-oxo-oxazolidin-3-yl)-2-fluorophenyl]-6-hydroxymethyl-4H-[1,3,4]thiadiazin-5-one, trifluoroacetate salt according to the method of Example 2 (0.059 g, 27%); $^1$H NMR (300 MHz, DMSO-d$_6$) δ 1.83 (s, 3H), 3.66–3.81 (m, 6H), 4.15 (t, J=9.0 Hz, 1H), 4.75–4.76 (m, 1H), 7.41 (dd, J=2.1, 9.0 Hz, 1H), 7.59 (dd, J=1.8, 13.8 Hz, 1H), 7.69 (t, J=8.4 Hz, 1H), 8.30 (t, J=5.4 Hz, 1H); foam; MS (m/z): [M+H]$^+$=397.

The intermediates for this compound are prepared as follows:

I. 2-[4-(5(S)-Aminomethyl-2-oxo-oxazolidin-3-yl)-2-fluorophenyl]-6-hydroxymethyl-4H-[1,3,4]thiadiazin-5-one, trifluoroacetate salt

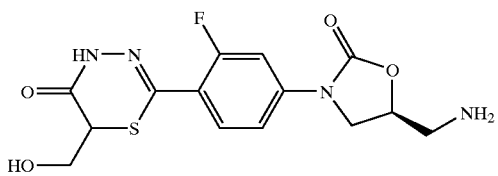

Prepared from 3-tert-butoxy-2-[{4-[5(S)-(tert-butoxycarbonylaminomethyl)-2-oxo-oxazolidin-3-yl]-2-fluorophenyl}-(tert-butoxycarbonylhydrazono)-methylsulfanyl]-propionic acid methyl ester according to the method of Example 2, Intermediate I; MS (m/z): [M+H]$^+$=469.

II. 3-tert-Butoxy-2-[{4-[5(S)-(tert-butoxycarbonylaminomethyl)-2-oxo-oxazolidin-3-yl]-2-fluorophenyl}-(tert-butoxycarbonylhydrazono)-methylsulfanyl]-propionic acid methyl ester

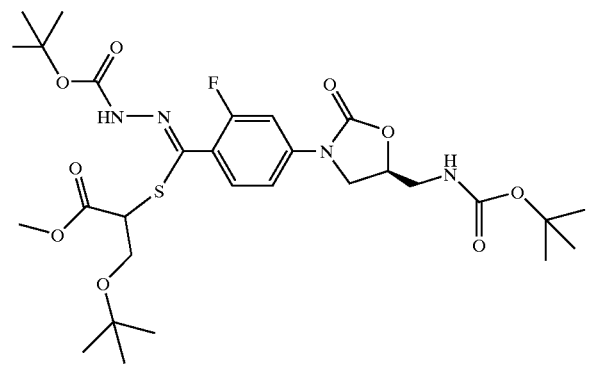

Prepared from 2(S)-bromo-3-tert-butoxypropionic acid methyl ester (0.153 g, 0.681 mmol) and N'-{4-[5(S)-(tert-butoxycarbonylaminomethyl)-2-oxo-oxazolidin-3-yl]-2-fluorothiobenzoyl}-hydrazinecarboxylic acid tert-butyl ester (0.300 g, 0.619 mmol) according to the procedure of Example 1, Intermediate II (0.35 g, 89%); MS (m/z): [M+H III. 2(S)-Bromo-3-tert-butoxypropionic acid methyl ester Sodium nitrite (4.1 g, 59 mmol) is added in small portions to a solution of potassium bromide (13.9 g, 116 mol) in 0.75 M aqueous HBr (180 ml) cooled to −5° C. L-Serine tert-butyl ether (5.00 g, 31 mmol) is then added portion-wise and the reaction stirred at −5° C. for 2 hours. The reaction mixture is extracted with cold ethyl acetate and the extracts washed with brine, dried (MgSO$_4$), and evaporated to give residue which is purified by flash column chromatography (1% acetic acid in 30% EtOAc/Hexane) (5.2 g, 75%). The acid is treated with excess diazomethane in ether and evaporated to give the methyl ester used directly in the next step.

Example 12
N-{3-[3-Fluoro-4-(6-(2-hydroxyethyl)-5-oxo-5,6-dihydro-4H-[1,3,4]thiadiazin-2-yl)-phenyl]-2-oxo-oxazolidin-5(S)-ylmethyl}-acetamide

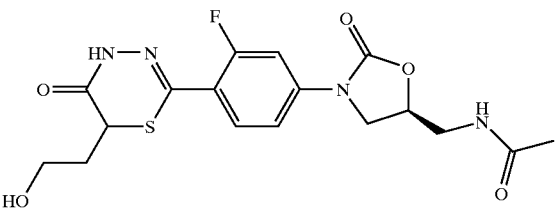

Prepared from 2-[4-(5(S)-aminomethyl-2-oxo-oxazolidin-3-yl)-2-fluorophenyl]-6-(2-hydroxyethyl)-4H-[1,3,4]thiadiazin-5-one, trifluoroacetate salt according to the method of Example 2 (0.021 g, 31%). MS (m/z): [M+H]$^+$=411. A second acetylation product is isolated and identified as acetic acid 2-(2-{4-[5(S)-(acetylaminomethyl)-2-oxo-oxazolidin-3-yl]-2-fluorophenyl}-5-oxo-5,6-dihydro-4H[1,3,4]thiadiazin-6-yl)-ethyl ester (0.025 g, 37%); $^1$H NMR (300 MHz, DMSO-d$_6$) δ 1.83–1.91 (m, 1H), 2.00 (s, 3H), 2.06–2.14 (m, 1H), 3.43 (t, J=5.4 Hz, 2H), 3.74–3.83 (m, 2H), 4.08–4.18 (m, 3H), 7.43 (dd, J=2.1, 8.7 Hz, 1H), 7.59 (dd, J=1.8, 13.5 Hz, 1H), 7.69 (t, J=8.7 Hz, 1H), 8.26 (t, J=5.7 Hz, 1H); mp 223–4; MS (m/z): [M+H]$^+$=453.

The intermediates for this compound are prepared as follows:

I. 2-[4-(5(S)-Aminomethyl-2-oxo-oxazolidin-3-yl)-2-fluorophenyl]-6-(2-hydroxyethyl)-4H-[1,3,4]thiadiazin-5-one, trifluoroacetate salt

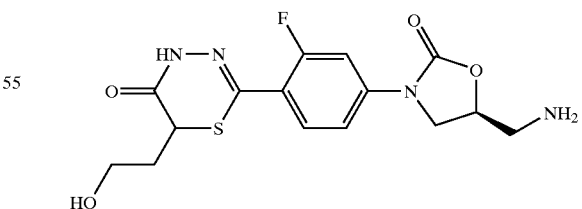

Prepared from N'-[{4-[5(S)-(tert-butoxycarbonylaminomethyl)-2-oxo-oxazolidin-3-yl]-2-fluorophenyl}-(2-oxo-tetrahydro-furan-3-ylsulfanyl)-methylene]-hydrazinecarboxylic acid tert-butyl ester according to the method of Example 2, Intermediate I; MS (m/z): [M+H]$^+$=483.

II. N'-[{4-[5(S)-(tert-Butoxycarbonylaminomethyl)-2-oxo-oxazolidin-3-yl]-2-fluorophenyl}-(2-oxo-tetrahydro-furan-3-ylsulfanyl)-methylene]-hydrazinecarboxylic acid tert-butyl ester

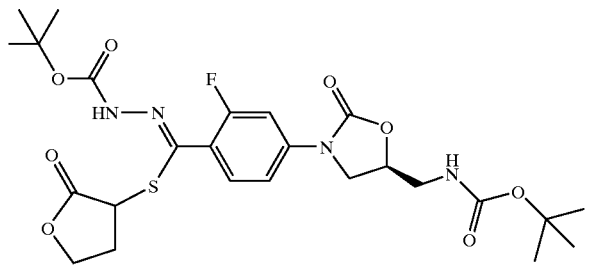

Prepared from α-bromo-γ-butyrolactone (0.021 ml, 0.227 mmol) and N'-{4-[5(S)-(tert-butoxycarbonylaminomethyl)-2-oxo-oxazolidin-3-yl]-2-fluorothiobenzoyl}-hydrazinecarboxylic acid tert-butyl ester (0.100 g, 0.206 mmol) according to the procedure of Example 1, Intermediate II (0.95 g, 80%); MS (m/z): [M+H]$^+$=569.

Example 13

2-{4-[5(S)-(Acetylaminomethyl)-2-oxo-oxazolidin-3-yl]-2-fluorophenyl}-5-oxo-5,6-dihydro-4H-[1,3,4]thiadiazine-6-carboxylic acid methyl ester

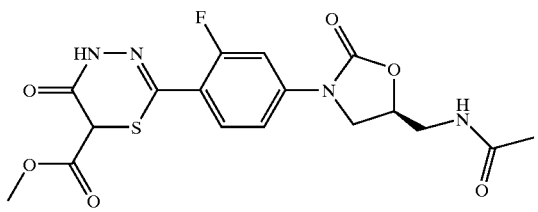

Prepared from 2-[4-(5(S)-aminomethyl-2-oxo-oxazolidin-3-yl)-2-fluorophenyl]-5-oxo-5,6-dihydro-4H-[1,3,4]thiadiazine-6-carboxylic acid methyl ester, trifluoroacetate salt according to the method of Example 2 (0.030 g, 40%); $^1$H NMR (300 MHz, DMSO-d$_6$) δ 1.83 (s, 3H), 3.17 (s, 3H), 3.43 (t, J=5.1 Hz, 2H), 3.70–3.79 (m, 2H), 4.15 (t, J=9.0 Hz, 1H), 4.76–4.77 (m, 1H), 7.36–7.69 (m, 3H), 8.25 (t, J=5.4 Hz, 1H); foam; MS (m/z): [M+H]$^+$=425.

The intermediates for this compound are prepared as follows:

I. 2-[4-(5(S)-Aminomethyl-2-oxo-oxazolidin-3-yl)-2-fluorophenyl]-5-oxo-5,6-dihydro-4H-[1,3,4]thiadiazine-6-carboxylic acid methyl ester, trifluoroacetate salt

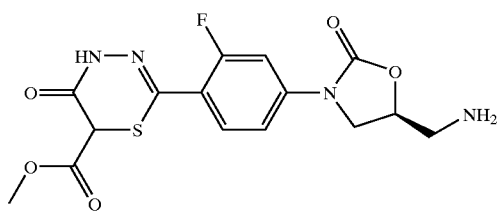

Prepared from 2-[{4-[5(S)-(tert-butoxycarbonylaminomethyl)-2-oxo-oxazolidin-3-yl]-2-fluorophenyl}-(tert-butoxycarbonylhydrazono)-methylsulfanyl]-malonic acid dimethyl ester according to the method of Example 2, Intermediate I; MS (m/z): [M+H]$^+$=497.

II. 2-[{4-[5(S)-(tert-Butoxycarbonylaminomethyl)-2-oxo-oxazolidin-3-yl]-2-fluorophenyl}-(tert-butoxycarbonylhydrazono)-methylsulfanyl]-malonic acid dimethyl ester

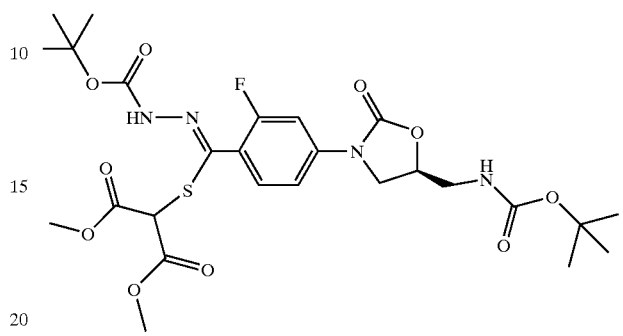

Prepared from dimethyl bromomalonate (0.030 ml, 0.227 mmol) and N'-{4-[5(S)-(tert-butoxycarbonylaminomethyl)-2-oxo-oxazolidin-3-yl]-2-fluorothiobenzoyl}-hydrazinecarboxylic acid tert-butyl ester (0.100 g, 0.206 mmol) according to the procedure of Example 1, Intermediate II (0.11 g, 83%); MS (m/z): [M+H]$^+$=615.

Example 14

N-(3-{3-Fluoro-4-(6-(4-hydroxyphenyl)-5-oxo-5,6-dihydro-4H-[1,3,4]thiadiazin-2-yl]-phenyl}-2-oxo-oxazolidin-5(S)-ylmethyl)-acetamide

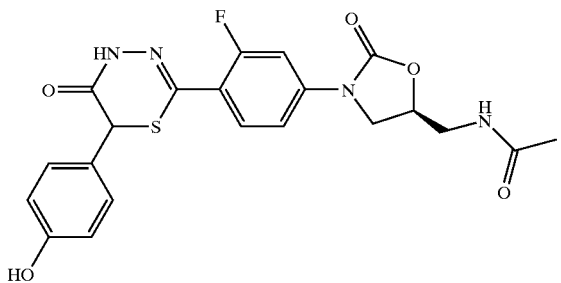

25% Sodium methoxide solution in methanol (0.027 ml, 0.117 mmol) is added to methanesulfonic acid 4-(2-{4-[5-(acetylaminomethyl)-2-oxo-oxazolidin-3-yl]-2-fluorophenyl}-5-oxo-5,6-dihydro-4H-[1,3,4]thiadiazin-6-yl)-phenyl ester (0.050 g, 0.0932 mmol) in methanol (2 ml) and the mixture is stirred at room temperature overnight. The reaction mixture is neutralized with acetic acid (0.020 ml), evaporated to dryness and the residue is purified by PTLC (10% MeOH/DCM) to give product as a white solid (0.039 g, 92%); $^1$H NMR (300 MHz, DMSO-d$_6$) δ 1.80 (s, 3H), 3.40–3.45 (bs, 2H), 3.74 (dd, J=6.9, 10.5 Hz, 1H), 4.12 (t, J=9.3 Hz, 1H), 4.70–4.79 (m, 1H), 4.98 (s, 3H), 6.73 (d, J=8.4 Hz, 2H), 7.08 (d, J=8.7 Hz, 1H), 7.37 (dd, J=1.8, 8.7 Hz, 1H), 7.55–7.60 (m, 2H), 8.25 (t, J=5.7 Hz, 1H); mp >200 (decomp.); MS (m/z): [M+H]$^+$=459.

The intermediates for this compound are prepared as follows:

I. Methanesulfonic acid 4-(2-{4-[5(S)-(acetylaminomethyl)-2-oxo-oxazolidin-3-yl]-2-fluorophenyl}-5-oxo-5,6-dihydro-4H-[1,3,4]thiadiazin-6-yl)-phenyl ester

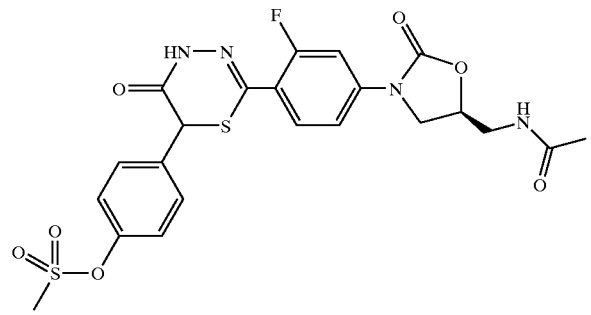

Prepared from methanesulfonic acid 4-{2-[4-(5(S)-aminomethyl-2-oxo-oxazolidin-3-yl)-2-fluorophenyl]-5-oxo-5,6-dihydro-4H-[1,3,4]thiadiazin-6-yl}-phenyl ester, trifluoroacetate salt according to the method of Example 2 (0.064 g, 76%). MS (m/z): [M+H]$^+$=537.

II. Methanesulfonic acid 4-{2-[4-(5(S)-aminomethyl-2-oxo-oxazolidin-3-yl)-2-fluorophenyl]-5-oxo-5,6-dihydro-4H-[1,3,4]thiadiazin-6-yl}-phenyl ester, trifluoroacetate salt

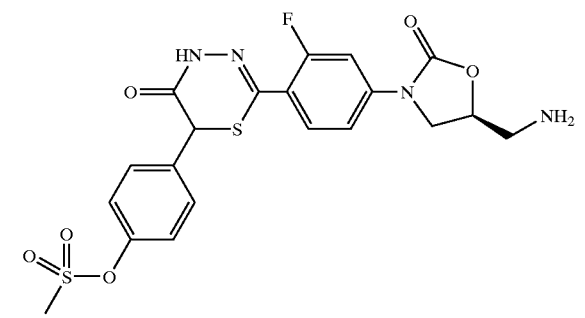

Prepared from [{4-[5(S)-(tert-butoxycarbonylaminomethyl)-2-oxo-oxazolidin-3-yl]-2-fluorophenyl}-(tert-butoxycarbonylhydrazono)-methylsulfanyl]-(4-methanesulfonyloxyphenyl)-acetic acid ethyl ester according to the method of Example 2, Intermediate I. MS (m/z): [M+H]$^+$=609.

III. [{4-[5(S)-(tert-Butoxycarbonylaminomethyl)-2-oxo-oxazolidin-3-yl]-2-fluorophenyl}-(tert-butoxycarbonylhydrazono)-methylsulfanyl]-(4-methanesulfonyloxyphenyl)-acetic acid ethyl ester

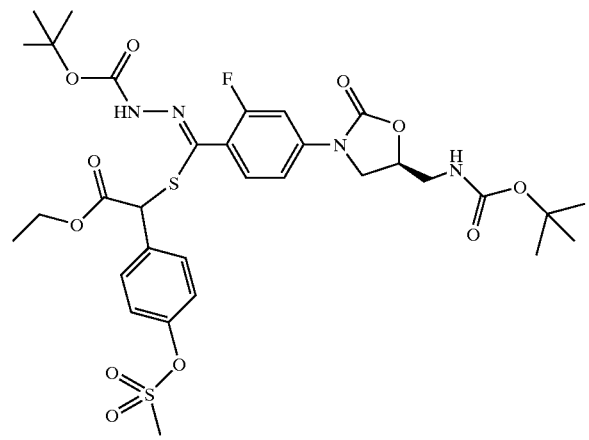

Prepared from methanesulfonyloxy(4-methanesulfonyloxyphenyl)-acetic acid methyl ester (0.080 g, 0.227 mmol) and N'-{4-[5(S)-(tert-butoxycarbonylaminomethyl)-2-oxo-oxazolidin-3-yl]-2-fluorothiobenzoyl}-hydrazinecarboxylic acid tert-butyl ester (0.100 g, 0.206 mmol) according to the procedure of Example 1, Intermediate II (0.118 g, 77%). MS (m/z): [M+H]$^+$=741.

IV. Methanesulfonyloxy(4-methanesulfonyloxyphenyl)-acetic acid methyl ester

Methanesulfonyl chloride (0.395 ml, 5.10 mmol) is added dropwise at 0° C. to ethyl 4-hydroxymandelate (0.500 g, 2.55 mmol) and triethylamine (0.889 ml, 6.38 mmol) in DMF (5 ml) and the mixture is allowed to warm to room temperature overnight. The reaction mixture is diluted with water and extracted with ethyl acetate. The extract is washed with brine, dried (MgSO$_4$), and evaporated to give oily residue which is purified by flash column chromatography (30% EtOAc/Hexane) (0.75 g, 82%). MS (m/z): [M+H]$^+$=353.

Example 15

N-{3-[3-Fluoro-4-(5-oxo-5,6-dihydro-4H-[1,3,4]thiadiazin-2-yl)-phenyl]-2-oxo-oxazolidin-5(S)-ylmethyl}-propionamide

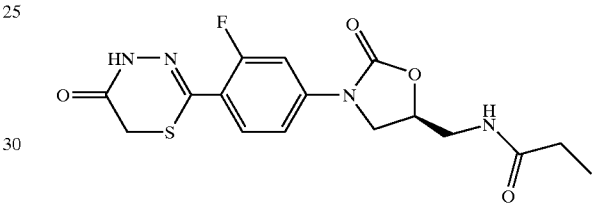

1,3-Dicyclohexylcarbodiimide (0.153 g, 0.740 mmol) is added to a mixture of 2-[4-(5(S)-aminomethyl-2-oxo-oxazolidin-3-yl)-2-fluorophenyl]-4H-[1,3,4]thiadiazin-5-one (0.200 g, 0.617 mmol), N,N-diisopropylethylamine (0.161 ml, 0.927 mmol) and propionic acid (0.051 ml, 0.680 mmol) in DMF (3 ml). The mixture is stirred overnight at room temperature and then partially evaporated under vacuum. The residue is diluted with water (5 ml) and the resulting precipitate is filtered and dried under vacuum. Purification by PTLC (10% MeOH/DCM) gives pure product as a white solid (0.21 g, 90%); $^1$HNMR (300 MHz, DMSO-d$_6$) δ 0.94 (t, J=7.7 Hz, 3H), 2.08 (q, J=7.7 Hz, 2H), 3.40–3.48 (m, 2H), 3.59 (s, 2H), 3.77 (dd, J=6.0, 9.1 Hz, 1H), 4.14 (t, J=9.1 Hz, 1H), 4.74–4.78 (m, 1H), 7.41 (dd, J=2.2, 8.8 Hz, 1H), 7.52 (dd, J=2.2, 14 Hz, 1H), 7.69 (t, J=8.5 Hz, 1H), 8.16 (t, J=5.8 Hz, 1H), 11.6 (s, 1H); mp 192–3; MS (m/z): [M+H]$^+$=381.

Example 16

Cyclopropanecarboxylic acid {3-[3-fluoro-4-(5-oxo-5,6-dihydro-4H-[1,3,4]thiadiazin-2-yl)-phenyl]-2-oxo-oxazolidin-5(S)-ylmethyl}-amide

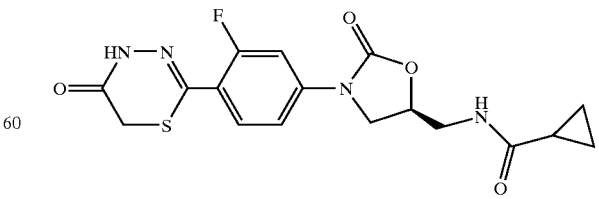

Prepared from 2-[4-(5(S)-aminomethyl-2-oxo-oxazolidin-3-yl)-2-fluorophenyl]-4H-[1,3,4]thiadiazin-5-one (0.30 g, 0.925 mmol and cyclopropanecarboxylic acid (0.0812 ml, 1.02 mmol) according to the method of Example 15 (0.30 g, 84%); ¹HNMR (300 MHz, DMSO-d₆) δ 0.59–0.68 (m, 4H), 1.53–1.62 (m, 1H), 3.44 (t, J=5.2 Hz, 2H), 3.58 (s, 2H), 3.72 (dd, J=6.3, 9.1 Hz, 1H), 4.14 (t, J=9.1 Hz, 1H), 4.72–4.78 (m, 1H), 7.41 (dd, J=2.2, 8.5 Hz, 1H), 7.53 (dd, J=2.2, 14 Hz, 1H), 7.68 (t, J=8.8 Hz, 1H), 8.46 (t, J=5.8 Hz, 1H), 11.6 (s, 1H); mp 239–40; MS (m/z): [M+H]⁺=393.

Example 17

N-{3-[3-Fluoro-4-(5-oxo-5,6-dihydro-4H-[1,3,4]thiadiazin-2-yl)-phenyl]-2-oxo-oxazolidin-5(S)-ylmethyl}-2-hydroxyacetamide

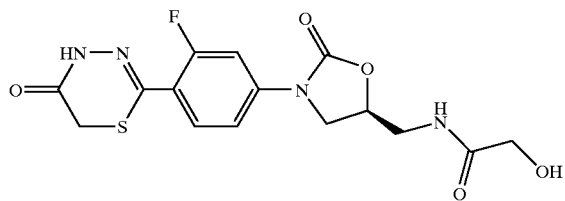

Prepared from 2-[4-(5(S)-aminomethyl-2-oxo-oxazolidin-3-yl)-2-fluorophenyl]-4H-[1,3,4]thiadiazin-5-one (0.300 g, 0.925 mmol) and acetoxyacetic acid (0.120 g, 1.02 mmol) according to the method of Example 15. The crude product is deacetylated by dissolving in 0.1M LiOH in methanol (10 ml) and stirring for 2 hours at room temperature. The reaction mixture is neutralized with acetic acid, evaporated under vacuum, and the residue is purified by PTLC to give product as a white solid (0.27 g, 78%); ¹HNMR (300 MHz, DMSO-d₆) δ 3.39–3.54 (m, 2H), 3.59 (s, 2H), 3.82–3.87 (m, 3H), 4.14 (t, J=9.1 Hz, 1H), 4.75–4.83 (m, 1H), 5.53 (t, J=5.5 Hz, 1H), 7.38 (dd, J=2.2, 8.5 Hz, 1H), 7.52 (dd, J=2.2, 14 Hz, 1H), 7.69 (t, J=8.8 Hz, 1H), 8.07 (t, J=6.0 Hz, 1H), 11.6 (s, 1H); mp 157–8; MS (m/z): [M+H]⁺=383.

Example 18

{3-[3-Fluoro-4-(5-oxo-5,6-dihydro-4H-[1,3,4]thiadiazin-2-yl)-phenyl]-2-oxo-oxazolidin-5(S)-ylmethyl}-urea

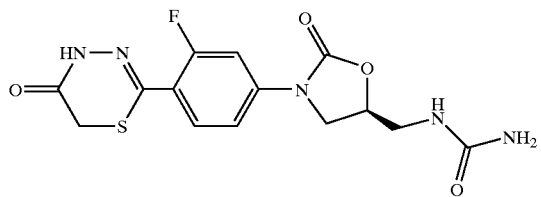

Trimethylsilyl isocyanate (0.138 ml, 1.02 mmol) is added to a mixture of 2-[4-(5(S)-aminomethyl-2-oxo-oxazolidin-3-yl)-2-fluorophenyl]-4H-[1,3,4] thiadiazin-5-one (0.30 g, 0.925 mmol) in THF (10 ml). The mixture is stirred at room temperature overnight and then is evaporated to dryness. The residue is purified by PTLC (10% MeOH/DCM) to give product as a white solid (0.22 g, 65%); ¹HNMR (300 MHz, DMSO-d₆) δ 3.29–3.36 (m, 2H), 3.59 (s, 2H), 3.78 (dd, J=6.3, 9.1 Hz, 1H), 4.13 (t, J=9.1 Hz, 1H), 4.69–4.77 (m, 1H), 5.58 (s, 1H), 6.31 (t, J=6.0 Hz, 1H), 7.42 (dd, J=2.2, 8.8 Hz, 1H), 7.59 (dd, J=2.2, 14 Hz, 1H), 7.68 (t, J=8.8 Hz, 1H), 11.6 (s, 1H); mp 235–6; MS (m/z): [M+H]⁺=368.

Example 19

N-{3-[3-Fluoro-4-(5-oxo-5,6-dihydro-4H-[1,3,4]thiadiazin-2-yl)-phenyl]-2-oxo-oxazolidin-5(S)-ylmethyl-carbamic acid methyl ester

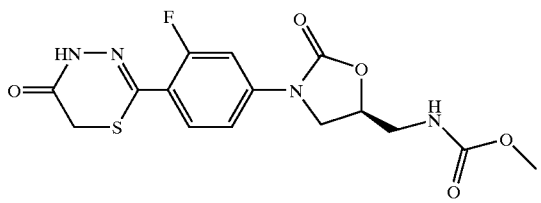

Methyl chloroformate (0.0786 ml, 1.02 mmol) is added dropwise at 0° C. to 2-[4-(5(S)-aminomethyl-2-oxo-oxazolidin-3-yl)-2-fluorophenyl]-4H-[1,3,4]thiadiazin-5-one (0.300 g, 0.925 mmol) and triethylamine (0.193 ml, 1.39 mmol) in THF (10 ml) and the mixture is stirred at 0° C. for 10 minutes and then is allowed to warm to room temperature. The reaction mixture is evaporated to dryness and the residue is purified by PTLC (10% MeOH/DCM) to give product as a white solid (g, 0.29 g, 82%); ¹HNMR (300 MHz, DMSO-d₆) δ 3.35 (t, J=5.5 Hz, 2H), 3.52 (s, 3H), 3.59 (s, 2H), 3.80 (dd, J=6.3, 9.1 Hz, 1H), 4.15 (t, J=9.1 Hz, 1H), 4.70–4.79 (m, 1H), 7.38 (dd, J=2.2, 8.5 Hz, 1H), 7.52 (dd, J=2.2, 14 Hz, 1H), 7.69 (t, J=8.8 Hz, 1H), 8.07 (t, J=6.0 Hz, 1H), 11.6 (s, 1H); mp 210; MS (m/z): [M+H]⁺=383.

Example 20

N-{3-[3-Fluoro-4-(5-oxo-5,6-dihydro-4H-[1,3,4]thiadiazin-2-yl)-phenyl]-2-oxo-oxazolidin-5(S)-ylmethyl}-carbamic acid tert-butyl ester

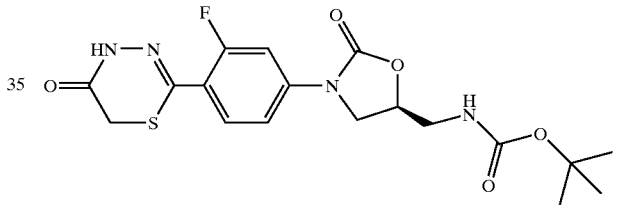

Di-tert-butyl dicarbonate (0.223 ml, 0.971 mmol) is added to 2-[4-(5(S)-aminomethyl-2-oxo-oxazolidin-3-yl)-2-fluorophenyl]-4H-[1,3,4]thiadiazin-5-one (0.300 g, 0.925 mmol) and pyridine (0.112 ml, 1.39 mmol) in DMF (3 ml) and is stirred overnight at room temperature. The reaction mixture is evaporated to dryness and the residue is purified by PTLC (10% MeOH/DCM) to give a white solid (0.37 g, 94%); ¹HNMR (300 MHz, DMSO-d₆) δ 1.34 (s, 9H), 3.27 (t, J=5.5 Hz, 2H), 3.59 (s, 2H), 3.82 (dd, J=6.6, 9.3 Hz, 1H), 4.14 (t, J=9.1 Hz, 1H), 4.69–4.77 (m, 1H), 7.23 (t, J=5.5 Hz, 1H), 7.42 (dd, J=2.2, 8.8 Hz, 1H), 7.57 (dd, J=1.9, 14 Hz, 1H), 7.68 (t, J=8.8 Hz, 1H), 11.6 (s, 1H); mp 167–8; MS (m/z): [M+H]⁺=425.

Example 21

N-{3-[3-Fluoro-4-(5-oxo-5,6-dihydro-4H-[1,3,4]thiadiazin-2-yl)-phenyl]-2-oxo-oxazolidin-5(S)-ylmethyl}-3-oxo-butyramide

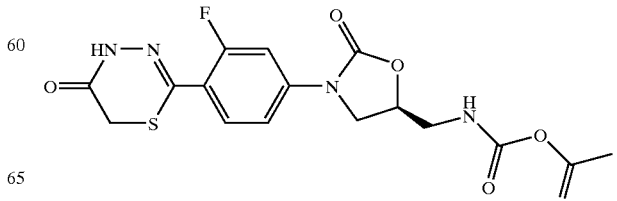

Diketene (0.0590 ml, 0.648 mmol) is added dropwise to a solution of 2-[4-(5(S)-aminomethyl-2-oxo-oxazolidin-3-yl)-2-fluorophenyl]-4H-[1,3,4]thiadiazin-5-one (0.200 g, 0.617 mmol) and triethylamine (0.0946 ml, 0.679 mmol) in DMF (2 ml) and is stirred overnight at room temperature. The reaction mixture is evaporated to dryness and the residue is purified by PTLC (10% MeOH/DCM) to give a white solid (0.22 g, 89%); $^1$HNMR (300 MHz, DMSO-$d_6$) δ 2.08 (s, 3H), 3.34 (s, 2H), 3.42–3.54 (m, 2H), 3.59 (s, 2H), 3.78 (dd, J=6.3, 9.1 Hz, 1H), 4.14 (t, J=9.1 Hz, 1H), 4.75–4.83 (m, 1H), 7.37 (dd, J=2.2, 8.5 Hz, 1H), 7.52 (dd, J=2.2, 14 Hz, 1H), 7.69 (t, J=8.8 Hz, 1H), 8.45 (t, J=5.8 Hz, 1H), 11.6 (s, 1H); mp 176–8; MS (m/z): [M+H]$^+$=409.

Example 22

N-{3-[3-Fluoro-4-(5-oxo-5,6-dihydro-4H-[1,3,4]thiadiazin-2-yl)-phenyl]-2-oxo-oxazolidin-5(S)-ylmethyl}-3-(4-fluorophenyl)-3-oxo-propionamide

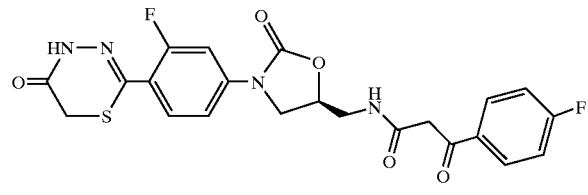

2-[4-(5(S)-Aminomethyl-2-oxo-oxazolidin-3-yl)-2-fluorophenyl]-4H-[1,3,4]thiadiazin-5-one (0.100 g, 0.308 mmol), methyl fluorobenzoylacetate (0.052 ml, 0.323 mmol), and potassium cyanide (5 mg, 0.077 mmol) are mixed together in DMF and heated at 85° C. for 45 minutes. The reaction mixture is evaporated to dryness and the residue is purified by PTLC (10% MeOH/DCM) to give product as a white solid (0.030 g, 20%); $^1$HNMR (300 MHz, DMSO-$d_6$) δ 3.41–3.54 (m, 2H), 3.59 (s, 2H), 3.74 (dd, J=6.3, 9.3 Hz, 1H), 3.87–4.01 (m, 2H), 4.12 (t, J=9.1 Hz, 1H), 4.76–4.84 (m, 1H), 7.25–7.33 (m, 2H), 7.38 (dd, J=2.2, 8.8 Hz, 1H), 7.55 (dd, J=1.9, 14 Hz, 1H), 7.65 (t, J=8.8 Hz, 1H), 7.95–8.00 (m, 2H), 8.59 (t, J=5.8 Hz, 1H), 11.6 (s, 1H); mp 184–7; MS (m/z): [M+H]$^+$=489.

Example 23

N-{3-[3-Fluoro-4-(5-oxo-5,6-dihydro-4H-[1,3,4]thiadiazin-2-yl)-phenyl]-2-oxo-oxazolidin-5(S)-ylmethyl}-3-[4-(hydroxyimino-methyl)-phenyl]-acrylamide

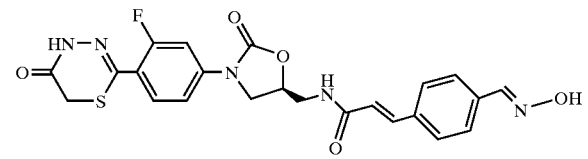

Hydroxylamine hydrochloride (0.0106 g, 0.152 mmol) is added to N-{3-[3-fluoro-4-(5-oxo-5,6-dihydro-4H-[1,3,4]thiadiazin-2-yl)-phenyl]-2-oxo-oxazolidin-5(S)-ylmethyl}-3-(4-formyl-phenyl)-acrylamide (0.076 g, 0.145 mmol) dissolved in pyridine (3 ml) and is stirred overnight at room temperature. The reaction mixture is evaporated to dryness and the residue is purified by PTLC (10% MeOH/DCM) to give pure product as a white solid (0.065 g, 90%); $^1$H NMR (300 MHz, DMSO-$d_6$) δ 3.59 (bs, 4H), 3.83 (dd, J=6.3, 11.7 Hz, 1H), 4.20 (t, J=9.3 Hz, 1H), 4.80–4.90 (m, 1H), 6.70 (d, J=15.6 Hz, 1H), 7.42–7.72 (m, 8H), 8.15 (s, 1H), 8.54 (t, J=5.4 Hz, 1H); mp 144–5; MS (m/z): [M+H]$^+$=498.

The intermediate for the synthesis of above compound is prepared as follows:

I. N-{3-[3-Fluoro-4-(5-oxo-5,6-dihydro-4H-[1,3,4]thiadiazin-2-yl)-phenyl]-2-oxo-oxazolidin-5(S)-ylmethyl}-3-(4-formyl-phenyl)-acrylamide

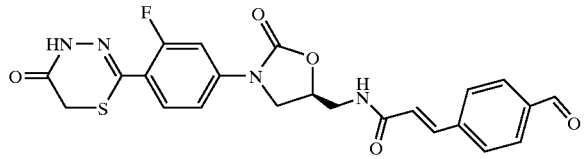

N,N-Diisopropylethylamine (0.169 ml, 0.972 mmol) is added to 4-formylcinnamic acid (0.057 g, 0.324 mmol) and O-(7-azabenzotriazol-1-yl)-N,N,N',N'-tetramethyluronium hexafluorophosphate (0.129 g, 0.340 mmol) in DMF (2 ml) and is stirred for 20 minutes at room temperature. 2-[4-(5(S)-aminomethyl-2-oxo-oxazolidin-3-yl)-2-fluorophenyl]-4H-[1,3,4]thiadiazin-5-one (0.100 g, 0.308 mmol) is added and stirring is continued at room temperature overnight. The reaction mixture is partially evaporated under vacuum and the residue is diluted with water (5 ml). The resulting precipitate is filtered and dried under vacuum to give crude product used directly in the next step (0.076 g, 51%). MS (m/z): [M+H]$^+$=483.

Example 24

N-{3-[3-Fluoro-4-(5-oxo-5,6-dihydro-4H-[1,3,4]thiadiazin-2-yl)-phenyl]-2-oxo-oxazolidin-5(S)-ylmethyl}-3-[4-(methoxyimino-methyl)-phenyl]-acrylamide

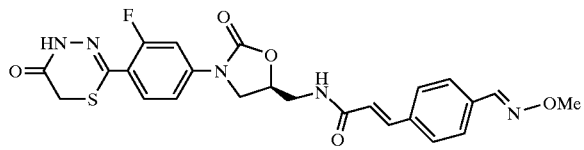

N,N-Diisopropylethylamine (0.160 ml, 1.15 mmol) is added to 3-[4-(methoxyimino-methyl)-phenyl]-acrylic acid (0.0786 g, 0.383 mmol) and O-(7-azabenzotriazol-1-yl)-N,N,N',N'-tetramethyluronium hexafluorophosphate (0.152 g, 0.402 mmol) in DMF (3 ml) and is stirred for 20 minutes at room temperature. 2-[4-(5(S)-aminomethyl-2-oxo-oxazolidin-3-yl)-2-fluorophenyl]-4H-[1,3,4]thiadiazin-5-one (0.118 g, 0.365 mmol) is added and stirring is continued at room temperature overnight. The reaction mixture is partially evaporated under vacuum and the residue diluted with water (5 ml). The resulting precipitate is filtered and dried under vacuum. Purification by PTLC (10% MeOH/DCM) gives pure product as a white solid (0.080 g, 43%); $^1$H NMR (300 MHz, DMSO-$d_6$) δ 3.59 (bs, 4H), 3.82 (dd, J=6.9, 9.3 Hz, 1H), 3.90 (s, 3H), 4.20 (t, J=9.0 Hz, 1H), 4.83–4.87 (m, 1H), 6.73 (d, J=15.9 Hz, 1H), 7.42–7.72 (m, 8H), 8.24 (s, 1H), 8.55 (t, J=5.7 Hz, 1H), mp 175 (decomp); MS (m/z): [M+H]$^+$=512.

The intermediate for the synthesis of above compound is prepared as follows:

I. 3-[4-(Methoxyimino-methyl)-phenyl]-acrylic acid

Methoxylamine hydrochloride (0.996 g, 0.0119 mol) is added to a solution of formylcinnamic acid (2 g, 0.0114 mol) in pyridine (20 ml) and is stirred for 2 hours. The reaction mixture is evaporated under vacuum and the residue is diluted with 2N aqueous HCl. The resulting precipitate is filtered and dried under vacuum (2.00 g, 85%).

Example 25
N-{3-[3-Fluoro-4-(5-oxo-5,6-dihydro-4H-[1,3,4]thiadiazin-2-yl)-phenyl]-2-oxo-oxazolidin-5(S)-ylmethyl}-thioacetamide

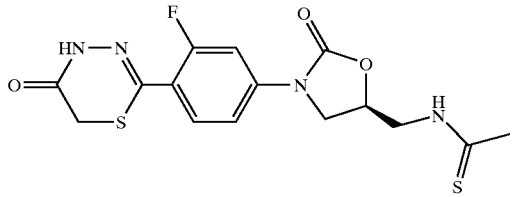

Ethyl dithioacetate (0.0708 ml, 0.747 mmol) is added to 2-[4-(5(S)-aminomethyl-2-oxo-oxazolidin-3-yl)-2-fluorophenyl]-4H-[1,3,4]thiadiazin-5-one (0.200 g, 0.617 mmol) and triethylamine (0.0946 ml, 0.679 mmol) in DMF (3 ml) and is stirred at room temperature overnight. The reaction mixture is evaporated to dryness and the residue is purified by PTLC (10% MeOH/DCM) to give a white solid (0.21 g, 90%); $^1$HNMR (300 MHz, DMSO-$d_6$) δ 2.43 (s, 3H), 3.59 (s, 2H), overlapping 3.84 (dd, J=6.6, 9.1, 2H) and 3.92 (t, J=4.7 Hz, 2H), 4.19 (t, J=9.1 Hz, 1H), 4.92–5.05 (m, 1H), 7.43 (dd, J=2.2, 8.5 Hz, 1H), 7.58 (dd, J=2.2, 14, 1H), 7.69 (t, J=8.5, 1H), 10.4 (t, J=5.8 Hz, 1H), 11.6 (s, 1H); mp 182–3; MS (m/z): [M+H]$^+$=383.

Example 26
N-{3-[3-Fluoro-4-(5-thioxo-5,6-dihydro-4H-[1,3,4]thiadiazin-2-yl)-phenyl]-2-oxo-oxazolidin-5(S)-ylmethyl}-thioacetamide

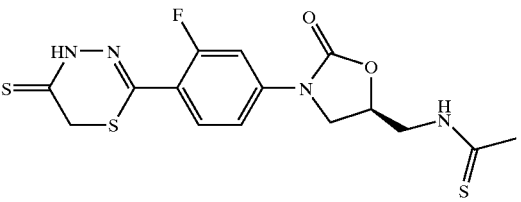

Lawesson's reagent (0.232 g, 0.573 mmol) and N-{3-[3-fluoro-4-(5-oxo-5,6-dihydro-4H-[1,3,4]thiadiazin-2-yl)-phenyl]-2-oxo-oxazolidin-5(S)-ylmethyl}-acetamide (0.200 g, 0.546 mmol) in dioxane (5 ml) are heated at 65° C. for 6 hours. The reaction mixture is evaporated to dryness and the residue is purified by PTLC (10% MeOH/DCM) to give a bright yellow solid (0.16 g, 75%); $^1$HNMR (300 MHz, DMSO-$d_6$) δ 2.43 (s, 3H), 3.85 (dd, J=6.9, 9.3 Hz, 2H), 3.92 (t, 5.7 Hz, 2H), 4.01 (s, 2H), 4.20 (t, J=9.1 Hz, 1H), 4.94–5.03 (m, 1H), 7.47 (dd, J=2.2, 8.8 Hz, 1H), 7.61 (dd, J=2.2, 14 Hz, 1H), 7.74 (t, J=8.8 Hz, 1H), 10.4 (t, J=5.2 Hz, 1H); mp 158–61; MS (m/z): [M+H]$^+$=399.

Example 27
N-{3-[3-Fluoro-4-(5-thioxo-5,6-dihydro-4H-[1,3,4]thiadiazin-2-yl)-phenyl]-2-oxo-oxazolidin-5(S)-ylmethyl}-acetamide

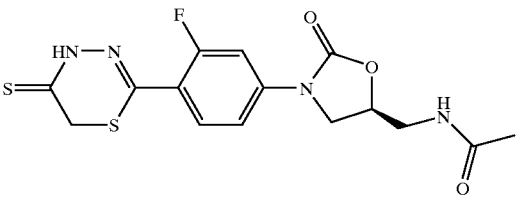

5(S)-Aminomethyl-3-[3-fluoro-4-(5-thioxo-5,6-dihydro-4H-[1,3,4]thiadiazin-2-yl)-phenyl]-oxazolidin-2-one, trifluoroacetate salt is dissolved in pyridine and acetic anhydride (0.0163 ml, 0.173 mmol) is added. The reaction is stirred at room temperature for 4 hours and then evaporated to dryness. The residue is purified by PTLC (10% MeOH/DCM) to give product.

The intermediate for the synthesis of above compound is prepared as follows:

I. 5(S)-Aminomethyl-3-[3-fluoro-4-(5-thioxo-5,6-dihydro-4H-[1,3,4]thiadiazin-2-yl)-phenyl]-oxazolidin-2-one trifluoroacetate salt

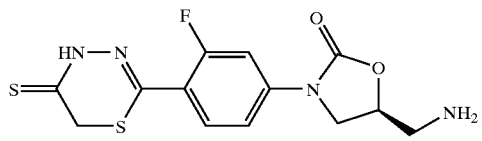

20% Trifluoroacetic acid/dichloromethane (2 ml) is added to {3-[3-fluoro-4-(5-thioxo-5,6-dihydro-4H-[1,3,4]thiadiazin-2-yl)-phenyl]-2-oxo-oxazolidin-5(S)-ylmethyl}-carbamic acid tert-butyl ester and the mixture is stirred at room temperature for 30 minutes. The reaction is evaporated to dryness and the trifluoroacetate salt is used directly in the next step.

Example 28
N-{3-[3-Fluoro-4-(5-thioxo-5,6-dihydro-4H-[1,3,4]thiadiazin-2-yl)-phenyl]-2-oxo-oxazolidin-5(S)-ylmethyl}-carbamic acid tert-butyl ester

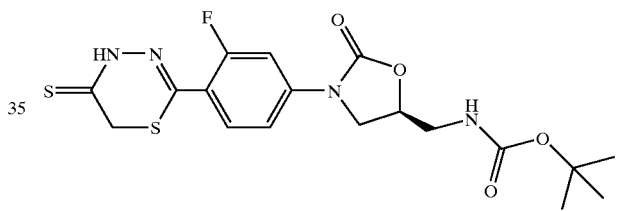

Lawesson's reagent (0.0715 g, 0.177 mmol) and {3-[3-fluoro-4-(5-oxo-5,6-dihydro-4H-[1,3,4]thiadiazin-2-yl)-phenyl]-2-oxo-oxazolidin-5(S)-ylmethyl}-carbamic acid tert-butyl ester (0.100 g, 0.236 mmol) in dioxane (5 ml) are heated at 65° C. for 6 hours. The reaction mixture is evaporated to dryness and the residue is purified by PTLC (10% MeOH/DCM) to give bright yellow solid (0.088 g, 85%); $^1$HNMR (300 MHz, DMSO-$d_6$) δ 1.34 (s, 9H), 3.28 (t, J=5.5 Hz, 2H), 3.82 (dd, J=6.0, 9.1 Hz, 1H), 4.01 (s, 2H), 4.14 (t, J=9.3 Hz, 1H), 4.70–4.78 (m, 1H), 7.24 (t, J=5.8 Hz, 1H), 7.45 (dd, J=2.2, 8.8 Hz, 1H), 7.60 (dd, J=2.2, 14 Hz, 1H), 7.73 (t, J=8.8 Hz, 1H), 8.07 (t, J=6.0 Hz, 1H); mp 134–6; MS (m/z): [M+H]$^+$=441.

Example 29
N-{3-[4-(6,6-Dimethyl-1,5-dioxo-1,4,5,6-tetrahydro-1λ$^4$-[1,3,4]-thiadiazin-2-yl)-3-fluorophenyl]-2-oxo-oxazolidin-5(S)-ylmethyl}-acetamide

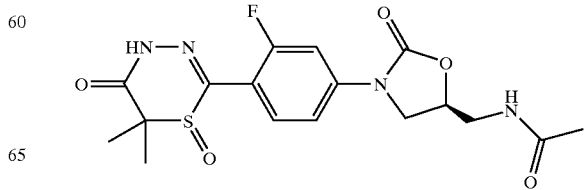

m-Chloroperoxybenzoic acid (77%, 0.0568 g, 0.254 mmol) is added to N-{3-[4-(6,6-dimethyl-5-oxo-5,6-dihydro-4H-[1,3,4]thiadiazin-2-yl)-3-fluorophenyl]-2-oxo-oxazolidin-5(S)-ylmethyl}-acetamide (0.100 g, 0.254 mmol) in acetic acid (3 ml) and the mixture stirred at room temperature overnight. The reaction mixture is evaporated to dryness and the residue is purified by PTLC (10% MeOH/DCM) to give white solid (0.048 g, 50%); $^1$HNMR (300 MHz, DMSO-$d_6$) δ 1.38 (s, 3H), 1.53 (s, 3H), 1.82 (s, 3H), 3.42 (t, J5.5 Hz, 2H), 3.78 (dd, J=6.6, 9.3 Hz, 1H), 4.17 (t, J=9.1 Hz, 1H), 4.73–4.81 (m, 1H), 7.47–7.51 (m, 1H), 7.63–7.73 (m, 2H), 8.25 (t, J=5.8 Hz, 1H), 12.1 (s, 1H); mp 153–5; $R_f$(10% MeOH/DCM)=0.23; MS (m/z): [M+H]$^+$=383.

Example 30

N-{3-[4-(6,6-Dimethyl-1,1,5-trioxo-1,4,5,6-tetrahydro-1λ$^6$-[1,3,4]thiadiazin-2-yl)-3-fluorophenyl]-2-oxo-oxazolidin-5(S)-ylmethyl}-acetamide

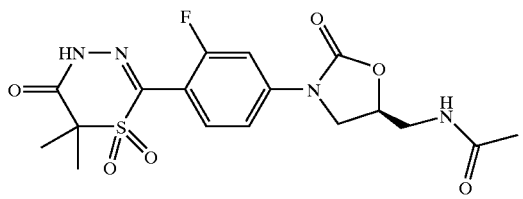

m-Chloroperoxybenzoic acid (77%, 0.114 g, 0.508 mmol) is added to N-{3-[4-(6,6-dimethyl-5-oxo-5,6-dihydro-4H-[1,3,4]thiadiazin-2-yl)-3-fluorophenyl]-2-oxo-oxazolidin-5 (S)-ylmethyl}-acetamide (0.100 g, 0.254 mmol) in acetic acid (3 ml) and the mixture is stirred at 50° C. overnight. The reaction mixture is evaporated to dryness and the residue is purified by PTLC (10% MeOH/DCM) to give white solid (0.073 g, 72%); $^1$HNMR (300 MHz, DMSO-$d_6$) δ 1.50 (s, 6H), 1.82 (s, 3H), 3.42 (t, J=5.5 Hz, 2H), 3.78 (dd, J=6.6, 9.1 Hz, 1H), 4.17 (t, J=9.1 Hz, 1H), 4.72–4.81 (m, 1H), 7.50 (dd, J=1.7, 8.8 Hz, 1H), 7.64–7.70 (m, 2H), 8.24 (t, J=5.8 Hz, 1H); mp 127–8; $R_f$(10% MeOH/DCM)=0.48; MS (m/z): [M+H]$^+$=399.

Example 31

Acetic acid 2-{4-[5(S)-(acetylaminomethyl)-2-oxo-oxazolidin-3-yl]-2-fluorophenyl}-5-oxo-5,6-dihydro-4H-[1,3,4]thiadiazin-6-yl ester

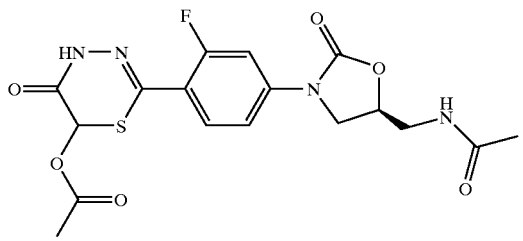

Hydrogen peroxide (30% aqueous sol, 0.0558 ml, 0.546 mmol) is added to N-{3-[3-Fluoro-4-(5-oxo-5,6-dihydro-4H-[1,3,4]thiadiazin-2-yl)-phenyl]-2-oxo-oxazolidin-5(S)-ylmethyl}-acetamide (0.100 g, 0.273 mmol) in acetic acid (2 ml) and is heated at 65° C. overnight. The reaction mixture is evaporated to dryness and the residue is purified by PTLC (10% MeOH/DCM) to give white solid (0.089 g, 82%); $^1$HNMR (300 MHz, DMSO-$d_6$) δ 1.82 (s, 3H), 2.09 (s, 3H), 3.41 (t, J=5.5 Hz, 2H), 3.56 (dd, J=6.6, 9.1 Hz, 1H), 4.14 (t, J=9.1 Hz, 1H), 4.70–4.80 (m, 1H), 7.42 (dd, J=2.2, 8.8 Hz, 1H), 7.59 (dd, J=2.2, 14 Hz, 1H), 7.65 (t, J=8.5 Hz, 1H), 8.25 (t, J=5.8 Hz, 1H); mp 174–7; MS (m/z): [M+H]$^+$=425.

Example 32

N-{3-[3-Fluoro-4-(4-methyl-5-oxo-5,6-dihydro-[1,3,4]thiadiazin-2-yl)-phenyl]-2-oxo-oxazolidin-5(S)-ylmethyl}-acetamide

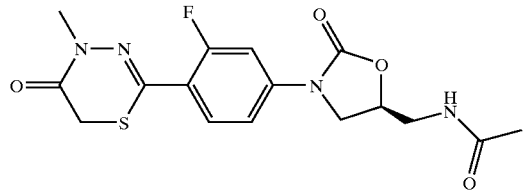

A mixture of N-{3-[3-fluoro-4-(5-oxo-5,6-dihydro-4H-[1,3,4]thiadiazin-2-yl)-phenyl]-2-oxo-oxazolidin-5(S)-ylmethyl}-acetamide (0.100 g, 0.273 mmol), potassium carbonate (0.075 g, 0.546 mmol), and iodomethane (0.0187 ml, 0.300 mmol) in DMF (3 ml) is heated at 80° C. overnight. The reaction mixture is filtered and evaporated to dryness. The residue is purified by PTLC (10% MeOH/DCM) to give product as a white solid (0.104 g, 90%); $^1$HNMR (300 MHz, DMSO-$d_6$) δ 1.82 (s, 3H), 3.39 (s, 3H), 3.42 (t, J=5.5, 2H), 3.66 (s, 2H), 3.76 (dd, J=6.6, 9.3 Hz, 1H), 4.14 (t, J=9.1 Hz, 1H), 4.71–4.80 (m, 1H), 7.43 (dd, J=2.2, 8.8 Hz, 1H), 7.59 (dd, J=1.9, 14 Hz, 1H), 7.72 (t, J=8.8 Hz, 1H), 8.25 (t, J=5.8 Hz, 1H); mp 179–80; MS (m/z): [M+H]$^+$=381.

Example 33

(2–14-[5(S)-(Acetylaminomethyl)-2-oxo-oxazolidin-3-yl]-2-fluorophenyl}-5-oxo-5,6-dihydro-[1,3,4]thiadiazin-4-yl)-acetic acid methyl ester

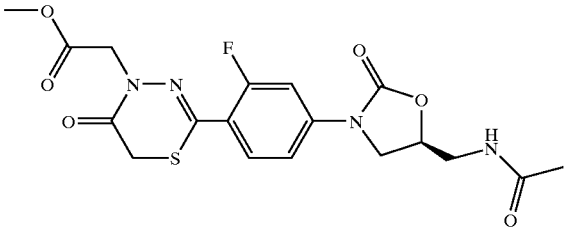

Prepared from N-{3-[3-fluoro-4-(5-oxo-5,6-dihydro-4H-[1,3,4]thiadiazin-2-yl)-phenyl]-2-oxo-oxazolidin-5(S)-ylmethyl}-acetamide (0.100 g, 0.273 mmol), potassium carbonate (0.075 g, 0.546 mmol), and methyl bromoacetate (0.0284 ml, 0.300 mmol) according to the procedure of Example 32 (0.062 g, 60%); $^1$HNMR (300 MHz, DMSO-$d_6$) δ 1.82 (s, 3H), 3.39–3.44 (m, 2H), 3.67 (s, 3H), overlapping 3.74–3.79 (m, 1H) and 3.75 (s, 2H), 4.14 (t, J=9.1 Hz, 1H), 4.61 (s, 2H), 4.71–4.80 (m, 1H), 7.42 (dd, J=2.2, 8.8 Hz, 1H), 7.59 (dd, J=2.2, 14 Hz, 1H), 7.70 (t, J=8.5 Hz, 1H), 8.25 (t, J=5.8 Hz, 1H); mp 157–8; MS (m/z): [M+H]$^+$=439.

Example 34

2-[2-Fluoro-4-(5(R)-hydroxymethyl)-2-oxo-oxazolidin-3-yl)-phenyl]-4H-[1,3,4]thiadiazin-5-one

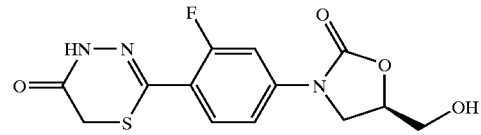

tert-Butyl nitrite (0.557 ml, 4.69 mmol) is added dropwise at room temperature to 2-[4-(5(S)-aminomethyl-2-oxo-oxazolidin-3-yl)-2-fluorophenyl]-4H-[1,3,4]thiadiazin-5-one (0.304 g, 0.938 mmol) and acetic acid (2 ml) in 1,4-dioxane (20 ml) and the mixture is stirred for 1 hour. The reaction mixture is evaporated to dryness and the residue is dissolved in a mixture of DMF (3 ml) and methanol (20 ml). A 0.1 M solution of lithium hydroxide in methanol (12 ml, 1.2 mmol) is added and the mixture is stirred for 30 minutes at room temperature. Acetic acid is added until neutral and the mixture is evaporated to dryness. The residue is purified by PTLC (10% MeOH/DCM) δ give product as a white solid (0.170 g, 56%); ¹HNMR (300 MHz, DMSO-d₆) δ overlapping 3.52–3.60 (m, 1H) and 3.59 (s, 2H), 3.66–3.71 (m, 1H), 3.85 (dd, J=6.3, 9.1, 2H), 4.11 (t, J=9.1 Hz, 1H), 4.68–4.79 (m, 1H), 5.24 (t, J=5.5 Hz, 1H), 7.46 (dd, J=2.2, 8.5 Hz, 1H), 7.60 (dd, J=2.2, 14, 1H), 7.68 (t, J=8.5, 11H), 11.6 (s, 1H); mp 224–7; MS (m/z): [M+H]⁺=326.

Example 35
2-{2-Fluoro-4-[5(S)-(isoxazol-3-ylaminomethyl)-2-oxo-oxazolidin-3-yl]-phenyl}-4H-[1,3,4]thiadiazin-5-one

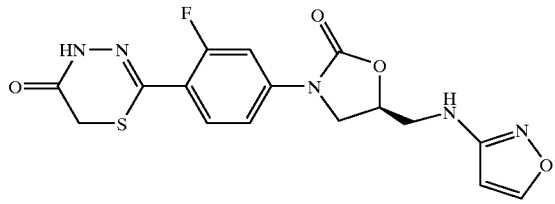

Zinc dust (0.115 g, 1.76 mmol) is added to {3-[3-Fluoro-4-(5-oxo-5,6-dihydro-4H-[1,3,4]thiadiazin-2-yl)-phenyl]-2-oxo-oxazolidin-5(S)-ylmethyl}-isoxazol-3-yl-carbamic acid 2,2,2-trichloro-ethyl ester (0.100 g, 0.176 mmol) in acetic acid (3 ml) and the mixture is stirred vigorously at room temperature for 2 hours. The reaction mixture is filtered, the filtrate evaporated to dryness, and the residue is purified by PTLC (10% MeOH/DCM) to give the product.

The intermediate for the synthesis of above compound is prepared as follows:
I. {3-[3-Fluoro-4-(5-oxo-5,6-dihydro-4H-[1,3,4]thiadiazin-2-yl)-phenyl]-2oxo-oxazolidin-5(S)-ylmethyl}-isoxazol-3-yl-carbamic acid 2,2,2-trichloro-ethyl ester

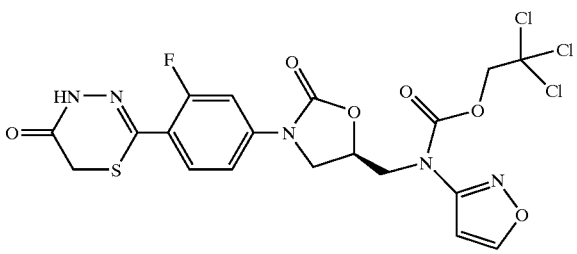

2-[2-Fluoro-4-(5(R)-hydroxymethyl)-2-oxo-oxazolidin-3-yl)-phenyl]-4H-[1,3,4]thiadiazin-5-one (0.200 g, 0.615 mmol), 3-(2,2,2-trichloroethoxycarbonylamino)isoxazole (0.239 g, 0.923 mmol) (prepared similarly to the compound in Example 3 on page 58 of WO 00/21960), and triphenylphosphine (0.241 g, 0.923 mmol) are dissolved in DMF (5 ml) and cooled in an ice bath. Diisopropyl azodicarboxylate (0.182 ml, 0.923 mmol) is added dropwise and the mixture is allowed to warm to room temperature. The reaction mixture is evaporated to dryness and the residue is purified by PTLC (10% MeOH/DCM) to give product.

Example 36
2-{2-Fluoro-4-[5(S)-(isoxazol-3-yloxymethyl)-2-oxo-oxazolidin-3-yl]-phenyl}-4H-[1,3,4]thiadiazin-5-one

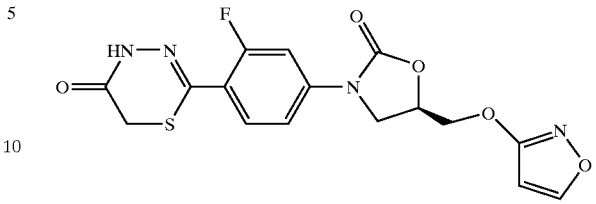

Diisopropyl azodicarboxylate (0.145 ml, 0.738 mmol) is added dropwise at room temperature to a mixture of 2-[2-fluoro-4-(5(R)-hydroxymethyl)-2-oxo-oxazolidin-3-yl)-phenyl]-4H-[1,3,4]thiadiazin-5-one (0.200 g, 0.615 mmol), 3-hydroxyisoxazole (0.0627 g, 0.738 mmol) [prepared according to the method found in U.S. Pat. No. 3,687,968], and triphenylphosphine (0.209 g, 0.800 mmol) in THF (10 ml). The reaction mixture is stirred at room temperature for 2 hours and then evaporated to dryness. The residue is purified by PTLC (10% MeOH/DCM).

Example 37
N-{3-[3-Fluoro-4-(5-oxo-5,6-dihydro-4H-[1,3,4]thiadiazin-2-yl-phenyl]-2-oxo-oxazolidin-5-ylmethyl}-3-(4-hydroxyphenyl)-acrylamide

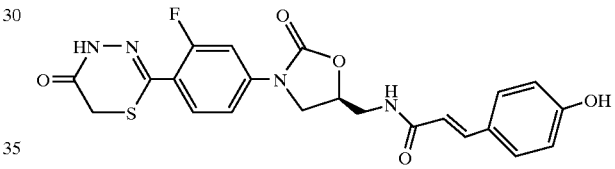

Acetic acid 4-[2-([3-[fluoro-4-(5-oxo-5,6-dihydro-4H-[1,3,4]thiadiazin-2-yl)-phenyl]-2-oxo-oxazolidin-5-ylmethyl}-carbamoyl)-vinyl]-phenyl ester (0.050 g, 0.0976 mmol) is dissolved in a 0.1 M lithium hydroxide in methanol (1.5 ml) and is stirred at room temperature for 15 minutes. The reaction mixture is neutralized with acetic acid and the resulting precipitate is collected by filtration. The white solid is washed with water, methanol and ether, and then dried under vacuum (0.032 g, 70%); ¹HNMR (300 MHz, DMSO-d₆) δ overlapping 3.57 (t, J=5.4, 2H) and 3.59 (s, 2H), 3.81 (dd, J=6.3, 9 Hz, 1H), 4.18 (t, J=9 Hz, 1H), 4.83 (m, 1H), 6.45 (d, J=15.9 Hz, 1H), 6.78 (d, J=8.4 Hz, 2H), 7.32–7.45 (m, 4H), 7.60 (dd, J=2.1, 13.8 Hz, 2H), 7.69 (t, J=8.4 Hz, 1H), 8.39 (t, J=6 Hz, 1H), 9.86 (s, 1H); MS (m/z): [M+H]⁺= 471.

The intermediate for the synthesis of above compound is prepared as follows:
I. Acetic acid 4-[2-([3-[fluoro-4-(5-oxo-5,6-dihydro-4H-[1,3,4]thiadiazin-2-2-oxo-oxazolidin-5-ylmethyl}-carbamoyl)-vinyl]-phenyl ester

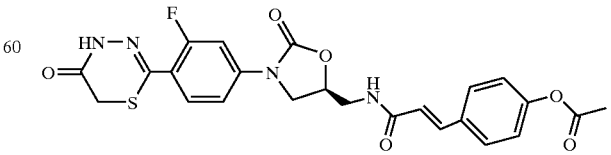

N,N-Diisopropylethylamine (0.507 ml, 2.91 mmol) is added to 3-(4-Acetoxyphenyl)-acrylic acid (0.200 g, 0.97 mmol) and O-(7-azabenzotriazol-1-yl)-N,N,N',N'-tetramethyluronium hexafluorophosphate (0.553 g, 1.46 mmol) in DMF (8 ml) and is stirred for 20 minutes at room temperature. 2-[4-(5(S)-aminomethyl-2-oxo-oxazolidin-3-yl)-2-fluorophenyl]-4H-[1,3,4]thiadiazin-5-one (0.378 g, 1.16 mmol; prepared as described for Example 1) is added and stirring at room temperature is continued overnight. The reaction mixture is partially evaporated under vacuum, diluted with water (5 ml), and extracted with ethyl acetate (50 ml). The extract is washed with brine, dried (MgSO$_4$), and evaporated. The residue was purified by PTLC (5% MeOH/DCM) to give pure product as a white solid (0.2 g, 40%); MS (m/z): [M+H]$^+$=513.

Example 38
Phosphoric acid mono-{4-[2-({3-[3-fluoro-4-(5-oxo-5,6-dihydro-4H-[1,3,4]thiadiazin-2-yl)-phenyl]-2-oxo-oxazolidin-5-ylmethyl}-carbamoyl)-vinyl]-phenyl} ester N,N-Diisopropylethylamine (0.507 ml, 2.91 mmol) was added to 3-[4-(diethoxy-phosphoryloxy)phenyl]acrylic acid (0.065 g, 0.217 mmol) [prepared according to the procedure described in *Tetrahedron Lett* 1996, 37, 3635] and O-(7-azabenzotriazol-1-yl)-N,N,N',N'-tetramethyluronium hexafluorophosphate (0.124 g 0.326 mmol) in DMF (3 ml) and stirred for 20 minutes at room temperature. 2-[4-(5(S)-aminomethyl-2-oxo-oxazolidin-3-yl)-2-fluorophenyl]-4H-[1,3,4]thiadiazin-5-one (0.084 g, 0.259 mmol) was added and stirring continued at room temperature overnight. The reaction mixture was partially evaporated under vacuum, diluted with water (5 ml), and extracted with ethyl acetate (50 ml). The extract was washed with brine, dried (MgSO$_4$), and evaporated. The residue was purified by PTLC (5% MeOH/DCM) to give pure product as a white solid (0.71 g, 54%); MS (m/z): [M+H]$^+$=607.

While the invention has been described and illustrated herein by references to various specific material, procedures

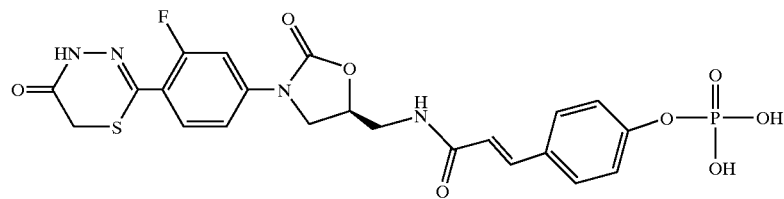

Phosphoric acid diethyl ester 4-[2-([3-[3-fluoro-5,6-dihydro-4H-[1,3,4]thiadiazin-2-yl)-phenyl]-2-oxo-oxazolidin-5-ylmethyl}-carbamoyl)-vinyl]-phenyl ester (0.170 g, 0.280 mmol) is suspended in acetonitrile and iodotrimethylsilane (0.060 ml, 0.420 mmol) is added dropwise. The suspension becomes clear and the reaction is stirred at room temperature for 2 hours under nitrogen. The mixture is concentrated under vacuum, and the residue is diluted with water (5 ml) and washed with dichloromethane (3×10 ml). The aqueous layer is evaporated under vacuum and the residue is purified by HPLC (methanol/water gradient) to give pure product as a white solid (0.062 g, 40%); $^1$HNMR (300 MHz, DMSO-d$_6$) 3.59 (m, 4H), 3.82 (dd, J=6.6, 9.3 Hz, 1H), 4.19 (t, J=9 Hz, 1H), 4.85 (m, 1H), 6.60 (d, J=15.6 Hz, 1H), 7.19 (d, J=8.4 Hz, 2H), 7.40–7.72 (m, 6H), 8.51 (t, J=6 Hz, 1H), 11.6 (s, 1H); MS (m/z): [M+H]$^+$=551.

The intermediate for the synthesis of above compound is prepared as follows:

I. Phosphoric acid diethyl ester-{4-[2-({3-[3-fluoro-4-(5-oxo-5,6-dihydro-4H-[1,3,4]thiadiazin-2-yl)-phenyl]-2-oxo-oxazolidin-5-ylmethyl}-carbamoyl)-vinyl]-phenyl} ester and examples, it is understood that the invention is not restricted to the particular material combinations of material, and procedures selected for that purpose. Numerous variations of such details can be implied as will be appreciated by those skilled in the art.

What is claimed is:
1. A compound of the following formula I

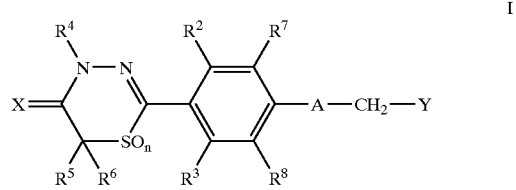

or a pharmaceutically acceptable salt thereof wherein:

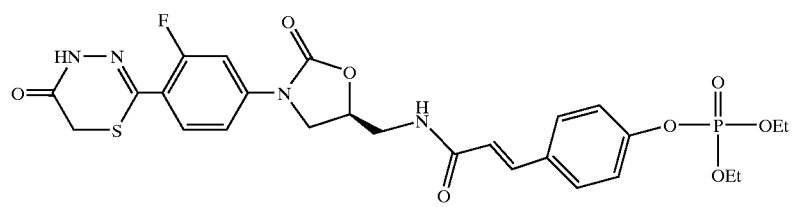

A is a structure of the following formula i, ii, iii, or iv

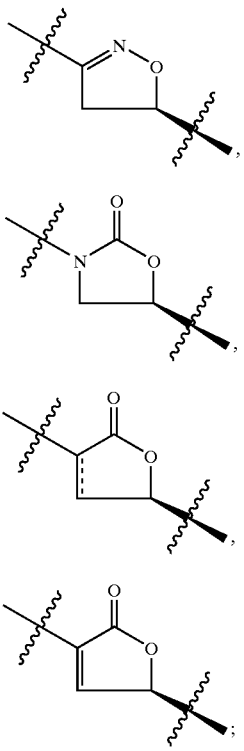

X is O or S;
Y is
  (a) —NHC(=O)R$^1$,
  (b) —NHC(=S)R$^1$,
  (c) —NHC(=NCN)R$^1$,
  (d) —NH-het$^1$,
  (e) —O-het$^1$,
  (f) —S-het$^1$,
  (g) -het$^2$, or
  (h) —OH;
R$^1$ is
  (a) —H,
  (b) —NH$_2$,
  (c) —NHC$_{1-4}$alkyl,
  (d) —C$_{1-4}$alkyl,
  (e) —C$_{2-4}$alkenyl,
  (i) —C$_{1-4}$heteroalkyl,
  (g) —(CH$_2$)$_m$C(=O)C$_{1-4}$alkyl,
  (h) —OC$_{1-4}$alkyl,
  (i) —SC$_{1-4}$alkyl,
  (j) —(CH$_2$)$_p$C$_{3-6}$cycloalkyl,
  (k) —(CH$_2$)$_r$C(=O)aryl, or
  (l) —(CH$_2$)$_s$C(=O)het$^1$;
R$^2$, R$^3$, R$^7$, and R$^8$ are independently
  (a) —H,
  (b) —Cl,
  (c) —F,
  (d) —CH$_3$,
  (e) —NH$_2$, or
  (f) —OH;
R$^4$ is
  (a) —H,
  (b) —C$_{1-4}$alkyl,
  (c) —C$_{1-4}$heteroalkyl,
  (d) —(CH$_2$)$_q$C(=O)OC$_{1-4}$alkyl,
  (e) —(CH$_2$)$_m$C(=O)C$_{1-4}$alkyl,
  (f) -aryl, or
  (g) -het$^1$;
R$^5$ and R$^6$ are independently
  (a) —H,
  (b) —F,
  (c) —C$_{1-4}$alkyl,
  (d) —C$_{3-6}$cycloalkyl,
  (e) —C$_{1-4}$heteroalkyl,
  (f) -aryl,
  (g) -het$^1$,
  (h) —OC$_{1-4}$alkyl,
  (i) —O(C=O)C$_{1-4}$alkyl,
  (j) —(C=O)OC$_{1-4}$alkyl; or
  (k) R$^5$ and R$^6$ taken together are C$_{3-6}$cycloalkyl;
n, m, p, q, r and s at each occurrence are independently 0, 1, or 2;
het$^1$ at each occurrence is independently a C-linked 5 or 6 membered heterocyclic ring having 1 to 4 heteroatoms selected from the group consisting of oxygen, nitrogen, and sulfur within the ring;
het$^2$ at each occurrence is independently a N-linked 5 or 6 membered heterocyclic ring having 1 to 4 nitrogen and optionally having one oxygen or sulfur within the ring; and
wherein at each occurrence the alkyl, alkenyl, and cycloalkyl groups independently are optionally substituted with one, two, or three substituents selected from the group consisting of halo, aryl, het$^1$, and het$^2$.

2. A compound of formula I according to claim 1, wherein A is an optical configuration of the following formula i, ii, or iii:

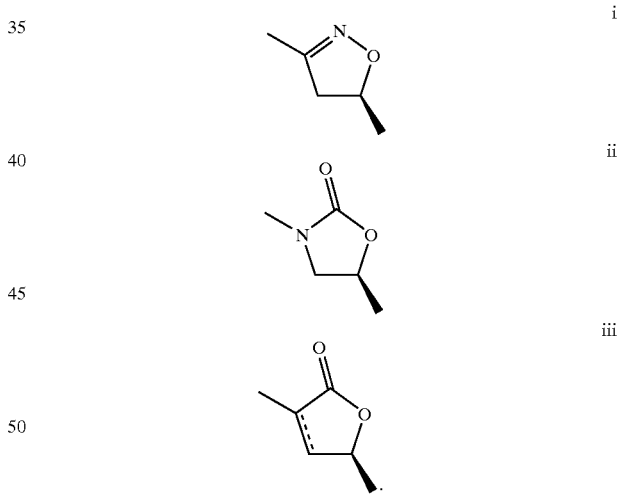

3. A compound of formula I according to claim 1, wherein A is an optical configuration of the following formula ii:

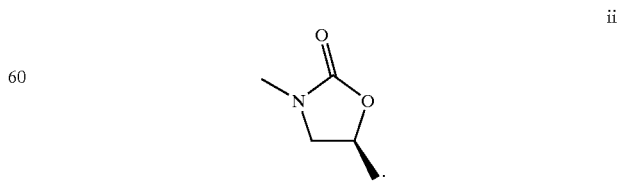

4. A compound of formula I according to claim 1, wherein R$^1$ is —C$_{1-4}$alkyl or —C$_{1-4}$heteroalkyl.

5. A compound of formula I according to claim 1, wherein $R^1$ is methyl, difluoromethyl, ethyl, 2-fluoroethyl, or 2,2-difluoroethyl.

6. A compound of formula I according to claim 1, wherein $R^2$ and $R^3$ are independently —H or —F.

7. A compound of formula I according to claim 1, wherein one of $R^2$ and $R^3$ is —H and the other is —F.

8. A compound of formula I according to claim 1, wherein $R^4$ is —H, —$C_{1-4}$alkyl, or —C(=O)O$C_{1-4}$alkyl.

9. A compound of formula I according to claim 1, wherein $R^5$ and $R^6$ are —H.

10. A compound of formula I according to claim 1, wherein one of $R^5$ and $R^6$ is —H and the other is —$C_{1-4}$alkyl, —$C_{3-6}$cycloalkyl, or -aryl.

11. A compound of formula I according to claim 1, wherein $R^5$ and $R^6$ taken together are —$C_{3-6}$cycloalkyl.

12. A compound of formula I according to claim 1, wherein n is 0.

13. A compound of formula I according to claim 1, wherein the compound is of the following formula II

II

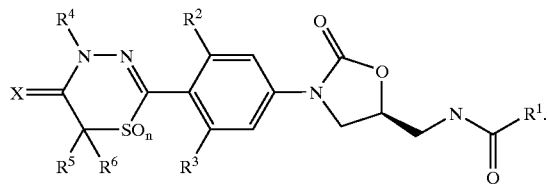

14. A compound of formula II according to claim 13, wherein $R^1$ is —$C_{1-4}$alkyl or —$C_{1-4}$heteroalkyl.

15. A compound of formula II according to claim 13, wherein $R^1$ is methyl, difluoromethyl, ethyl, 2-fluoroethyl, or 2,2-difluoroethyl.

16. A compound of formula II according to claim 13, wherein $R^2$ and $R^3$ are independently —H or —F.

17. A compound of formula II according to claim 13, wherein one of $R^2$ and $R^3$ is —H and the other is —F.

18. A compound of formula II according to claim 13, wherein $R^4$ is —H, —$C_{1-4}$alkyl, or —C(=O)O$C_{1-4}$alkyl.

19. A compound of formula II according to claim 13, wherein $R^5$ and $R^6$ are —H.

20. A compound of formula II according to claim 13, wherein one of $R^5$ and $R^6$ is —H and the other is —$C_{1-4}$alkyl, —$C_{3-6}$cycloalkyl, or -aryl.

21. A compound of formula II according to claim 13, wherein $R^5$ and $R^6$ taken together are —$C_{3-6}$cycloalkyl.

22. A compound of formula I according to claim 1, wherein the compound is of the following formula III

III

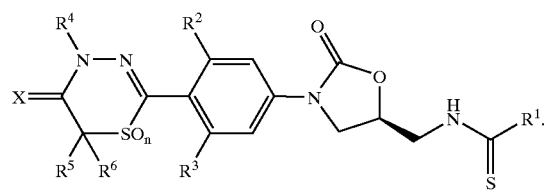

23. A compound of formula III according to claim 22, wherein $R^1$ is —$C_{1-4}$alkyl or —$C_{1-4}$heteroalkyl.

24. A compound of formula III according to claim 22, wherein $R^1$ is methyl, difluoromethyl, ethyl, 2-fluoroethyl, or 2,2-difluoroethyl.

25. A compound of formula III according to claim 22, wherein $R^2$ and $R^3$ are independently —H or —F.

26. A compound of formula III according to claim 22, wherein one of $R^2$ and $R^3$ is —H and the other is —F.

27. A compound of formula III according to claim 22, wherein $R^4$ is —H, —$C_{1-4}$alkyl, or —C(=O)O$C_{1-4}$alkyl.

28. A compound of formula III according to claim 22, wherein $R^5$ and $R^6$ are —H.

29. A compound of formula III according to claim 22, wherein one of $R^5$ and $R^6$ is —H and the other is —$C_{1-4}$alkyl, —$C_{3-6}$cycloalkyl, or -aryl.

30. A compound of formula III according to claim 22, wherein $R^5$ and $R^6$ taken together are —$C_{3-6}$cycloalkyl.

31. A compound of formula I according to claim 1, wherein the compound is of the following formula IV

IV

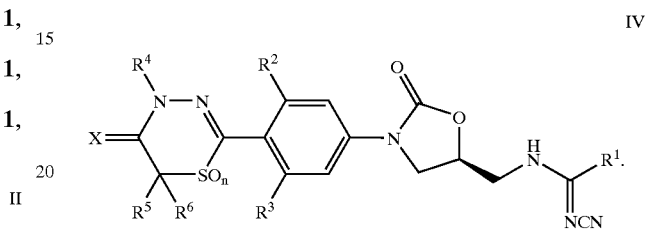

32. A compound of formula IV according to claim 31, wherein $R^1$ is —$C_{1-4}$alkyl or —$C_{1-4}$heteroalkyl.

33. A compound of formula IV according to claim 31, wherein $R^1$ is methyl, difluoromethyl, ethyl, 2-fluoroethyl, or 2,2-difluoroethyl.

34. A compound of formula IV according to claim 31, wherein $R^2$ and $R^3$ are independently —H or —F.

35. A compound of formula IV according to claim 31, wherein one of $R^2$ and $R^3$ is —H and the other is —F.

36. A compound of formula IV according to claim 31, wherein $R^4$ is —H, —$C_{14}$alkyl, or —C(=O)O$C_{1-4}$alkyl.

37. A compound of formula IV according to claim 31, wherein $R^5$ and $R^6$ are —H.

38. A compound of formula IV according to claim 31, wherein one of $R^5$ and $R^6$ is —H and the other is —$C_{1-4}$alkyl, —$C_{3-6}$cycloalkyl, or -aryl.

39. A compound of formula IV according to claim 31, wherein $R^5$ and $R^6$ taken together are —$C_{3-6}$cycloalkyl.

40. A compound of formula I according to claim 1, wherein the compound is of the following formula V

V

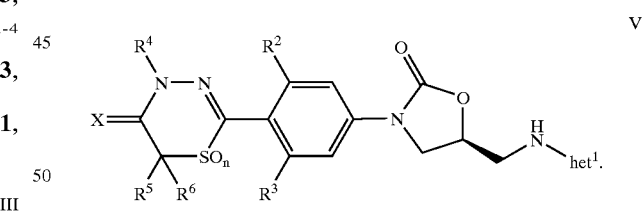

41. A compound of formula V according to claim 40, wherein one of $R^2$ and $R^3$ is —H and the other is —F.

42. A compound of formula V according to claim 40, wherein $R^4$ is —H, —$C_{1-4}$alkyl, or —C(=O)O$C_{1-4}$alkyl.

43. A compound of formula V according to claim 40, wherein one of $R^5$ and $R^6$ is —H and the other is —$C_{1-4}$alkyl, —$C_{3-6}$cycloalkyl, or -aryl.

44. A compound of formula V according to claim 40, wherein $R^5$ and $R^6$ taken together are $C_{3-6}$cycloalkyl.

45. A compound of formula V according to claim 40, wherein -$het^1$ is 2-pyridyl, 3-pyridyl, 4-pyridyl, 3-isoxaz-olyl, 4-is-oxaz-olyl, 5-isoxaz-olyl, 1,2,3-triazol-1-yl, or 1,2,5-thiadiazol-3-yl group.

46. A compound of formula I according to claim 1, wherein the compound is of the following formula VI

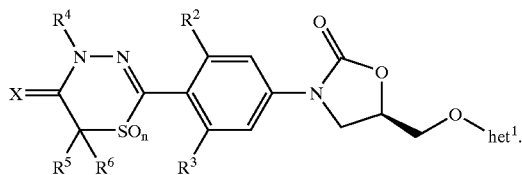

47. A compound of formula VI according to claim 46, wherein one of $R^2$ and $R^3$ is —H and the other is —F.

48. A compound of formula VI according to claim 46, wherein $R^4$ is —H, —$C_{1-4}$alkyl, or —C(=O)O$C_{1-4}$alkyl.

49. A compound of formula VI according to claim 46, wherein one of $R^5$ and $R^6$ is —H and the other is —$C_{1-4}$alkyl, —$C_{3-6}$cycloalkyl, or -aryl.

50. A compound of formula VI according to claim 46, wherein $R^5$ and $R^6$ taken together are $C_{3-6}$cycloalkyl.

51. A compound of formula VI according to claim 46, wherein het$^1$ is 2-pyridyl, 3-pyridyl, 4-pyridyl, 3-isoxazolyl, 4-is-oxaz-olyl, 5-isoxaz-olyl, 1,2,3-triazol-1-yl, or 1,2,5-thiadiazol-3-yl.

52. A compound of formula I according to claim 1, wherein the compound is of the following formula VII

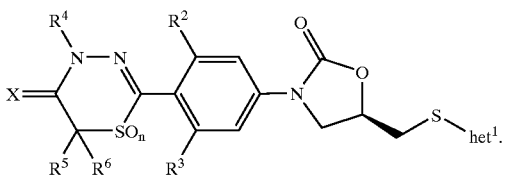

53. A compound of formula VII according to claim 52, wherein one of $R^2$ and $R^3$ is —H and the other is —F.

54. A compound of formula VII according to claim 52, wherein $R^4$ is —H, —$C_{1-4}$alkyl, or —C(=O)O$C_{1-4}$alkyl.

55. A compound of formula VII according to claim 52, wherein one of $R^5$ and $R^6$ is —H and the other is —$C_{1-4}$alkyl, —$C_{3-6}$cycloalkyl, or -aryl.

56. A compound of formula VII according to claim 52, wherein $R^5$ and $R^6$ taken together are $C_{3-6}$cycloalkyl.

57. A compound of formula VII according to claim 52, wherein het$^1$ is 2-pyridyl, 3-pyridyl, 4-pyridyl, 3-isoxazolyl, 4-is-oxaz-olyl, 5-isoxaz-olyl, 1,2,3-triazol-1-yl, or 1,2,5-thiadiazol-3-yl.

58. A compound of formula I according to claim 1, wherein the compound is of the following formula VIII

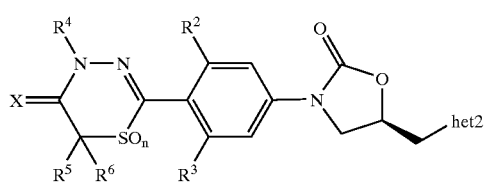

59. A compound of formula VIII according to claim 58, wherein one of $R^2$ and $R^3$ is —H and the other is —F.

60. A compound of formula VIII according to claim 58, wherein $R^4$ —H, —$C_{1-4}$alkyl, or —C(=O)O$C_{1-4}$alkyl.

61. A compound of formula VIII according to claim 58, wherein one of $R^5$ and $R^6$ is —H and the other is —$C_{1-4}$alkyl, —$C_{3-6}$cycloalkyl, or -aryl.

62. A compound of formula VIII according to claim 58, wherein $R^5$ and $R^6$ taken together are $C_{3-6}$cycloalkyl.

63. A compound of formula VIII according to claim 58, wherein het$^2$ is pyrrolyl, imidazolyl, pyrazolyl, 1,2,3-triazolyl, 1,2,4-triazolyl, 1,2,3,4-tetrazolyl, or isoxazolidinonyl.

64. A compound according to claim 1, which is selected from the group consisting of
(a) N-{3-[3-fluoro-4-(5-oxo-5,6-dihydro-4H-[1,3,4]thiadiazin-2-yl)-phenyl]-2-oxo-oxazolidin-5(S)-ylmethyl}-acetamide;
(b) N-{3-[3-fluoro-4-(6(S)-methyl-5-oxo-5,6-dihydro-4H-[1,3,4]thiadiazin-2-yl)-phenyl]-2-oxo-oxazolidin-5(S)-ylmethyl}-acetamide;
(c) N-{3-[3-fluoro-4-(6(R)-methyl-5-oxo-5,6-dihydro-4H-[1,3,4]thiadiazin-2-yl)-phenyl]-2-oxo-oxazolidin-5(S)-ylmethyl}-acetamide;
(d) N-{3-[3-fluoro-4-(5-oxo-5,6-dihydro-4H-[1,3,4]thiadiazin-2-yl)-phenyl]-2-oxo-oxazolidin-5(S)-ylmethyl}-propionamide;
(e) cyclopropanecarboxylic acid {3-[3-fluoro-4-(5-oxo-5,6-dihydro-4H-[1,3,4]thiadiazin-2-yl)-phenyl]-2-oxo-oxazolidin-5(S)-ylmethyl}-amide;
(f) {3-[3-fluoro-4-(5-oxo-5,6-dihydro-4H-[1,3,4]thiadiazin-2-yl)-phenyl]-2-oxo-oxazolidin-5(S)-ylmethyl}-urea;
(g) N-{3-[3-fluoro-4-(5-oxo-5,6-dihydro-4H-[1,3,4]thiadiazin-2-yl)-phenyl]-2-oxo-oxazolidin-5(S)-ylmethyl}-carbamic acid methyl ester;
(h) N-{3-[3-fluoro-4-(5-oxo-5,6-dihydro-4H-[1,3,4]thiadiazin-2-yl)-phenyl]-2-oxo-oxazolidin-5(S)-ylmethyl}-thioacetamide;
(i) N-{3-[3-fluoro-4-(5-thioxo-5,6-dihydro-4H-[1,3,4]thiadiazin-2-yl)-phenyl]-2-oxo-oxazolidin-5(S)-ylmethyl}-thioacetamide;
(j) N-{3-[3-fluoro-4-(5-thioxo-5,6-dihydro-4H-[1,3,4]thiadiazin-2-yl)-phenyl]-2-oxo-oxazolidin-5(S)-ylmethyl}-acetamide;
(k) 2-[2-fluoro-4-(5(R)-hydroxymethyl)-2-oxo-oxazolidin-3-yl)-phenyl]-4H-[1,3,4]thiadiazin-5-one;
(l) 2-{2-fluoro-4-[5(S)-(isoxazol-3-ylaminomethyl)-2-oxo-oxazolidin-3-yl]-phenyl}-4H-[1,3,4]thiadiazin-5-one;
(m) 2-{2-fluoro-4-[5(S)-(isoxazol-3-yloxymethyl)-2-oxo-oxazolidin-3-yl]-phenyl}-4H-[1,3,4]thiadiazin-5-one; and
(n) N-{3-[3-fluoro-4-(5-oxo-5,6-dihydro-4H-[1,3,4]thiadiazin-2-yl)-phenyl]-2-oxo-oxazolidin-5-ylmethyl}-3-(4-hydroxyphenyl)-acrylamide.

65. A compound according to claim 1, which is selected from the group consisting of
(a) N-{3-[4-(6,6-dimethyl-5-oxo-5,6-dihydro-4H-[1,3,4]thiadiazin-2-yl)-3-fluorophenyl]-2-oxo-oxazolidin-5(S)-ylmethyl}-acetamide;
(b) N-{3-[3-fluoro-4-(6-ethyl-5-oxo-5,6-dihydro-4H-[1,3,4]thiadiazin-2-yl)-phenyl]-2-oxo-oxazolidin-5(S)-ylmethyl}-acetamide;
(c) N-{3-[3-fluoro-4-(9-oxo-5-thia-7,8-diazaspiro[3.5]non-6-en-6-yl)-phenyl]-2-oxo-oxazolidin-5(S)-ylmethyl}-acetamide;
(d) N-{3-[3-fluoro-4-(5-oxo-6-phenyl-5,6-dihydro-4H-[1,3,4]thiadiazin-2-yl)-phenyl]-2-oxo-oxazolidin-5(S)-ylmethyl}-acetamide;
(e) N-{3-[3-fluoro-4-(5-oxo-5,6-dihydro-4H-[1,3,4]thiadiazin-2-yl)-phenyl]-2-oxo-oxazolidin-5(S)-ylmethyl}-2-hydroxyacetamide;

(f) N-{3-[3-fluoro-4-(5-oxo-5,6-dihydro-4H-[1,3,4]thiadiazin-2-yl)-phenyl]-2-oxo-oxazolidin-5(S)-ylmethyl}-carbamic acid tert-butyl ester;

(g) N-{3-[3-fluoro-4-(5-oxo-5,6-dihydro-4H-[1,3,4]thiadiazin-2-yl)-phenyl]-2-oxo-oxazolidin-5(S)-ylmethyl}-3-oxo-butyramide;

(h) N-{3-[3-fluoro-4-(5-oxo-5,6-dihydro-4H-[1,3,4]thiadiazin-2-yl)-phenyl]-2-oxo-oxazolidin-5(S)-ylmethyl}-3-(4-fluorophenyl)-3-oxo-propionamide;

(i) N-{3-[3-fluoro-4-(5-oxo-5,6-dihydro-4H-[1,3,4]thiadiazin-2-yl)-phenyl]-2-oxo-oxazolidin-5(S)-ylmethyl}-3-[4-(hydroxyimino-methyl)-phenyl]-acrylamide;

(j) N-{3-[3-fluoro-4-(5-oxo-5,6-dihydro-4H-[1,3,4]thiadiazin-2-yl)-phenyl]-2-oxo-oxazolidin-5(S)-ylmethyl}-3-[4-(methoxyimino-methyl)-phenyl]-acrylamide;

(k) N-{3-[4-(6,6-dimethyl-1,1,5-trioxo-1,4,5,6-tetrahydro-1$\lambda^6$-[1,3,4]thiadiazin-2-yl)-3-fluorophenyl]-2-oxo-oxazolidin-5(S)-ylmethyl}-acetamide;

(l) N-{3-[3-fluoro-4-(4-methyl-5-oxo-5,6-dihydro-4H-[1,3,4]thiadiazin-2-yl)-phenyl]-2-oxo-oxazolidin-5(S)-ylmethyl}-acetamide; and (m) phosphoric acid mono-{4-[2-({3-[3-fluoro-4-(5-oxo-5,6-dihydro-4H-[1,3,4]thiadiazin-2-yl)-phenyl]-2-oxo-oxazolidin-5-ylmethyl}-carbamoyl)-vinyl]-phenyl} ester.

66. A compound according to claim 1, which is selected from the group consisting of (a) N-{3-[3-fluoro-4-(5-oxo-6-propyl-5,6-dihydro-4H-[1,3,4]thiadiazin-2-yl)-phenyl]-2-oxo-oxazolidin-5(S)-ylmethyl}-acetamide;

(b) N-{3-[3-fluoro-4-(6-isopropyl-5-oxo-5,6-dihydro-4H-[1,3,4]thiadiazin-2-yl)-phenyl]-2-oxo-oxazolidin-5(S)-ylmethyl}-acetamide;

(c) N-{3-[3-fluoro-4-(6-fluoro-5-oxo-5,6-dihydro-4H-[1,3,4]thiadiazin-2-yl)-phenyl]-2-oxo-oxazolidin-5(S)-ylmethyl}-acetamide;

(d) N-{3-[3-fluoro-4-(6-hydroxymethyl-5-oxo-5,6-dihydro-4H-[1,3,4]thiadiazin-2-yl)-phenyl]-2-oxo-oxazolidin-5(S)-ylmethyl}-acetamide;

(e) N-{3-[3-fluoro-4-(6-(2-hydroxyethyl)-5-oxo-5,6-dihydro-4H-[1,3,4]thiadiazin-2-yl)-phenyl]-2-oxo-oxazolidin-5(S)-ylmethyl}-acetamide;

(f) 2-{4-[5(S)-(acetylaminomethyl)-2-oxo-oxazolidin-3-yl]-2-fluorophenyl}-5-oxo-5,6-dihydro-4H-[1,3,4]thiadiazine-6-carboxylic acid methyl ester;

(g) N-(3-{3-fluoro-4-(6-(4-hydroxyphenyl)-5-oxo-5,6-dihydro-4H-[1,3,4]thiadiazin-2-yl)-phenyl}-2-oxo-oxazolidin-5(S)-ylmethyl)-acetamide;

(h) N-{3-[3-fluoro-4-(5-thioxo-5,6-dihydro-4H-[1,3,4]thiadiazin-2-yl)-phenyl]-2-oxo-oxazolidin-5(S)-ylmethyl}-carbamic acid tert-butyl ester;

(i) N-{3-[4-(6,6-dimethyl-1,5-dioxo-1,4,5,6-tetrahydro-1$\lambda^4$-[1,3,4]-thiadiazin-2-yl)-3-fluorophenyl]-2-oxo-oxazolidin-5(S)-ylmethyl}-acetamide;

(j) acetic acid 2-{4-[5(S)-(acetylaminomethyl)-2-oxo-oxazolidin-3-yl]-2-fluorophenyl}-5-oxo-5,6-dihydro-4H-[1,3,4]thiadiazin-6-yl ester; and (k) (2-{4-[5(S)-(acetylaminomethyl)-2-oxo-oxazolidin-3-yl]-2-fluorophenyl}-5-oxo-5,6-dihydro-[1,3,4]thiadiazin-4-yl)-acetic acid methyl ester.

67. A method for the treatment of a bacterial infection in a mammal comprising administering to the mammal a therapeutically effective amount of a compound of claim 1.

68. The method according to claim 67, wherein the compound is administered to the mammal orally, parenterally, transdermally, topically, rectally, or intranasally in a pharmaceutical composition.

69. The method according to claim 67, wherein the compound is administered in an amount of from about 0.1 to about 100 mg/kg of body weight/day.

70. The method according to claim 69, wherein the compound is administered in an amount of from about 1 to about 50 mg/kg of body weight/day.

71. The method according to claim 67, wherein the infection is a skin infection.

72. The method according to claim 67, wherein the infection is an eye infection.

73. A pharmaceutical composition comprising a therapeutically effective amount of a compound of claim 1 and a pharmaceutically acceptable carrier.

* * * * *